United States Patent
Kawabe et al.

(10) Patent No.: US 12,313,638 B2
(45) Date of Patent: May 27, 2025

(54) METHOD FOR ANALYZING BLOOD COAGULATION CHARACTERISTICS OF BLOOD SPECIMEN

(71) Applicants: SEKISUI MEDICAL CO., LTD., Chuo-ku (JP); PUBLIC UNIVERSITY CORPORATION NARA MEDICAL UNIVERSITY, Kashihara (JP)

(72) Inventors: Toshiki Kawabe, Chuo-ku (JP); Yukio Oda, Chuo-ku (JP); Midori Shima, Kashihara (JP); Keiji Nogami, Kashihara (JP); Kenichi Ogiwara, Kashihara (JP)

(73) Assignees: SEKISUI MEDICAL CO., LTD., Chuo-ku (JP); PUBLIC UNIVERSITY CORPORATION NARA MEDICAL UNIVERSITY, Kashihara (JP)

( * ) Notice: Subject to any disclaimer, the term of this patent is extended or adjusted under 35 U.S.C. 154(b) by 748 days.

(21) Appl. No.: 17/427,000

(22) PCT Filed: Jan. 31, 2020

(86) PCT No.: PCT/JP2020/003796
§ 371 (c)(1),
(2) Date: Jul. 29, 2021

(87) PCT Pub. No.: WO2020/158948
PCT Pub. Date: Aug. 6, 2020

(65) Prior Publication Data
US 2022/0146537 A1    May 12, 2022

(30) Foreign Application Priority Data
Jan. 31, 2019  (JP) .................................. 2019-016474

(51) Int. Cl.
*G01N 33/86* (2006.01)
*G01N 21/47* (2006.01)

(52) U.S. Cl.
CPC ............. *G01N 33/86* (2013.01); *G01N 21/47* (2013.01)

(58) Field of Classification Search
CPC .... G01N 33/86; G01N 21/47; G01N 33/4905; G16H 50/20
See application file for complete search history.

(56) References Cited

U.S. PATENT DOCUMENTS

| | | | |
|---|---|---|---|
| 6,524,861 B1 * | 2/2003 | Anderson | G01N 33/86 422/65 |
| 2006/0167369 A1 * | 7/2006 | Montgomery | A61B 5/24 600/544 |

(Continued)

FOREIGN PATENT DOCUMENTS

| | | |
|---|---|---|
| JP | 2016-118442 A | 6/2016 |
| JP | 2016-194426 A | 11/2016 |

(Continued)

OTHER PUBLICATIONS

Shapiro, Amy D, and Whitney Sealls. Hemophilia B. Wayback Machine, National Organization for Rare Disorders, web.archive.org/web/20170715000000*/https://rarediseases.org/rare-diseases/hemophilia-b/. Accessed Mar. 14, 2024 (Year: 2017).*

(Continued)

*Primary Examiner* — Andrey Shostak
(74) *Attorney, Agent, or Firm* — Oblon, McClelland, Maier & Neustadt, L.L.P.

(57) ABSTRACT

To provide a method for analyzing coagulation characteristics of a blood specimen. To provide a method for analyzing a blood specimen, including: acquiring a waveform related to a coagulation rate or coagulation acceleration of a sample obtained by mixing a subject blood specimen with a reagent (Continued)

for measuring coagulation time; extracting multiple parameters characterizing the waveform related to a coagulation rate or a coagulation acceleration; and determining an activity level or activity abnormality of a coagulation factor in the subject blood specimen on the basis of the multiple parameters.

15 Claims, 17 Drawing Sheets

(56) References Cited

U.S. PATENT DOCUMENTS

| | | | | |
|---|---|---|---|---|
| 2013/0344519 | A1* | 12/2013 | Leong | G01N 33/86 435/13 |
| 2016/0178651 | A1 | 6/2016 | Shima et al. | |
| 2016/0291042 | A1 | 10/2016 | Kumano et al. | |
| 2018/0031539 | A1 | 2/2018 | Shima et al. | |
| 2018/0045709 | A1 | 2/2018 | Shima et al. | |

FOREIGN PATENT DOCUMENTS

| | | |
|---|---|---|
| JP | 2017-106925 A | 6/2017 |
| JP | 2018-17619 A | 2/2018 |
| JP | 2019-86518 A | 6/2019 |

OTHER PUBLICATIONS

Katayama, Haruna, et al. "An evaluation of hemostatic abnormalities in patients with hemophilia according to the activated partial thromboplastin time waveform." Clinical and Applied Thrombosis/Hemostasis 24.7 (2018): 1170-1176 (Year: 2018).*

Matsumoto, Takeshi, et al. "An evaluation of the activated partial thromboplastin time waveform." Clinical and Applied Thrombosis/Hemostasis 24.5 (2018): 764-770 (Year: 2018).*

Extended European Search Report issued Oct. 7, 2022, in corresponding European Patent Application No. 20749235.6 9 pages.

Shima M., et al., "Towards standardization of clot waveform analysis and recommendations for its clinical applications", J. Thromb. Haemost., vol. 11, No. 7, Jul. 1, 2013, pp. 1417-1420, doi: 10.1111/jth. 12287. XP055853877.

Katayama Haruna, et al., "An Evaluation of Hemostatic Abnormalities in Patients with Hemophilia According to the Activated Partial Thromboplastin Time Waveform", Clinical and Applied Thrombosis/Hemostasis, vol. 24, No. 7, Oct. 1, 2018, pp. 1170-1176, XP055821801, ISSN: 1076-0296, DOI: 10.1177/1076029618757344, Retrieved from the Internet: URL:https://journals.sagepub.com/doi/pdf/10.1177/1076029618757344.

International Search Report issued Mar. 31, 2020 in PCT/JP2020/003796 filed Jan. 31, 2020, 3 pages.

Downey, C., et al., "Novel and diagnostically applicable information from optical waveform analysis of blood coagulation in disseminated intravascular coagulation", British Journal of Haematology, vol. 68, 1997, pp. 68-73.

Yamasaki, N., et al., "Is the result of Colt Waveform Analysis (CWA) different in hemophilia A and B?", Japan Journal of Thrombosis and Hemostasis, vol. 58, No. 9, 2017, 3 total pages (w/ English translation).

Nishiyama, A., et al., "Detection of Very Low Levels of Factor IX of Severe Hemophilia B by Clot Waveform Analysis", Japanese Journal of Thrombosis and Hemostasis, vol. 29, No. 2, 2018, 5 total pages (w/ English translation).

Wada, H., "APTT waveform", Japanese Journal of Thrombosis and Hemostasis, vol. 29, No. 4, 2018, 24 total pages (w/ English translation).

Ogiwara, K., et al., "Development of hemophilia A diagnosis algorithm by APTT coagulation waveform template matching", Japanese Journal of Thrombosis and Hemostasis, vol. 30, No. 2, 2019, 5 total pages (w/ English translation) sheet(s) attached.

* cited by examiner

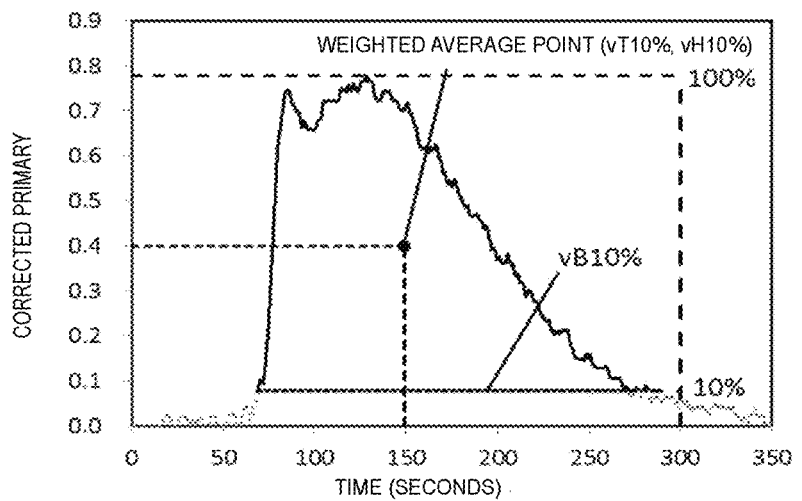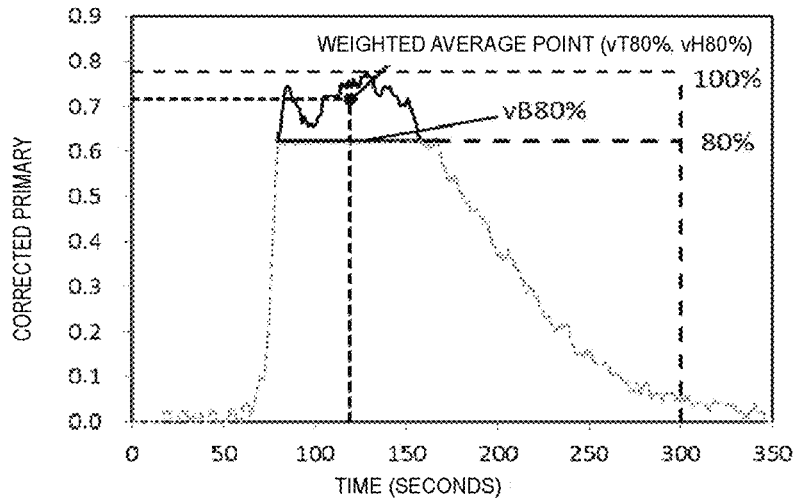

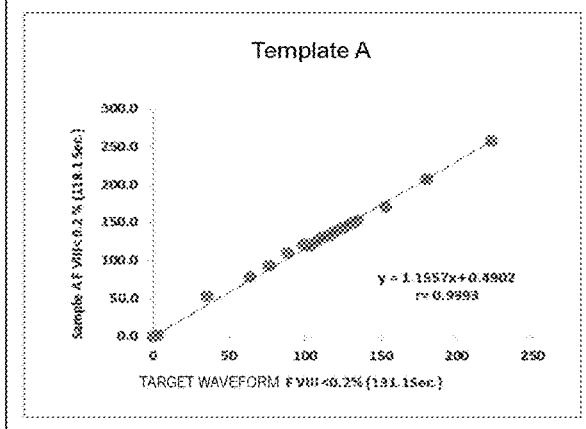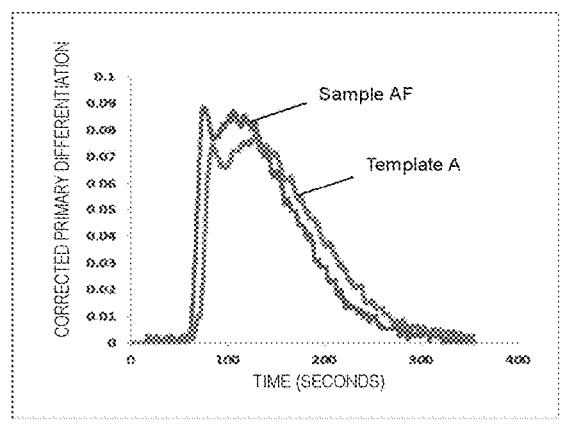

METHOD FOR ANALYZING BLOOD COAGULATION CHARACTERISTICS OF BLOOD SPECIMEN

This application is a national stage application of PCT/JP2020/003796, filed Jan. 31, 2020, which claims priority to JP2019-016474, filed Jan. 31, 2019 the entire contents of which is incorporated herein by reference.

FIELD OF THE INVENTION

The present invention relates to a method for analyzing blood coagulation characteristics of a blood specimen. Further, the present invention relates to a program and an apparatus, for analyzing blood coagulation characteristics of a blood specimen.

BACKGROUND OF THE INVENTION

A blood coagulation test is a test for examining a hemostatic ability or a fibrinolytic capacity, of a patient. In a general blood coagulation test, coagulation reaction that occurs after a reagent is added to a blood specimen of a patient is optically measured. A time that is required to reach a predetermined state of coagulation is measured as the blood coagulation time. Typical examples of the blood coagulation time include prothrombin time (PT), activated partial thromboplastin time (APTT), and thrombin time. The prolongation of the blood coagulation time reflects a bleeding tendency in vivo. As the causes of the prolongation, for example, 1) abnormal amount of blood coagulation factors, 2) presence of antibodies against, for example, blood components constituting the blood coagulation system, and a reagent for measuring the blood coagulation time, and 3) administration of a drug that inhibits the blood coagulation reaction are conceivable.

In the blood coagulation test, a coagulation reaction curve can be obtained by measuring the amount of blood coagulation reaction over time after addition of a reagent to a blood specimen. The coagulation reaction curve has a different shape depending on the type of the abnormality in the blood coagulation system (Non Patent Literature 1). For this reason, a method for determining the abnormality in the blood coagulation system on the basis of a coagulation reaction curve has been disclosed. For example, Patent Literatures 1, 2, and 3 disclose a method for evaluating the presence or absence of abnormalities of coagulation factors in a patient, on the basis of the parameters related to primary and secondary differential curves of a coagulation reaction curve for the blood of the patient, for example, the maximum coagulation rate, the maximum coagulation acceleration, and the maximum coagulation deceleration.

Hemophilia is a disease in which a coagulation factor VIII (FVIII) or a coagulation factor IX (FIX) is congenitally deficient, or functionally abnormal. Assuming that the activity of a healthy individual is 100%, an individual having a FVIII activity of less than 40% is classified as hemophilia A, and an individual having a FIX activity of less than 40% is classified as hemophilia B. Further, the severity of hemophilia is classified in accordance with the activity level. Patent Literature 4 discloses a method for determining the severity of hemophilia on the basis of the average rate of the change in the coagulation rate during the time when the coagulation reaction of a patient reaches the maximum coagulation rate or the maximum coagulation acceleration.

CITATION LIST

Patent Literature

Patent Literature 1: JP 2016-194426 A
Patent Literature 2: JP 2016-118442 A
Patent Literature 3: JP 2017-106925 A
Patent Literature 4: JP 2018-017619 A Non Patent Literature Non Patent Literature 1: British Journal of Haematology, 1997, 98: 68-73

SUMMARY OF THE INVENTION

A primary differential curve of an actual coagulation reaction curve of a blood specimen may not be unimodality due to the influence of the components contained in the specimen or the reagent used in the test, or due to the difference in the measurement method. For this reason, in the methods of Patent Literatures 1 to 4, in order to accurately determine parameters such as a maximum coagulation rate and a maximum coagulation rate time, the waveform analysis is conducted by performing a smoothing treatment to make the primary differential curve unimodal. However, as described above, in a case where the smoothing treatment for making the primary differential curve unimodal is performed, it is assumed that the obtained curve does not reflect the clinical status of a patient in detail because of the loss of the waveform information due to the smoothing treatment. For this reason, an analysis method that can accurately evaluate the blood coagulation characteristics of a specimen even from a primary differential curve that is not unimodal regardless of the smoothing treatment has been demanded.

The present inventors found parameters having a relationship with the activities of coagulation factor VIII (FVIII) and coagulation factor IX (FIX), derived from a coagulation reaction curve of a blood. The present inventors also found a method for analyzing the activity level of FVIII or FIX in a blood specimen and the presence or absence of activity abnormality of FVIII or FIX in a blood specimen, on the basis of the parameters.

Solution to Problem

Accordingly, the present invention provides the following.

[1] A method for analyzing a blood specimen, comprising:
   acquiring a waveform related to a coagulation rate or a coagulation acceleration, of a sample obtained by mixing a subject blood specimen with a reagent for measuring a coagulation time;
   extracting a plurality of parameters characterizing the waveform related to a coagulation rate or a coagulation acceleration; and
   determining an activity level or activity abnormality of a coagulation factor in the subject blood specimen on the basis of the plurality of parameters.

[2] The analysis method according to [1], wherein the plurality of parameters comprise a plurality of parameters characterizing a plurality of calculation target areas, respectively of the waveform related to a coagulation rate, a plurality of parameters characterizing a plurality of calculation target areas, respectively of the waveform related to a coagulation acceleration, or a combination of both pluralities of parameters.

[3] The analysis method according to [2], wherein
the plurality of parameters comprise one or more selected from the group consisting of:
a weighted average time vT, a weighted average height vH, a peak width vB, and a weighted average peak width vW, a B flattening vAB for the weighted average height, a W flattening vAW for the weighted average height, a B time rate vTB for the weighted average time, a W time rate vTW for the weighted average time, an average time vTa, an average height vHa, a B flattening vABa for the average height, a W flattening vAWa for the average height, an area start point time vTs, an area end point time vTe, an area median time vTm, an area time width vTr, a main peak start point time vNs, a main peak end point time vNe, and a main peak width vN for the plurality of calculation target areas of the waveform related to a coagulation rate;
a weighted average time pT, a weighted average height pH, a peak width pB, and a weighted average peak width pW, a B flattening pAB for the weighted average height, a W flattening pAW for the weighted average height, a B time rate pTB for the weighted average time, a W time rate pTW for the weighted average time, a main peak start point time pNs, a main peak end point time pNe, and a main peak width pN for a plurality of calculation target areas of a plus peak of the waveform related to a coagulation acceleration; and
a weighted average time mT, a weighted average height mH, a peak width mB, and a weighted average peak width mW, a B flattening mAB for the weighted average height, a W flattening mAW for the weighted average height, a B time rate mTB for the weighted average time, a W time rate mTW for the weighted average time, a main peak start point time mNs, a main peak end point time mNe, and a main peak width mN for a plurality of calculation target areas of a minus peak of the waveform related to a coagulation acceleration.

[4] The analysis method according to [3], wherein
when the waveform related to a coagulation rate is defined as F(t) (t represents time) and each of t1 and t2 is defined as a time when F(t) is a predetermined value x (t1<t2), the calculation target area is an area satisfying F(t)≥x, and the vT and vH are represented by the following formulas, respectively:

$$vT = \frac{M}{\sum_{i=t1}^{t2} F(i)} \quad (3)$$

$$vH = \frac{M}{\sum_{i=t1}^{t2} i} \quad (4)$$

wherein $$M = \sum_{i=t1}^{t2} (i \times F(i)) \quad (2)$$

the vTa, vHa, and vTm are represented by the following formulas, respectively, when F(t), t1, and t2 are defined as described above and the number of data points from F(t1) to F(t2) is n:

$$vTa = \frac{\sum_{i=t1}^{t2} i}{n} \quad (5)$$

$$vHa = \frac{\sum_{i=t1}^{t2} F(i)}{n} \quad (6)$$

$$vTm = \frac{t1 + t2}{2} \quad (7)$$

the vB represents a time length to be F(t)≥x from t1 to t2,
the vW represents a time length to be F(t)≥vH from t1 to t2,
the vTs and vTe represent t1 and t2, respectively,
the vTr represents a time length from vTs to vTe,
the vNs represents a maximum time during a time period earlier than a time when F(t) shows a maximum value and satisfies F(t)=x in the calculation target area,
the vNe represents a minimum time during a time period later than a time when F(t) shows a maximum value and satisfies F(t)=x in the calculation target area,
the vN represents a time length from vNs to vNe,
the vAB represents a ratio of the vH to the vB,
the vAW represents a ratio of the vH to the vW,
the vTB represents a ratio of the vT to the vB,
the vTW represents a ratio of the vT to the vW,
the vABa represents a ratio of the vHa to the vB, and
the vAWa represents a ratio of the vHa to the vW.

[5] The analysis method according to [3], wherein
when the waveform related to a coagulation acceleration is defined as F'(t) (t represents time) and a time when F'(t) is a predetermined value x is defined as t1, t2 (t1<t2), the calculation target area is an area satisfying F'(t)≥x, and the pT and pH are represented by the following formulas, respectively:

$$pT = \frac{M}{\sum_{i=t1}^{t2} F'(i)} \quad (3)'$$

$$pH = \frac{M}{\sum_{i=t1}^{t2} i} \quad (4)'$$

wherein $$M = \sum_{i=t1}^{t2} (i \times F'(i)) \quad (2)'$$

the pB represents a time length to be F'(t)≥x from t1 to t2,
the pW represents a time length to be F'(t)≥pH from t1 to t2,
the pNs represents a maximum time during a time period earlier than a time when F'(t) shows a maximum value and satisfies F'(t)=x in the calculation target area,
the pNe represents a minimum time during a time period later than a time when F'(t) shows a maximum value and satisfies F'(t)=x in the calculation target area,
the pN represents a time length from pNs to pNe,
the pAB represents a ratio of the pH to the pB,
the pAW represents a ratio of the pH to the pW,
the pTB represents a ratio of the pT to the pB, and
the pTW represents a ratio of the pT to the pW.

[6] The analysis method according to [3], wherein
when the waveform related to a coagulation acceleration is defined as F'(t) (t represents time) and a time when F'(t) is a predetermined value x is defined as t1, t2 (t1<t2), the calculation target area is an area satisfying F'(t)≤x, and the mT and mH are represented by the following formulas, respectively:

$$mT = \frac{M}{\sum_{i=t1}^{t2} F'(i)} \quad (3)''$$

$$mH = \frac{M}{\sum_{i=t1}^{t2} i} \quad (4)''$$

wherein $$M = \sum_{i=t1}^{t2} (i \times F'(i)) \quad (2)''$$

the mB represents a time length to be F'(t)≤x from t1 to t2, the mW represents a time length to be F'(t)≤mH from t1 to t2, the mNs represents a maximum time during a time period earlier than a time when F'(t) shows a minimum value and satisfies F'(t)=x in the calculation target area, the mNe represents a minimum time during a time period later than a time when F'(t) shows a minimum value and satisfies F'(t)=x in the calculation target area, the mN represents a time length from mNs to mNe, the mAB represents a ratio of the mH to the mB, the mAW represents a ratio of the mH to the mW, the mTB represents a ratio of the mT to the mB, and the mTW represents a ratio of the mT to the mW.

[7] The analysis method according to any one of [4] to [6], wherein the predetermined value x is 0.5 to 99% of the maximum value of F(t), 0.5 to 99% of the maximum value of the plus peak of F'(t), or 0.5 to 99% of the minimum value of the minus peak of F'(t).

[8] The analysis method according to any one of [2] to [7], wherein the plurality of calculation target areas are 5 to 20 different areas.

[9] The analysis method according to any one of [1] to [8], wherein the determination comprises comparing a group of the plurality of parameters with a corresponding group of parameters for a plurality of template blood specimens, and determining an activity level or activity abnormality of a coagulation factor in the subject blood specimen on the basis of a result of the comparison, wherein each of the template blood specimens is a blood specimen of which an activity level or presence or absence of activity abnormality of the coagulation factor is known.

[10] The analysis method according to [9], wherein the comparison comprises determining correlation between the group of the parameters for the subject blood specimen and the corresponding group of parameters for a plurality of template blood specimens, respectively.

[11] The analysis method according to [10], wherein the determination comprises selecting a template blood specimen with which the correlation satisfies a predetermined condition, and determining an activity level or activity abnormality of a coagulation factor in the selected template blood specimen as an activity level or activity abnormality of the coagulation factor in the subject blood specimen

[12] The analysis method according to any one of [1] to [11], wherein the coagulation factor is a blood coagulation factor VIII or a blood coagulation factor IX.

[13] The analysis method according to [12], wherein the determination comprises determining a subject blood specimen derived from the patient with hemophilia A.

[14] The analysis method according to [12], wherein the determination comprises determining a subject blood specimen derived from a patient with severe, moderate, or mild hemophilia A.

[15] The analysis method according to [12], wherein the determination comprises determining a subject blood specimen derived from a patient with Very-Severe Haemophilia A, Modestly-Severe Haemophilia A, moderate hemophilia A, or mild hemophilia A.

[16] The analysis method according to [12], wherein the determination comprises determining a subject blood specimen derived from the patient with hemophilia B.

[17] The analysis method according to [12], wherein the determination comprises determining a subject blood specimen derived from a patient with severe, moderate hemophilia B, or mild hemophilia B.

[18] The analysis method according to [12], further comprising:

a second determination step of determining an activity level or activity abnormality of a blood coagulation factor IX in a subject blood specimen with which a blood coagulation factor VIII is determined to be not abnormal, wherein the second determination step comprises comparing a group of parameters for the subject blood specimen with a corresponding group of parameters for a plurality of template blood specimens each of which an activity level or presence or absence of activity abnormality of a blood coagulation factor IX is known, and determining an activity level or activity abnormality of the blood coagulation factor IX in the subject blood specimen on the basis of a result of the comparison.

[19] The analysis method according to [18], wherein the determination comprises determining a subject blood specimen derived from the patient with hemophilia B.

[20] The analysis method according to [18], wherein the determination comprises determining a subject blood specimen derived from a patient with severe, moderate, or mild hemophilia B.

[21] A program for performing the method for analyzing a blood specimen according to any one of [1] to [20].

[22] An apparatus for performing the method for analyzing a blood specimen according to any one of [1] to [20].

Advantageous Effects of the Invention

According to the present invention, on the basis of parameters derived from a coagulation reaction curve, the activity level or the presence or absence of the activity abnormality (for example, deficiency), of FVIII or FIX in a blood specimen can be analyzed. The present invention is useful for the determination of hemophilia A or hemophilia B, or the determination of the severity of a patient with hemophilia.

BRIEF DESCRIPTION OF THE DRAWINGS

FIG. 14A shows a conceptual diagram for illustrating, for example, a weighted average point in a case where the calculation target area level is 10%.

FIG. 14B shows a conceptual diagram for illustrating, for example, a weighted average point in a case where the calculation target area level is 806.

FIG. 17A shows a regression line with a specimen (Template A) having the highest correlation coefficient in FIG. 16.

FIG. 17B shows corrected primary curves of the test specimen (Sample AF) and Template A.

DETAILED DESCRIPTION OF THE INVENTION

The present invention relates to an analysis of the characteristics related to blood coagulation of a blood specimen. Hereinafter, a blood specimen may be referred to as a specimen. More specifically, the present invention relates to an analysis of the activity level or the presence or absence of the activity abnormality, of a blood coagulation time prolongation factor component in a specimen with a prolonged blood coagulation time. Suitably, the present invention relates to an analysis of the activity level or the presence or absence of the activity abnormality, of a coagulation factor VIII (hereinafter, also referred to as FVIII) or a coagulation factor IX (hereinafter, also referred to as FIX). Accordingly, one embodiment of the present invention is a method for analyzing a blood specimen, and more specifically, a method for determining the activity level or the presence or absence of the activity abnormality, of a blood coagulation time prolongation factor component, suitably FVIII and/or FIX in a blood specimen. One embodiment of a procedure for the method according to the present invention will be described below with reference to drawings.

1. Method for Analyzing Blood Specimen 1.1. Overview of Method

Figure 1:
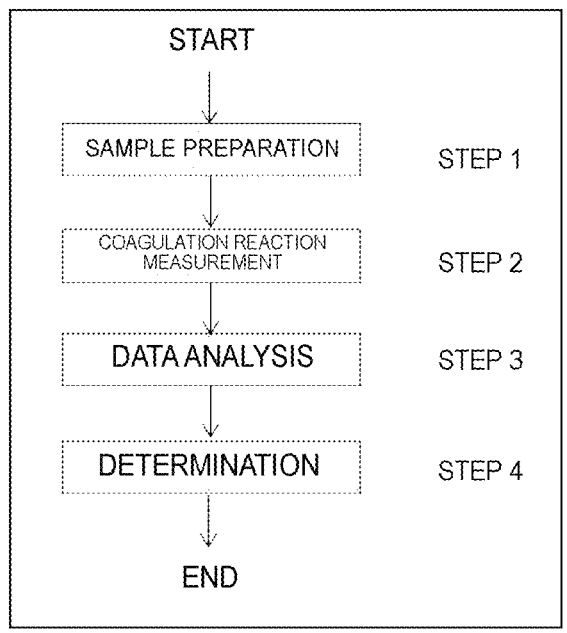
FIG. 1 illustrates one embodiment of a procedure for the method for analyzing a blood specimen according to the present invention.

The method for analyzing a blood specimen according to the present invention (hereinafter, also referred to as the method according to the present invention) includes: acquiring a waveform related to a coagulation rate or a coagulation acceleration, of a sample obtained by mixing a test specimen with a reagent for measuring coagulation time; extracting multiple parameters characterizing the waveform related to the coagulation rate or the coagulation acceleration; and determining an activity level or activity abnormality, of a blood coagulation time prolongation factor component in the test specimen on the basis of the multiple parameters. One embodiment of the method according to the present invention will be described with reference to FIG. 1. In the present method, at first, a sample is prepared from a test specimen (step 1), and then coagulation reaction measurement for the sample is performed (step 2). From the obtained measurement data, a waveform related to the coagulation rate or the coagulation acceleration is acquired for the sample, and then a predetermined analysis is performed on the waveform (step 3). On the basis of the parameters obtained by the analysis, determination (determination of an activity level or activity abnormality, of a blood coagulation time prolongation factor component) of the test specimen is performed (step 4).

1.2. Sample Preparation and Coagulation Reaction Measurement

Preparation of a sample from a test specimen in step 1, and coagulation reaction measurement of the sample in step 2 will be described. Herein, the coagulation reaction measurement will be described with reference to a measurement of an activated partial thromboplastin time (APTT), and changes to other coagulation reaction measurements (for example, prothrombin time (PT) measurement) can be performed by a person skilled in the art.

As an example of the test specimen, a specimen derived from a subject who is required to be inspected for the blood coagulation ability is included, for example, a specimen with abnormal blood coagulation, or a specimen suspected of abnormal blood coagulation is included, and more specifically, a specimen with a prolonged blood coagulation time, or a specimen suspected of a prolonged blood coagulation time is included. Preferably, as the specimen, blood plasma of a subject is used. Into the specimen, a well-known anticoagulant agent that is usually used in a coagulation test can be added. For example, blood is collected with the use of a blood collection tube in which sodium citrate is put, and then centrifuged, as a result of which blood plasma is obtained.

The obtained test specimen is mixed with a reagent for measuring coagulation time, and a sample for coagulation reaction measurement is prepared. As an example of the reagent for measuring coagulation time, a reagent for APTT measurement may be used, and for example, a contact factor-based activator, or a phospholipid can be included. Examples of the activator include ellagic acid, cerite, kaolin, silica, and a polyphenol compound. Examples of the phospholipid include phospholipids derived from an animal, a plant, and synthesis. Examples of the phospholipid derived from an animal include phospholipids derived from a rabbit brain, a chicken, and a pig. Examples of the phospholipid derived from a plant include phospholipids derived from soybeans. Further, a buffer solution such as Tris hydrochloric acid may be added to the sample, as needed. Alternatively, as the reagent for the APTT measurement, a commercially available reagent for measuring APTT may be used. As an example of the commercially available reagent for measuring APTT, Coagpia APTT-N (manufactured by Sekisui Medical Co., Ltd.) is included. The prepared sample is heated, and a contact factor in the sample is activated. The temperature during the heating is, for example, 30° C. or more and 40° C. or less, and preferably 35° C. or more and 39° C. or less.

After that, into a sample containing the test specimen and a reagent for measuring coagulation time, a calcium chloride solution (for example, a calcium chloride solution, Coagpia APTT-N manufactured by Sekisui Medical Co., Ltd.) is added to initiate the blood coagulation reaction. The coagulation reaction of the mixture after addition of the calcium chloride solution can be measured. In the measurement of the coagulation reaction, a common means, for example, an optical means for measuring an amount of scattered light, transmittance, absorbance, or the like, a mechanical means for measuring a viscosity of blood plasma, or the like may be used. The time to be measured can be several tens of seconds to around 5 minutes from the time point of the addition of the calcium chloride solution. During the period of measurement, the measurement can be repeated at predetermined intervals. The measurement may be performed, for example, at 0.1-second intervals. The temperature of the reaction mixture during the measurement is, for example, 30° C. or more and 40° C. or less, and preferably 35° C. or more and 39° C. or less. The reaction start time of the coagulation reaction can be typically defined as the time point when the calcium chloride solution is added to a sample containing a test specimen, however, other timings may be defined as the reaction start time. Further, various kinds of conditions for measurement can be appropriately set depending on, for example, the test specimen, the reagent, or the measuring means.

A series of operations in the above-described coagulation reaction measurement may be performed by using an automatic analyzer. As one example of the automatic analyzer, a blood coagulation automatic analyzer, CP3000 (manufactured by Sekisui Medical Co., Ltd.) can be included. Alternatively, some of the operations may be performed manually. For example, the preparation of the test specimen is performed by a person, and the subsequent operations can be performed by an automatic analyzer.

1.3. Data Analysis
1.3.1. Primary Treatment and Correction Treatment of Data

Figure 2:
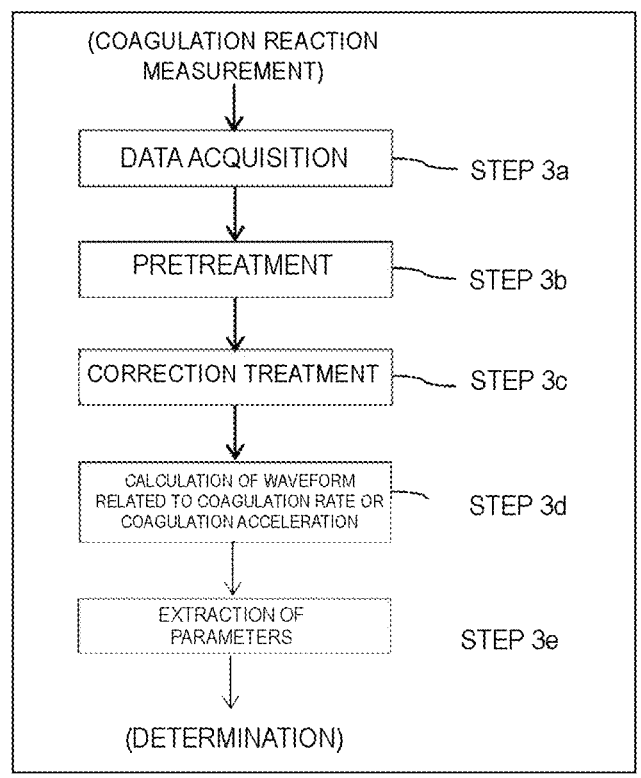
FIG. 2 illustrates one embodiment of a procedure for the step of data analysis shown in FIG. 1.

Next, the data analysis in step 3 will be described. The flow of the data analysis is shown in FIG. 2. The data analysis in step 3 may be performed in parallel with the coagulation reaction measurement in step 2, or may be performed later by using the data of the coagulation reaction measurement performed in advance.

In step 3a, the measurement data in the coagulation reaction measurement is acquired. The data are data that reflect, for example, the coagulation reaction process of a sample, obtained by the APTT measurement in step 2 described above. For example, data indicating the time change of the degree of progress of the coagulation reaction (for example, amount of scattered light) after addition of a calcium chloride solution are acquired from a sample containing a test specimen and a reagent for measuring a coagulation time. The data obtained by the coagulation reaction measurement are also referred to as coagulation reaction information in the present specification.

Figure 3:
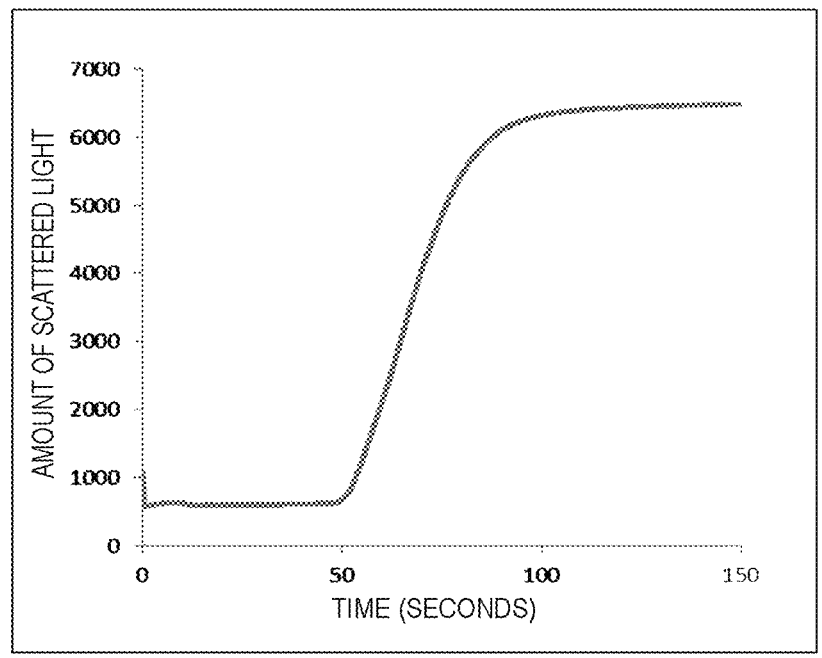
FIG. 3 shows one example of a coagulation reaction curve.

One example of the coagulation reaction information acquired in step 3a is shown in FIG. 3. FIG. 3 is a coagulation reaction curve based on the amount of scattered light, and the horizontal axis indicates the elapsed time (coagulation reaction time) after addition of a calcium chloride solution, and the vertical axis indicates the amount of scattered light. The coagulation reaction of the mixture proceeds with the lapse of time, so that the amount of scattered light is increased. In the present specification, a curve showing the change in the coagulation reaction amount with respect to the coagulation reaction time indicated by, for example, such an amount of scattered light is referred to as a coagulation reaction curve.

The coagulation reaction curve based on the amount of scattered light, as shown in FIG. 3, is usually sigmoid. On the other hand, the coagulation reaction curve based on the amount of transmitted light is usually reverse sigmoid. Hereinafter, in the present specification, data analysis using the coagulation reaction curve based on the amount of scattered light will be described as the coagulation reaction information. It is obvious to a person skilled in the art that similar treatment can be performed also in a case of the data analysis using a coagulation reaction curve based on the amount of transmitted light or the absorbance as the coagulation reaction information. Alternatively, as the coagulation reaction information, the coagulation reaction curve obtained by a mechanical means, such as a viscosity change of a mixture may be subjected to the analysis.

Figure 4:
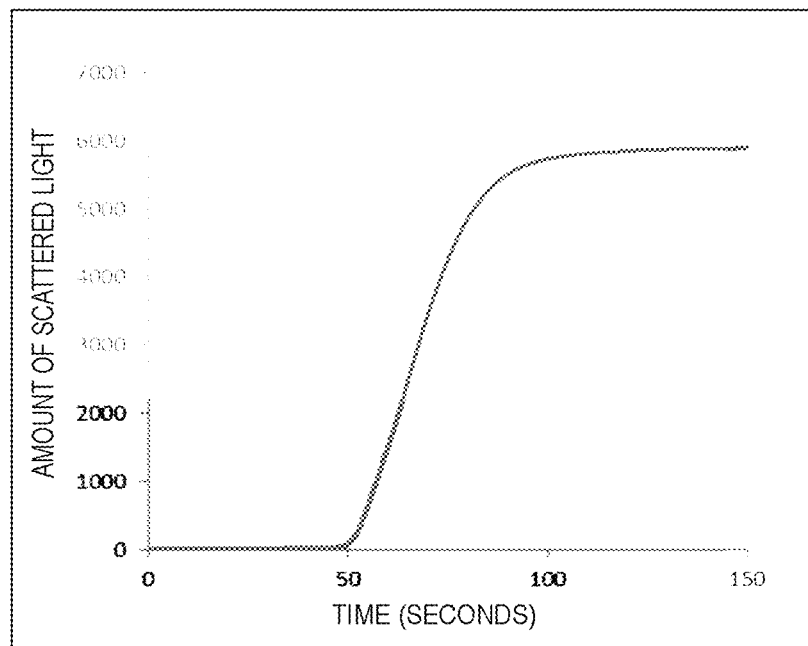
FIG. 4 shows one example of a coagulation reaction curve after pretreatment.
Figure 5A:
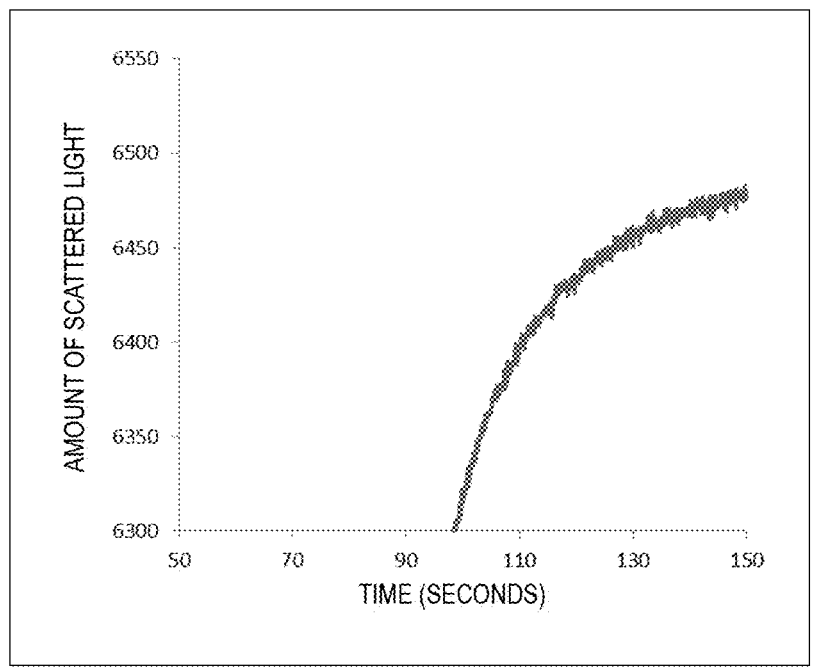
FIG. 5A shows a partially enlarged diagram of one example of a coagulation reaction curve.
Figure 5B:
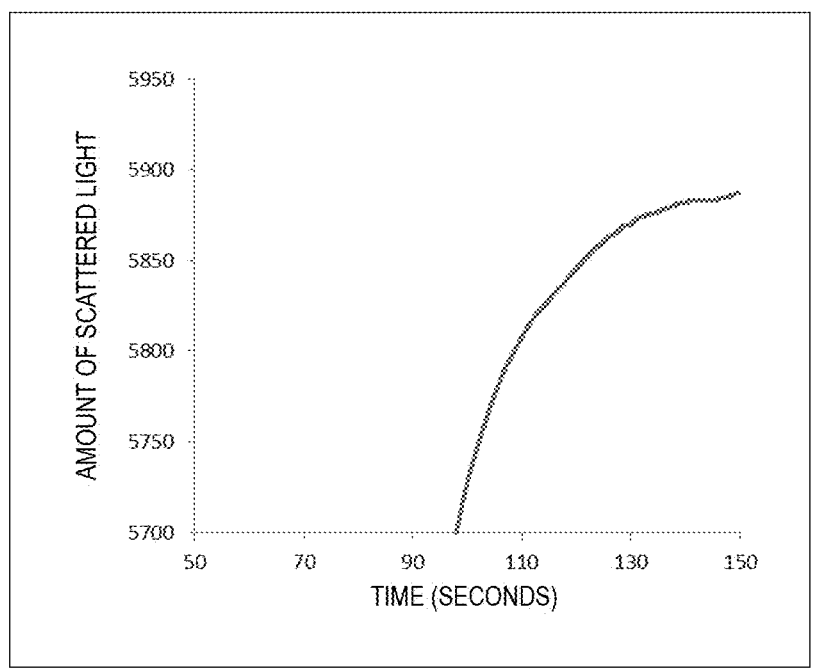
FIG. 5B shows a partially enlarged diagram of one example of a coagulation reaction curve after pretreatment.

In step 3b, a pretreatment of the coagulation reaction curve is performed. The pretreatment includes a smoothing treatment for removing noise, and a zero point adjustment. FIG. 4 shows one example of the coagulation reaction curve of FIG. 3, for which the pretreatment (smoothing treatment and zero point adjustment) has been performed. Any known noise removal method can be used for the smoothing treatment. Further, as shown in FIG. 3, since a mixture containing a test specimen originally scatters light, the amount of scattered light at the starting point of the measurement (time 0) is larger than 0. With the zero point adjustment after the smoothing treatment, the amount of scattered light at time 0 is adjusted to 0 as shown in FIG. 4. FIGS. 5A and 5B show partially enlarged diagrams of the coagulation reaction curve of FIG. 3 before and after the pretreatment, respectively. In FIG. 5B, the smoothing treatment and the zero point adjustment are performed on the data of FIG. 5A.

The height of the coagulation reaction curve depends on the fibrinogen concentration of a test specimen. On the other hand, since the fibrinogen concentration varies among individuals, the height of the coagulation reaction curve differs depending on the test specimen. Accordingly, in the present method, a correction treatment for converting the coagulation reaction curve after the pretreatment into relative values is performed in step 3c, as needed. With the correction treatment, a coagulation reaction curve that does not depend on the fibrinogen concentration can be obtained, and as a result of which the difference in the shape of the coagulation reaction curve after pretreatment can be quantitatively compared among specimens.

In one embodiment, the coagulation reaction curve after pretreatment is corrected so that the maximum value is a predetermined value in the correction treatment. Suitably, in the correction treatment, a corrected coagulation reaction curve P(t) is determined from the coagulation reaction curve after the pretreatment in accordance with the following formula (1). In the formula (1), D(t) represents the coagulation reaction curve after pretreatment, Dmax and Dmin represent the maximum value and minimum value of D(t), respectively, Drange represents the change width (that is, Dmax−Dmin) of D(t), and A is any value representing the maximum value of the corrected coagulation reaction curve.

$$P(t)=[(D(t)-D\text{min})/D\text{range}] \times A \qquad (1)$$

Figure 6:
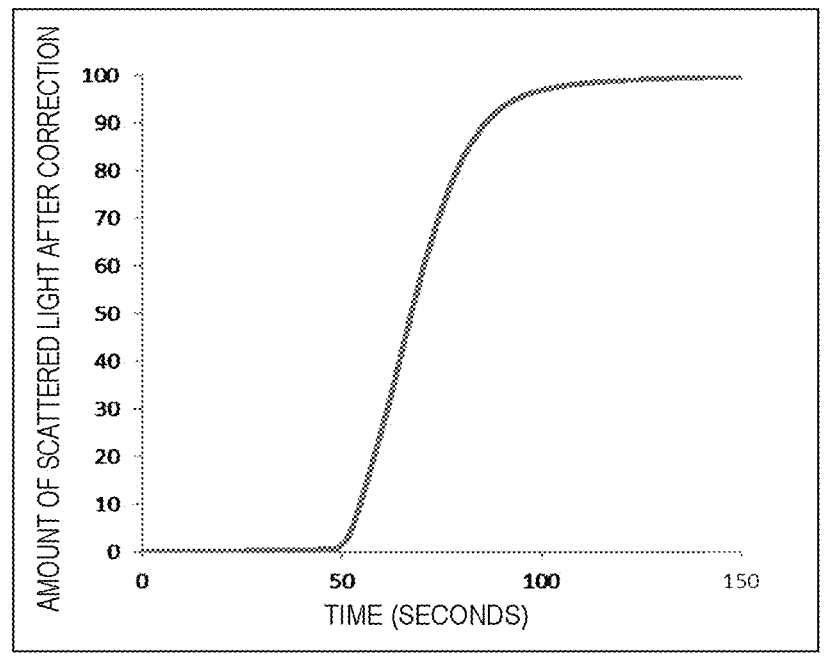
FIG. 6 shows one example of a corrected zero-order curve.

As one example, FIG. 6 shows the data corrected so that the coagulation reaction curve shown in FIG. 4 has a maximum value of 100. In this regard, in FIG. 6, the values have been corrected so as to be from 0 to 100 after the correction, however, may also be other values (for example, from 0 to 10000, that is, A=10000 in the formula (1)). In addition, the correction treatment may not be necessarily performed.

Alternatively, the correction treatment as described above may be performed on a waveform related to the coagulation rate or coagulation acceleration to be described later, or on a parameter group extracted from the waveform. For example, the waveform related to the coagulation rate for the coagulation reaction curve D(t) after pretreatment, to which the correction treatment is not performed, is calculated, and then this can be converted into values corresponding to P(t). Alternatively, a parameter group is extracted from the waveform related to the coagulation rate, and then values of individual parameters included in the parameter group can be converted into the values corresponding to P(t).

In the present specification, a corrected coagulation reaction curve as described above and a coagulation reaction curve without the correction treatment are also referred to as a corrected zero-order curve and an uncorrected zero-order curve, respectively, and further these are also collectively referred to as "zero-order curve". Further, in the present specification, primary differential curves of the corrected zero-order curve and the uncorrected zero-order curve are also referred to as a corrected primary curve and an uncorrected primary curve, respectively, and further these are also collectively referred to as "primary curve". Furthermore, in the present specification, secondary differential curves of the corrected zero-order curve and the uncorrected zero-order curve, or primary differential curves of the corrected primary curve and the uncorrected primary curve are also referred to as a corrected secondary curve and an uncorrected secondary curve, respectively, and further these are also collectively referred to as "secondary curve".

Figure 7:
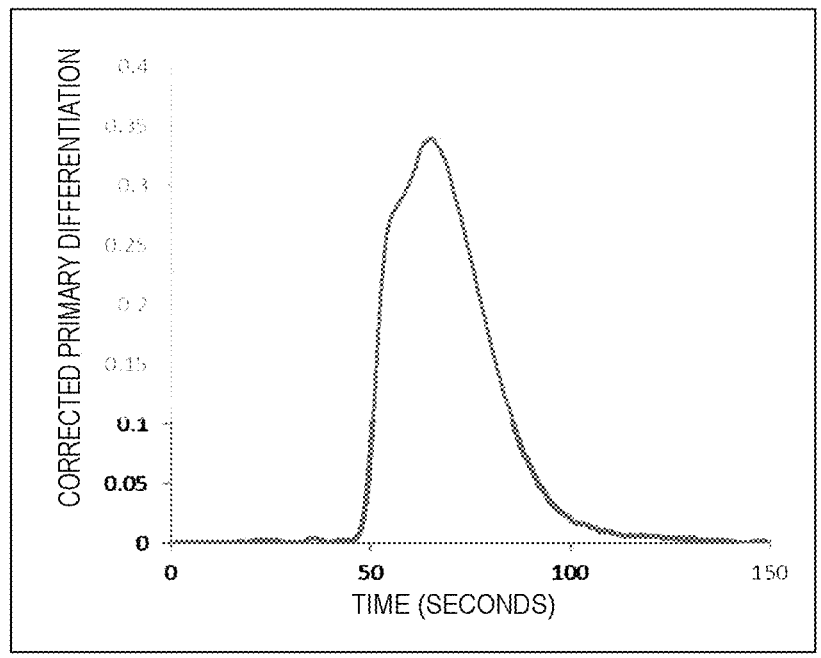
FIG. 7 shows one example of a corrected primary curve.

1.3.2. Calculation of Waveform Related to Coagulation Rate or Coagulation Acceleration In step 3*d*, a waveform related to the coagulation rate or the coagulation acceleration is calculated. In the present specification, the waveform related to the coagulation rate includes an uncorrected primary curve, and a corrected primary curve. The uncorrected primary curve represents the values obtained by primarily differentiating the coagulation reaction curve (uncorrected zero-order curve), that is, the rate (coagulation rate) of the change in the coagulation reaction amount in an arbitrary coagulation reaction time. The corrected primary curve represents the values obtained by primarily differentiating the corrected coagulation reaction curve (corrected zero-order curve), that is, the relative rate of the change in the coagulation reaction amount in an arbitrary coagulation reaction time. Accordingly, the waveform related to the coagulation rate can be a waveform representing the coagulation rate or the relative value of the coagulation rate, in the coagulation reaction of a sample. In the present specification, a value representing the progress of blood coagulation, including the coagulation rate represented by a primary curve and the relative value of the coagulation rate is collectively referred to as a primary differential value. Further, in the present specification, the waveform related to the coagulation acceleration includes an uncorrected secondary curve, and a corrected secondary curve. In the present specification, the values represented by the waveform related to the coagulation acceleration are collectively referred to as a secondary differential value. The primary differentiation and secondary differentiation of the coagulation reaction curve or the corrected coagulation reaction curve (uncorrected and corrected zero-order curves) can be performed by using a known technique. FIG. 7 shows a corrected primary curve obtained by primarily differentiating the corrected zero-order curve shown in FIG. 6. In FIG. 7, the horizontal axis indicates the coagulation reaction time, and the vertical axis indicates the primary differential value.

1.3.3. Extraction of Parameters

In step 3*e*, multiple parameters that characterize the waveform related to the coagulation rate or coagulation acceleration of the sample are extracted. In one embodiment, the multiple parameters include multiple parameters that characterize the waveform related to the coagulation rate. In another embodiment, the multiple parameters include multiple parameters that characterize the waveform related to the coagulation acceleration. In another embodiment, the multiple parameters that characterize the waveform related to the coagulation rate, and the multiple parameters that characterize the waveform related to the coagulation acceleration are used in combination.

Preferably, in the extraction step of parameters in the method according to the present invention, multiple calculation target areas are extracted from the waveform related to the coagulation rate or the coagulation acceleration, and in addition, parameters that characterize these multiple calculation target areas are extracted. As a result, multiple parameters that characterize the multiple calculation target areas for the waveform related to the coagulation rate or the coagulation acceleration are extracted. Accordingly, the multiple parameters that characterize the waveform related to the coagulation rate or the coagulation acceleration, which are extracted in the present invention, include multiple parameters that characterize the multiple calculation target areas of the waveform related to the coagulation rate, include multiple parameters that characterize the multiple calculation target areas of the waveform related to the coagulation acceleration, or include the combination of them. In the method according to the present invention, a parameter group that contains the obtained multiple parameters is prepared. The parameter group reflects the shape of the waveform related to the coagulation rate or the coagulation acceleration, and is related to the blood coagulation characteristics of a specimen. The parameter group is used for the determination (step 4) of a test specimen. The parameters will be described below.

1.3.3.2. Extraction of Calculation Target Area

With respect to the extraction of parameters in the method according to the present invention, a procedure for extracting multiple calculation target areas from a waveform related to the coagulation rate or the coagulation acceleration will be described.

The calculation target area, and the parameters that characterize the calculation target area will be described below by using a waveform related to the coagulation rate as an example. The calculation target area is an area (segment) in which the primary differential value (y value) is a predetermined calculation target area level or more in the waveform (primary curve) related to the coagulation rate. More specifically, the calculation target area is an area (segment) in which the primary differential value (y value) is a predetermined calculation target area level or more and a maximum value (Vmax) or less, and further the maximum point of the waveform is included, in the waveform related to the coagulation rate. The calculation target area level is a predetermined value that specifies the lower limit of the calculation target area, and is also referred to as a calculation target area level S in the present specification. The calculation target area level S can be set to limit the range that reflects a peak shape of the waveform related to the coagulation rate. In order to limit the peak shape relatively widely, the calculation target area level S can be set to 0% to 20° of Vmax. In addition, when the calculation target area level S is increased, the influence of the shape of an upper part of the peak relatively largely reflects on the analysis results. In order to analyze the shape of an upper part of the peak, the calculation target area level S can be set to 20% to 95% of Vmax. In one embodiment, the calculation target area level S can be set to 0.5 to 99°, and preferably 5 to 90% of Vmax.

In the method according to the present invention, multiple calculation target areas are extracted on the basis of multiple different calculation target area levels S. The number of the calculation target areas extracted in the method according to the present invention is not necessarily limited, however, if the number is small, the accuracy of determination of a blood specimen may decrease, and in contrast, if the number is extremely large, the amount of calculation increases and the calculation load increases. The multiple calculation target areas are preferably three or more different areas, more preferably five or more different areas, furthermore preferably 3 to 100 different areas, and still more preferably 5 to 20 different areas. The number of calculation target area levels S corresponds to the number of calculation target areas. The calculation target area levels S for extracting respective calculation target areas are different from each other. From the viewpoint of the analysis accuracy, it is preferable that the levels S are not close to each other. The distance between the levels S may be set depending on the number of calculation target areas, and is preferably 1/100 or more and 1/2 or less of Vmax, more preferably 1/33 or more and 1/5 or less of Vmax, furthermore preferably 1/20 or more and 1/5 or less of Vmax, and still more preferably 1/20 or more and 1/10 or less of Vmax. The distances between Vmax and respective levels S may be the same as or different from each other. The calculation target area level S can also be applied to a secondary curve. The secondary curve can have peaks in both of the plus and minus directions. The calculation target area level S can be set for each of the plus and minus peaks of the secondary curve. In one embodiment, the calculation target area level S can be set to 0.5 to 99%, and preferably 5 to 90% of the maximum value of a plus peak of the secondary curve. In another embodiment, the calculation target area level S can be set to 0.5 to 99%, and preferably 5 to 90% of the minimum value of a minus peak of the secondary curve.

1.3.3.3. Weighted Average Point

Figure 8:
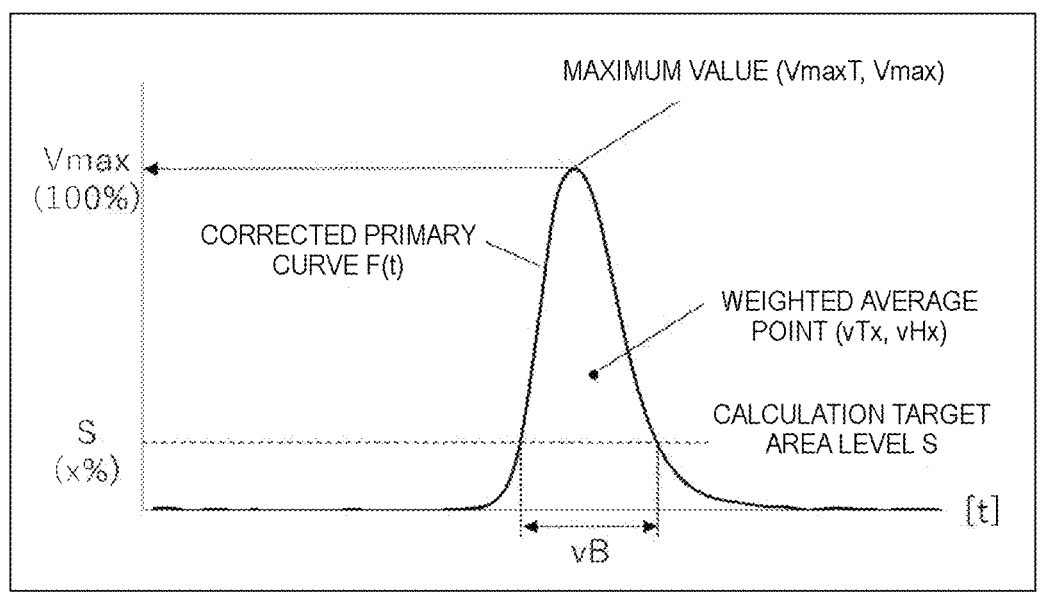
FIG. 8 shows a conceptual diagram of parameters calculated from a waveform related to a coagulation rate.

The calculation target area, and the weighted average point in the calculation target area will be described with reference to FIG. 8. FIG. 8 shows a corrected primary curve F(t) (t=time). Further, FIG. 8 shows the maximum value Vmax of F(t), and the weighted average point (vTx, vHx) and vB representing the peak width of the calculation target area when the calculation target area level S is x % of Vmax, which are parameters described below. The calculation target area is an area in which the value of F(t) is the calculation target area level S or more and the maximum value Vmax or less of the primary differential value (F(t)≥(S=x %)). The weighted average point (vTx, vHx) corresponds to the "weighted average value" in the calculation target area of F(t).

The coagulation reaction time (t) at the weighted average point is defined as the weighted average time vT. That is, the weighted average time vT is a time from the coagulation reaction start time to the weighted average point, and is the x-coordinate of the weighted average point. The weighted average height vH is the y-coordinate of the weighted average point.

The weighted average time vT and weighted average height vH for the primary curve can be obtained by the following procedure. First, the maximum value of the primary curve F(t) is denoted by Vmax, the calculation target area level is denoted by S, and the data group of the times t that satisfy F(t)≥Vmax×S×0.01 are denoted by t[t1, ... t2] (t1<t2). That is, a data group of F(t1)=Vmax×S×0.01, F(t2)=Vmax×S×0.01, and times t1 to t2 is t[t1, ... t2] (t1<t2). At this time, the product sum value M is calculated by the following formula (2).

$$M = \sum_{i=t1}^{t2}(i \times F(i)) \quad (2)$$

The weighted average time vT and the weighted average height vH are calculated by the following formulas (3) and (4), respectively. The weighted average point (vTx, vHx) are led from the obtained vT and vH.

$$vT = \frac{M}{\sum_{i=t1}^{t2} F(i)} \quad (3)$$

$$vH = \frac{M}{\sum_{i=t1}^{t2} i} \quad (4)$$

In the present specification, in order to identify vT and vH that are derived from different calculation target areas, the vT and vH may be referred to as vTx and vHx, respectively, in accordance with the calculation target area level S (S=X %) from which they are derived. For example, the vT and vH in the calculation target area of which S is 5% are vT5% and vH5%, respectively. These weighted average time vTx and weighted average height vHx can be used as parameters that characterize the calculation target area. In this regard, t1 and t2 (t1<t2) that satisfy the above F(t1)=Vmax×S×0.01 and F(t2)=Vmax×S×0.01 can also be parameters, and hereinafter, the t1 and t2 related to the primary curve may be referred to as an area start point time vTs and an area end point time vTe (vTs<vTe), respectively. These may also be referred to as vTsx and vTex, respectively in accordance with the calculation target area level S (S=x %).

Figure 9:
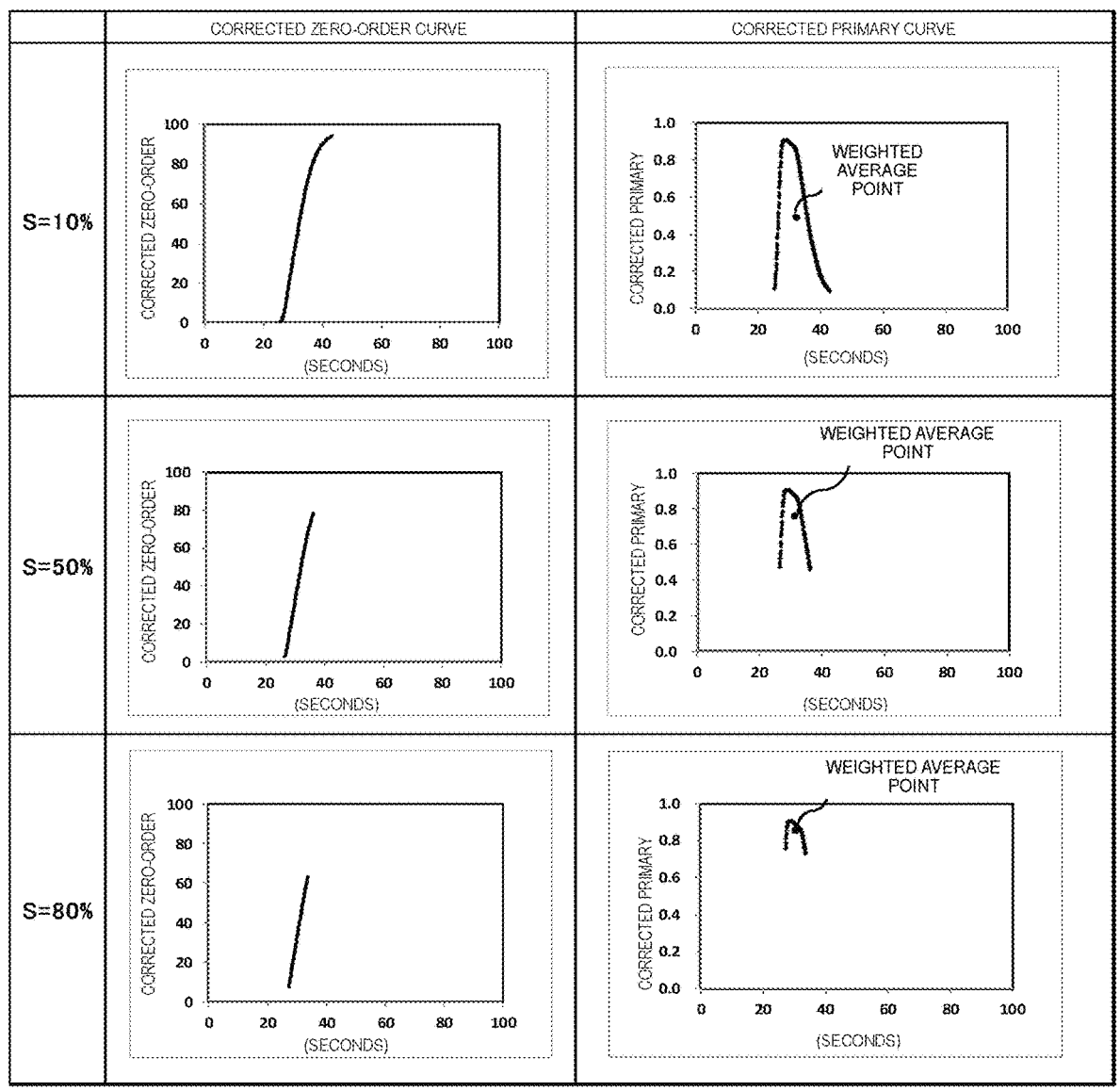
FIG. 9 shows a conceptual diagram for illustrating a calculation target area level, ranges of the corrected zero-order and corrected primary curves to be analyzed, and a weighted average point.

FIG. 9 shows the relationship among the calculation target area level S, the areas (calculation target areas) of the corrected zero-order curve and corrected primary curve to be analyzed at that time, and the weighted average point. In FIG. 9, the upper part, the middle part, and the lower part show the cases where the calculation target area levels S are 10%, 50%, and 80% of Vmax (=100%), respectively. The left indicates the corrected zero-order curves, the right indicates the calculation target areas of the corrected primary curves, and the black circles indicate the weighted average points. As the calculation target area level S changes, the positions of the calculation target area and the weighted average point change as shown in FIG. 9. In the above description, as shown in FIGS. 8 and 9, parameters related to the calculation target area of the corrected primary curve have been calculated, and the similar parameters can be calculated also for the uncorrected primary curve.

Figure 10:
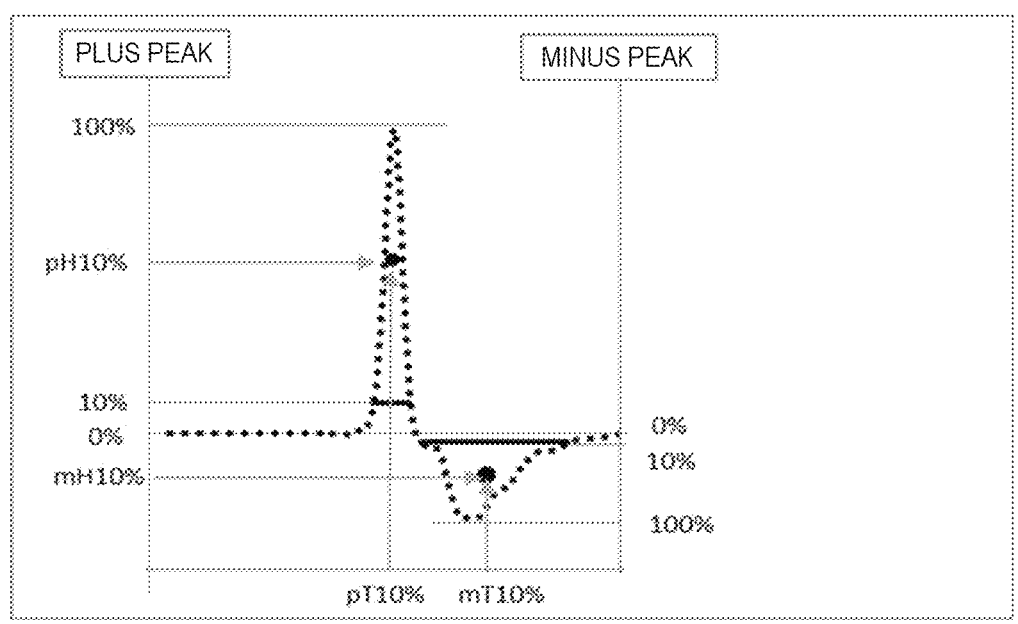
FIG. 10 shows a conceptual diagram of parameters calculated from a secondary curve.

Similarly, also for the secondary curve, the weighted average point, the weighted average time, and the weighted average height can be defined. The secondary curve has peaks in both of the plus and minus directions of the secondary differential value as shown in FIG. 10. For this reason, the weighted average point of the secondary curve can be calculated for both of the plus and minus peaks. For example, for the plus peak, when the maximum value of the secondary curve $A=F'(t)$ is denoted by Amax, and the calculation target area level is denoted by S (%), the times t [t1, . . . t2] (t1<t2) that satisfy $F'(t) \geq A\max \times S \times 0.01$ are determined, and the weighted average time pT and weighted average height pH of the plus peak are calculated in accordance with the above formulas (2)' to (4)'. For the minus peak, when the minimum value of the secondary curve $A=F'(t)$ is denoted by Amin, and the calculation target area level is denoted by S (%), the times t [t1, . . . , t2] (t1<t2) that satisfy $F'(t) \leq A\min \times S \times 0.01$ are determined, and the weighted average time mT and weighted average height mH of the minus peak are calculated in accordance with the above formulas (2)', (3)'', and (4)''. As the calculation target area level S changes, the position of the weighted average point changes.

$$M = \sum_{i=t1}^{t2} (i \times F'(i)) \quad (2)'$$

$$pT = \frac{M}{\sum_{i=t1}^{t2} F'(i)} \quad (3)'$$

$$pH = \frac{M}{\sum_{i=t1}^{t2} i} \quad (4)'$$

$$mT = \frac{M}{\sum_{i=t1}^{t2} F'(i)} \quad (3)''$$

$$mH = \frac{M}{\sum_{i=t1}^{t2} i} \quad (4)''$$

1.3.3.4. Peak Width, Average Point, Flattening, and Time Rate

During the time from the minimum reaction time at which the primary differential value is a value of the calculation target area level S or more in an area in which the reaction time is a time shorter than the weighted average time vT to the maximum reaction time at which the primary differential value is a value of the calculation target area level S or more in an area in which the reaction time is a time longer than the weighted average time vT, the time length at which the primary curve is $F(t) \geq S$ (value obtained by multiplying the number of data points to be $F(t) \geq S$ by the photometric time interval) is defined as the peak width vB of the primary curve. In the example shown in FIG. 8, the peak width vB is from the time vTs to the time vTe. Similarly, the minimum and maximum values of the reaction time at which the secondary differential value at the plus peak of the secondary curve F'(t) is a value of the calculation target area level S or more are pTs and pTe, respectively, and during the time from pTs to pTe, the time length at which $F'(t) \geq S$ is obtained (value obtained by multiplying the number of data points to be $F'(t) \geq S$ by the photometric time interval) is defined as the peak width pB of the plus peak of the secondary curve. Similarly, the minimum and maximum values of the reaction time at which the secondary differential value at the minus peak of the secondary curve F'(t) is a value of the calculation target area level S or less are mTs and mTe, respectively, and during the time from mTs to mTe, the time length at which $F'(t) \leq S$ is obtained (value obtained by multiplying the number of data points to be $F'(t) \leq S$ by the photometric time interval) is defined as the peak width mB of the minus peak of the secondary curve.

Figure 11:
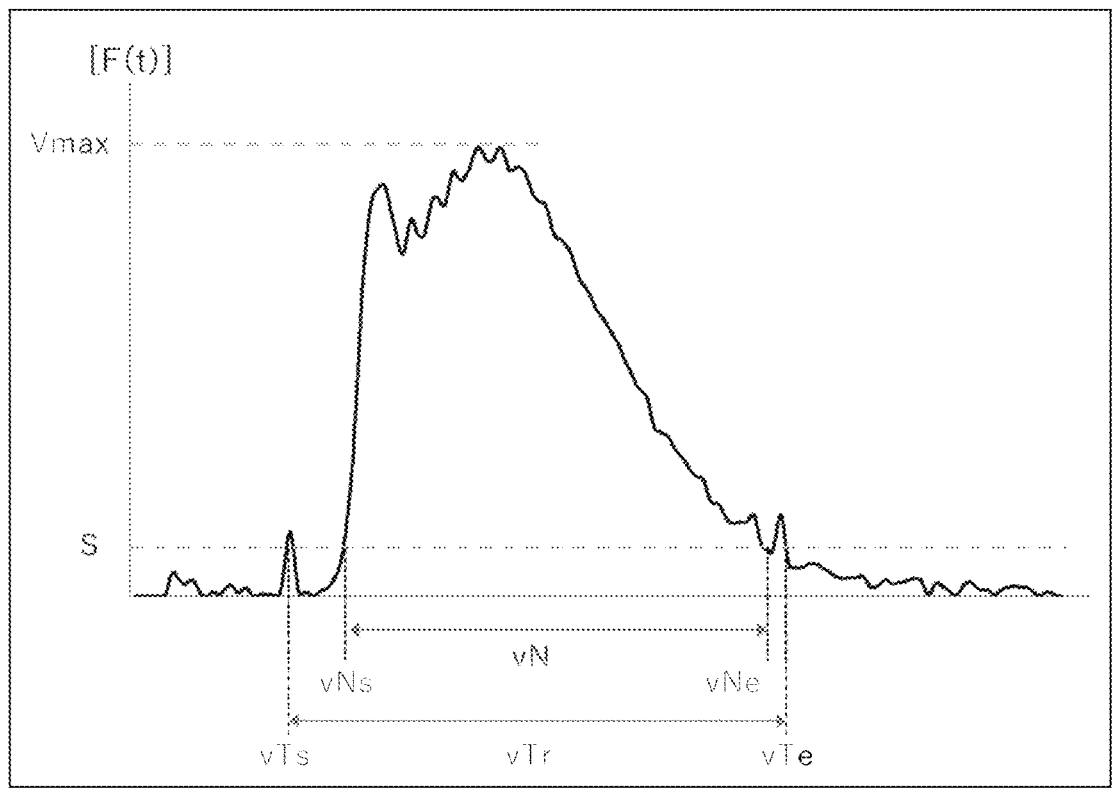
FIG. 11 shows a conceptual diagram for indicating vTs, vTe, vTr, vNs, vNe, and vN.

As another example of the parameters used in the present invention, an area time width vTr can be included. vTr is a width (time length) from vTs to vTe. In a case where the calculation target area of the primary curve is a unimodal peak, vTr=vB is obtained, however, in a case where the primary curve is multimodal including valleys where $F(t) \leq S$ is obtained, vTr>vB is obtained. Other examples of the parameters used in the present invention include a main peak start point time vNs, a main peak end point time vNe, and a main peak width vN. vNs and vNe are parameters for the main peak including the maximum value Vmax in the calculation target area of the primary curve, which are less susceptible to the influence of the noise that may be included in the coagulation reaction curve, as compared with the above vTs, vTe or the like. vNs is a maximum time during the time that is smaller than a time (VmaxT to be described later) at which a maximum value Vmax is shown and further indicates F(t)=S, in the calculation target area of the primary curve F(t). vNe is the minimum time during the time that is larger than a time VmaxT and further indicates F(t)=S, in the calculation target area of the primary curve F(t). In a case where the calculation target area is a unimodal peak, vNs and vNe have the same values as vTs and vTe, respectively. vN is a width (time length) from vNs to vNe. Similarly, for the plus and minus peaks of the secondary curve F'(t), pNs, pNe, pN, mNs, mNe, and mN can be defined in a similar manner. FIG. 11 shows vTs, vTe, vTr, vNs, vNe, and vN.

Figure 12:
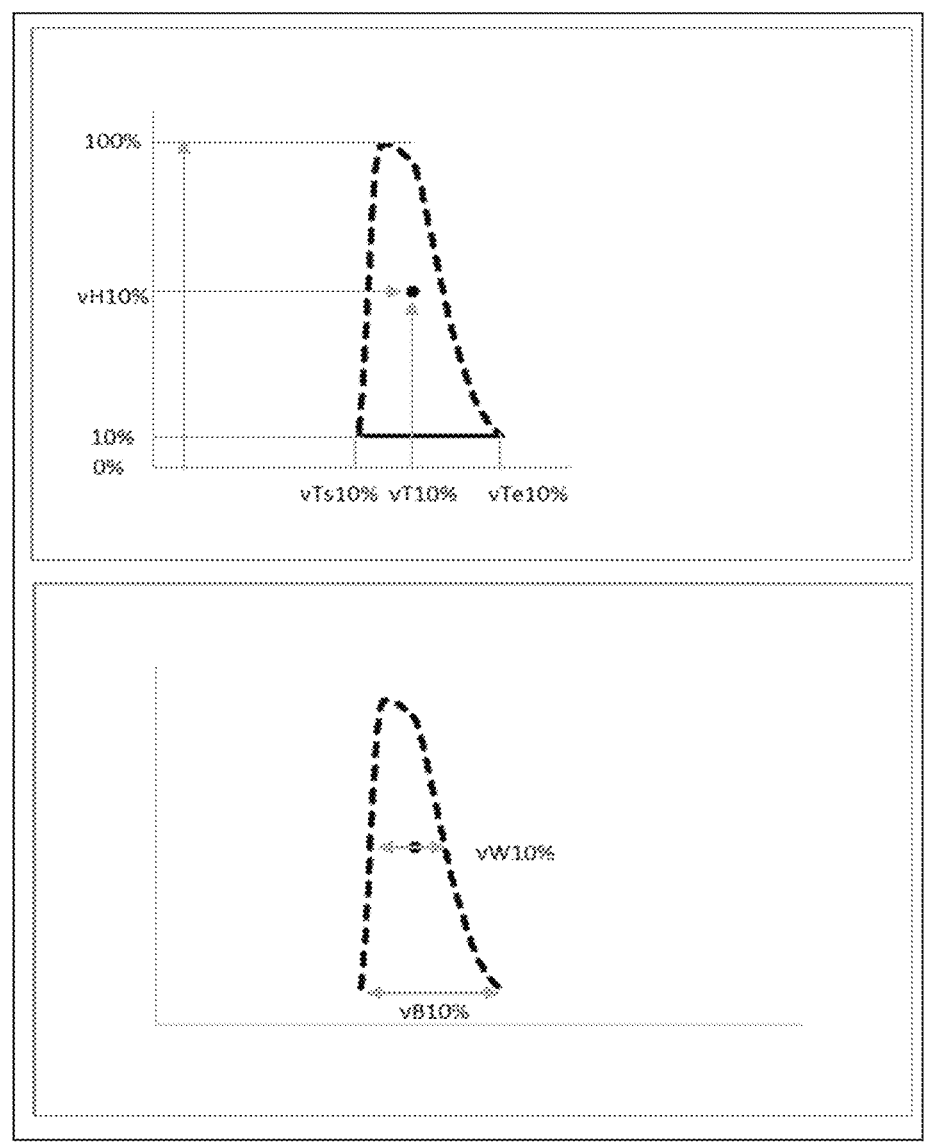
FIG. 12 shows conceptual diagrams for indicating a weighted average point, vTs, vTe, vB, and vW. The dotted line indicates a 10% calculation target area of a primary curve.

As another example of the parameters used in the present invention, a weighted average peak width vW can be included. FIG. 12 shows a calculation target area (dotted line) of the primary curve when the calculation target area level S is 10%. A weighted average point (vi, vH) (black circle), vTs, and vTe are shown in the upper part of FIG. 12, and vB and vW are shown in the lower part of FIG. 12. As shown in FIG. 12, vW is a peak width (time length to be $F(t) \geq vH$ during the time from the minimum time to the maximum time at which $F(t) \geq vH$ is satisfied) at which the primary curve $F(t) \geq vH$ is satisfied. The similar parameters can be calculated also for the uncorrected primary curve. Similarly, for the plus peak of the secondary curve, the peak width at which $F'(t) \geq pH$ is satisfied is defined as the weighted average peak width pW. For the minus peak of the secondary curve, the width of coagulation reaction time at which $F'(t) \leq mH$ is satisfied is defined as the weighted average peak width mW.

Figure 13:
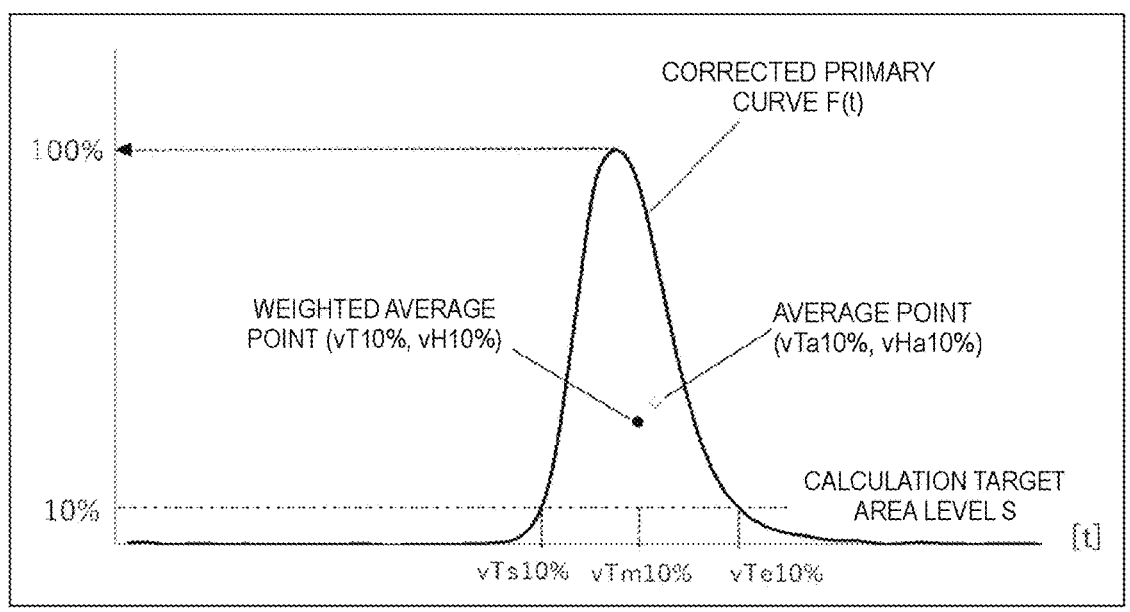
FIG. 13 shows a conceptual diagram for indicating vTa, vHa, and vTm.

Other examples of the parameters used in the present invention include an average time vTa, an average height vHa, and an area median time vTm. FIG. 13 shows an average point (vTa, vHa) (white rhombus), a weighted average point (VT, vH) (black circle), vTs, vTe, and vTm of the primary curve when the calculation target area level S is 10%. vTa, vHa, and vTm are represented by the following formulas, respectively when the number of data points from F(vTs) to F(vTe) is denoted by n.

$$vTa = \frac{\sum_{i=vTs}^{vTe} i}{n} \quad (5)$$

$$vHa = \frac{\sum_{i=vTs}^{vTe} F(i)}{n} \quad (6)$$

$$vTm = \frac{vTs + vTe}{2} \quad (7)$$

Similarly, also for the secondary curve, pTm that is the center point of pTs and pTe, and mTm that is the center point of mTs and mTe can be obtained by referring to the formula (7).

As the parameters for the primary curve used in the present invention, a weighted average height vH, an average height vHa, a peak width vB, and a weighted average peak width vW are used to define flattenings vAB and vABa based on the peak width, and flattenings vAW and vAWa based on the weighted average peak width as the following formulas (8a), (8b), (8c), and (8d), respectively.

$$vAB = vH/vB \quad (8a)$$

$$vAW = vH/vW \quad (8b)$$

$$vABa = vHa/vB \quad (8c)$$

$$vAWa = vHa/vW \quad (8d)$$

Further, as the parameters of the primary curve, a weighted average time vT, a peak width vB, and a weighted average peak width vW are used to define a time rate vTB based on the peak width, and a time rate vTW based on the weighted average peak width as the following formulas (9a), and (9b), respectively $$vTB = vT/vB \quad (9a)$$

$$vTW = vT/vW \quad (9b)$$

In this regard, the flattenings may be vAB=vB/vH, and vAW=vW/vH, or may also be vABa=vB/vHa, and vAWa=vW/vHa. That is, the flattening may be a ratio of the weighted average height vT or the average height vHa to the peak width vB or vW. Similarly, the time rates may be vTB=vB/vT, and vTW=vW/vT. That is, the time rate may be a ratio of the weighted average time vT to the peak width vB or vW. Further, these ratios may be multiplied by a constant K. That is, for example, the flattening may be vAB=(vH/vB) K, vAB=(vB/vH) K, vAW=(vH/vW) K, or vAW=(vW/vH) K, or may also be vABa=(vHa/vB)K, vABa=(vB/vHa)K, vAWa=(vHa/vW)K, or vAWa=(vW/vHa), and the time rate may be vTB=(vT/vB)K, vTB=(vB/vT)K, vTW=(vT/vW)K, or vTW=(vW/vT)K.

In addition, the flattening and time rate as described above can also be determined for a secondary curve. For example, for the plus peak of the secondary curve, as the ratio of pH to pB or pW, the flattening pAB based on the peak width, or the flattening pAW based on the weighted average peak width can be determined, and in addition, as the ratio of pT to pB or pW, the time rate pTB based on the peak width, or the time rate pTW based on the weighted average peak width can be determined. Similarly, for the minus peak of the secondary curve, as the ratio of mH to mB or mW, the flattening mAB based on the peak width, or the flattening mAW based on the weighted average peak width can be determined, and in addition, as the ratio of mT to mB or mW, the time rate mTB based on the peak width, or the time rate mTW based on the weighted average peak width can be determined.

The peak widths vB, pB, and mB, the weighted average peak widths vW, pW, and mW, the average time vTa, the average height vHa, the area start point times vTs, pTs, and mTs, the area end point times vTe, pTe, and mTe, the area median times vTm, pTm, and mTm, the area time width vTr, the main peak start point times vNs, pNs, and mNs, the main peak end point times vNe, pNe, and mNe, the main peak widths vN, pN, and mN, the flattenings vAB, vAW, vABa, vAWa, pAB, pAW, mAB, and mAW, and the time rates vTB, vTW, pTW, pAW, mTB, and mTW, which are as described above, can also be parameters that characterize the calculation target area of the primary curve.

In the present specification, in order to identify the parameters derived from different calculation target areas, each parameter may be expressed with the calculation target area level S from which it is derived. For example, the parameters that characterize the calculation target area of the primary curve when S is x (%) may be referred to as, for example, vHx, vTx, vBx, and vWx. For example, the parameters vH, vT, vB, vW, vTa, vHa, vTs, vTe, vTm, vTr, vNs, vNe, vN, vAB, vAW, vABa, vAWa, vTB, and vTW, which are related to the weighted average point of the primary curve when S is 10%, may be referred to as vH10%, vT10%, vB10%, vW10%, vTa10%, vHa10%, vTs10%, vTe10%, vTm10%, vTr10%, vNs10%, vNe10%, vN10%, vAB10%, vAW10%, vABa10%, vAWa10%, vTB10%, and vTW10%, respectively. The same applies to the parameters that characterize the calculation target area of the secondary curve.

FIGS. 14A and 14B show parameters in the cases where the calculation target area level S is different for the same primary curve. FIG. 14A shows the case where the calculation target area level S is 10%, and FIG. 14B shows the case where the calculation target area level S is 80%. In the case of FIG. 14A where the calculation target area level S is 10%, the weighted average height vH10% of the primary curve is 0.4, the weighted average time vT10% is 149 seconds, and the peak width vB10% is 200 seconds. In addition, in the case of FIG. 14B where the calculation target area level S is 80%, the weighted average height vH80% is 0.72, the weighted average time vT80% is 119 seconds, and the peak width vB80% is 78 seconds.

1.3.3.5. Others

As another example of the parameters that characterize the calculation target area used in the present invention, the area under the curve (AUC) in the calculation target area of the primary or secondary curve can be included. Since the secondary curve has plus and minus peaks, as the area under the curve (AUC) in the calculation target area, there may be an AUC (pAUC) in the calculation target area for the plus peak, and an AUC (mAUC) in the calculation target area of the minus peak. In the present specification, in order to identify an AUC derived from a different calculation target area, the AUC may be referred to as AUCx in accordance with the calculation target area level S from which it is derived. For example, the vAUC, pAUC, and mAUC in the calculation target area when S is 5% are vAUC5%, pAUC5%, and mAUC5%, respectively.

Further, parameters other than the parameters that characterize the above-described calculation target area may be included in the parameters for the determination of the activity level or activity abnormality of a coagulation factor according to the present invention. Examples of the parameters include a maximum primary differential value Vmax, a maximum secondary differential value Amax, a minimum secondary differential value Amin, and VmaxT, AmaxT, and AminT that represent the times to reach them, respectively.

The series of parameters described above may include parameters derived from a coagulation reaction curve (corrected zero-order to secondary curves) with correction treatment, and parameters derived from a coagulation reaction curve (uncorrected zero-order to secondary curves) without correction treatment.

As in the above, the parameters that characterize the waveform related to the coagulation rate or the coagulation acceleration have been described on the basis of the coagulation reaction curve based on the amount of scattered light. In addition, it is obvious to a person skilled in the art that equivalent parameters can be acquired from the coagulation reaction curve based on other coagulation measuring means (for example, amount of transmitted light, or absorbance). For example, in the primary curve F(t) obtained from a coagulation reaction curve that is reverse sigmoid as based on the amount of transmitted light, the positive and negative are reversed for the curve based on the above-described amount of scattered light. In such a case, it is obvious to a person skilled in the art that the signs of F(t) are reversed in the parameter calculation, for example, the maximum value Vmax is replaced with the minimum value Vmin, the calculation target area is an area that satisfies F(t)≤S, vB and vW are time lengths to be F(t)≤x and F(t)≤vH, respectively from t1 to t2.

1.4. Determination of Specimen

One example of the determination performed in step 4 will be described.

1.4.1. Preparation of Parameter Group

As described above, for each of the calculation target areas of the waveform related to the coagulation rate or the coagulation acceleration, parameters that characterize the calculation target area are extracted. Examples of the parameters that characterize the calculation target area include parameters related to the weighted average point of the primary curve (a weighted average time vT, a weighted average height vH, an average time vTa, an average height vHa, a peak width vB, a weighted average peak width vW, flattenings vAB, vAW, vABa, and vAWa determined from them, time rates vTB, and vTW, vAUC, vTs, vTe, vTr, vTm, vNs, vNe, and vN), and parameters related to the weighted average point of the secondary curve (weighted average times pT, and mT, weighted average heights pH, and mH, peak widths pB, and mB, weighted average peak widths pW, and mW, flattenings pAB, pAW, mAB, and mAW determined from them, time rates pTB, pTW, mTB, and mTW, pAUC, mAUC, pNs, pNe, pN, mNs, mNe, mN, pTs, pTe, pTm, mTs, mTe, and mTm), which are shown in Table A to be described later. In the present invention, any one or more of these parameters may be extracted, however, a parameter set containing two or more of these parameters may be extracted. For example, the parameters may be at least one selected from the group consisting of vT, vH, vB, vAB, and vTB, however, may be a parameter set containing two or more of these parameters. In one preferred embodiment, the parameters are a parameter set containing vT, vH, vB, vAB, and vTB. In another preferred embodiment, the parameters are a parameter set containing vB, vAB, and vTB. In another preferred embodiment, the parameters are a parameter set containing vB, and vAB. In another preferred embodiment, the parameter is pH, pAB, or vH. In another preferred embodiment, the parameters are a parameter set of pAB and pNe, a parameter set of pTW and vT, a parameter set of pTB and vABa, a parameter set of pAB and vNs, or a parameter set of pTW, vTs, and vW. In this regard, the constitution of the parameters that characterize each of the calculation target areas used in the method according to the present invention is not limited to these embodiments.

Preferably, the multiple parameters (parameter group) used for the determination of a test specimen in the method according to the present invention include multiple parameters that characterize the multiple calculation target areas, respectively of one waveform. In other words, the parameter group is a set of multiple parameters that are extracted from multiple calculation target areas of one waveform. Preferably, the parameter group includes one or more sets of the same kind of parameters extracted from different calculation target areas of one waveform (primary curve or secondary curve). For example, in a case where L areas of calculation target areas are extracted and the parameter to be adopted is vHx, the parameter group is formed of L pieces of vHx. For example, in a case where 10 areas of calculation target areas based on 10 levels of calculation target area levels S (5%, 10%, 20%, 30%, 40%, 50%, 60%, 70%, 80%, and 90%) are extracted, and a parameter vHx is extracted from each of the calculation target areas, the parameter group is a set of 10 pieces of vHx [vH5%, vH10%, vH20%, vH30%, vH40%, vH50%, vH60%, vH70%, vH80%, and vH90%]. Further, for example, in a case where 5 areas of calculation target areas based on 5 levels of calculation target area levels S (5%, 20%, 40%, 60% and 80%) are extracted, and a parameter vHx is extracted from each of the calculation target areas, the parameter group is a set of 5 pieces of vHx [vH5%, vH20%, vH40%, vH60%, and vH80%]. Similarly, in a case where M areas of calculation target areas are extracted and the parameters to be adopted are vBx, vABx and vTBx, the parameter group is formed of M sets of [vBx, vABx, and vTBx]. Alternatively, in a case where N areas of calculation target areas are extracted and the parameters to be adopted are vTx, vHx, vBx, vABx and vTBx, the parameter group is formed of N sets of [vTx, vHx, vBx, vABx, and vTBx].

Further, multiple parameters that characterize each of the calculation target areas may be combined with other parameters. For example, at least one selected from the group consisting of a maximum primary differential value Vmax, a maximum secondary differential value Amax, a minimum secondary differential value Amin, and VmaxT, AmaxT, and AminT that represent the times to reach them, respectively, which are shown in Table A to be described later, may be combined with the multiple parameters that characterize the above calculation target area.

1.4.2. Target Blood Coagulation Time Prolongation Factor Component

As the blood coagulation time prolongation factor component to be targeted, of which the activity level or activity abnormality is determined by the method according to the present invention, any endogenous or exogenous component involved in coagulation reaction, which causes a prolongation of blood coagulation time, is included. Preferably, the blood coagulation time prolongation factor component to be targeted is a coagulation factor. The coagulation factor is preferably at least one kind selected from coagulation factors including FVIII and FIX, and more preferably at least FVIII. Both of FVIII and FIX may be targeted.

1.4.3. Template Specimen

In the method according to the present invention, a parameter group (hereinafter, also referred to as test parameter group) that includes multiple parameters extracted from multiple calculation target areas of a waveform related to the coagulation rate or coagulation acceleration of the above-described test specimen is compared with a corresponding parameter group (also referred to as template parameter group in the present specification) for a template blood specimen (hereinafter, also simply referred to as template specimen). On the basis of the results of the comparison, coagulation characteristics of the test specimen, preferably the activity level or activity abnormality of a blood coagulation time prolongation factor component in the test specimen is determined. Preferably, in the present invention, one or more of template specimens are prepared. The template specimen is a blood specimen in which the activity level or the presence or absence of activity abnormality, of a blood coagulation time prolongation factor component to be targeted in the method according to the present invention is known.

For example, in a case of evaluating FVIII, the one or more of template specimens include one or more of blood specimens with a non-abnormal FVIII activity level (normal FVIII specimens), and one or more of blood specimens with an abnormal FVIII activity level (abnormal FVIII specimens, for example, FVIII-deficient specimens). For example, in a case of evaluating FIX, the one or more of template specimens include one or more of blood specimens with a non-abnormal FIX activity level (normal FIX specimens), and one or more of blood specimens with an abnormal FIX activity level (abnormal FIX specimens, for example, FIX-deficient specimens). For example, in a case of evaluating FVIII and FIX, the one or more of template specimens include one or more of blood specimens with non-abnormal FVIII and FIX activity levels (normal FVIII/FIX specimens), one or more of blood specimens with an abnormal FVIII activity level (abnormal FVIII specimens, for example, FVIII-deficient specimens), and one or more of blood specimens with an abnormal FIX activity level (abnormal FIX specimens, for example, FIX-deficient specimens).

Preferably, the abnormal FVIII specimens include blood specimens derived from patients with severe, moderate, and mild hemophilia A. Preferably, the blood specimens derived from patients with severe, moderate, and mild hemophilia A are blood specimens having FVIII activities of less than 1%, 1% or more and less than 5%, and 5% or more and less than 40%, respectively (when the activity of normal individual is taken as 100%, the same applies hereinafter). In a case where a more detailed analysis is required, multiple specimens derived from patients with severe hemophilia A having different FVIII activity levels may be prepared as needed. For example, a specimen derived from a patient with Modestly-Severe Haemophilia A (MS-HA) having a FVIII activity of 0.2% or more and less than 1%, and a specimen derived from a patient with Very-Severe Haemophilia A (VS-HA) having a FVIII activity of less than 0.2% may be prepared. In recent years, it has been reported that there is a difference in the clinical severity between a patient with VS-HA having a particularly low FVIII activity (FVIII activity of less than 0.2%) and a patient with MS-HA having no such a low FVIII activity (FVIII activity of 0.2% or more and less than 1%) among the patients with severe hemophilia A (Tomoko Matsumoto, Midori Shima, Clot Waveform Analysis and its Application to the Detection of Very Low Levels of Factor VIII Activity, 2003, Vol. 14, No. 2, pp. 122-127). It is useful to differentiate a patient with VS-HA, for applying an appropriate treatment to a patient.

Similarly, the abnormal FIX specimens preferably include blood specimens derived from patients with severe, moderate, and mild hemophilia B. Preferably, the specimens derived from the patients with severe, moderate, and mild hemophilia B are specimens having FIX activities of less than 1%, 1% or more and less than 5%, and 5% or more and less than 40%, respectively (when the activity of normal individual is taken as 100%, the same applies hereinafter). In a case where a more detailed analysis is performed, multiple specimens derived from patients with severe hemophilia B having different FIX activity levels may be prepared as needed. For example, a specimen having a FIX activity of 0.2% or more and less than 1%, and a specimen having a FIX activity of less than 0.2% may be prepared.

1.4.4. Regression Analysis

In the method according to the present invention, a regression analysis of the corresponding parameters is performed between the test parameter group and the template parameter group derived from each template specimen.

The template parameter group used for the regression analysis is obtained by performing the data analysis described in the above 1.3. for each template specimen. In this data analysis, the number of calculation target areas to be extracted, and a series of calculation target area levels S used for the extraction of multiple calculation target areas are set to the same values as those of the data analysis of the test specimen. Further, the kinds of the parameters included in the template parameter group are the same as those of the test parameter group. For example, if the test parameter group is L pieces of vHx, the template parameter group for the template specimen is also L pieces of vHx. Further, for example, if the test parameter group is M sets of [vBx, vABx, and vTBx], the template parameter group for the template specimen is also M sets of [vBx, vABx, and vTBx]. Furthermore, for example, if the test parameter group is N sets of [vTx, vHx, vBx, vABx, and vTBx], the template parameter group for the template specimen is also N sets of [vTx, vHx, vBx, vABx, and vTBx]. Accordingly, the template parameter group is a parameter group for the template specimen corresponding to the test parameter group. That is, the individual parameters included in each template parameter group correspond to the individual parameters included in the test parameter group mutually. In this regard, in the present specification, in a case where the parameters of the template parameter group correspond to the parameters of the test parameter group, the parameters of the template parameter group and the parameters of the test parameter group are the same kind of parameters. For example, the vTx, vHx, vBx, vABx and vTBx of the test parameter group correspond to the vTx, vHx, vBx, vABx and vTBx (x is a predetermined value) of the template parameter group, respectively. The template parameter group consisting of parameters that correspond to all the parameters of the test parameter group corresponds to the test parameter group.

It is desirable to acquire the template parameter group in advance. Further, each template parameter group may be a synthesis parameter group obtained by processing a parameter group that has been obtained from multiple template specimens. For example, by acquiring parameter groups for multiple template specimens having the same activity levels of a target blood coagulation time prolongation factor component, and statistically processing the parameter groups, one or more of synthesis parameter groups representing standard template specimens may be prepared.

The technique of the regression analysis is not particularly limited, and includes, for example, linear regression by a method of least squares. For example, the value of each parameter in the test parameter group is plotted on the y-axis, and the value of the corresponding parameter in any one template parameter group is plotted on the x-axis to obtain a regression line. The correlation between the test parameter group and the template parameter group is examined on the basis of the tilt of the regression line, the intercept, the correlation (for example, correlation coefficient, or determination coefficient), or the like. The correlation between the test parameter group and the template parameter group reflects the correlation (approximate state) of the coagulation characteristics between the test specimen and the template specimen from which the template parameter group is derived.

1.4.5. Determination of Blood Coagulation Characteristics

Next, on the basis of the results of the regression analysis, the coagulation characteristics in a test specimen are determined. Preferably, the determination of the coagulation characteristics is a determination of the activity level or the activity abnormality, of a blood coagulation time prolongation factor component to be targeted. Hereinafter, the determination procedure will be described by taking the case where the blood coagulation time prolongation factor component to be targeted is FVIII as an example. Other factors such as FIX may be determined by the similar procedure.

On the basis of the correlation between the test specimen determined by the above regression analysis and one or more of the template specimens, the FVIII activity level or activity abnormality (for example, deficiency) of the test specimen is determined. Preferably, the correlation is correlation (for example, tilt, intercept, correlation coefficient, or determination coefficient) of the regression line.

One embodiment of the determination of the FVIII activity level or activity abnormality of a test specimen, based on the correlation will be described below. A template specimen includes one or more of normal FVIII specimens, and one or more of abnormal FVIII specimens having variously different FVIII activity levels. Preferably, the template specimen includes one or more of normal FVIII specimens, and one or more of the abnormal FVIII specimens derived from patients with severe (VS-HA and MS-HA as needed), moderate, and mild hemophilia A. From all of the template specimens used in the regression analysis, at least one specimen with which the correlation between the test parameter group and the template parameter group satisfies predetermined conditions is selected.

In one embodiment, a template specimen with which the correlation is a value of the threshold that has set in advance or more is selected. In another embodiment, a template specimen with which the correlation is a value equal to or more than the threshold that has set in advance and is the highest is selected. In another embodiment, a template specimen with which the tilt of the regression line between the test parameter group and the template parameter group is in a predetermined range (for example, 0.70 or more and 1.30 or less, preferably 0.75 or more and 1.25 or less, more preferably 0.80 or more and 1.20 or less, furthermore preferably 0.85 or more and 1.15 or less, and still more preferably 0.87 or more and 1.13 or less) is selected. In another embodiment, a template specimen with which the tilt of the regression line between the test parameter group and the template parameter group is in the predetermined range and further the correlation coefficient of the regression line is a predetermined value or more (for example, larger than 0.75, preferably larger than 0.80, more preferably larger than 0.85, and furthermore preferably larger than 0.90) is selected. In addition, in a case where a template specimen satisfying the predetermined conditions is not selected, the template specimen may be selected again by changing the predetermined conditions, or such a case may be evaluated as "no template specimen selection".

In one preferred embodiment, a template specimen with which the tilt of the regression line is in a predetermined range (for example, 0.70 or more and 1.30 or less, preferably 0.75 or more and 1.25 or less, more preferably 0.80 or more and 1.20 or less, furthermore preferably 0.85 or more and 1.15 or less, and still more preferably 0.87 or more and 1.13 or less) is selected. Preferably, a template specimen with which the tilt of the regression line is in the predetermined range and further the correlation coefficient of the regression line is a predetermined value or more (for example, larger than 0.75, preferably larger than 0.80, more preferably larger than 0.85, and furthermore preferably larger than 0.90) is selected. From the selected template specimens, a template specimen with which the correlation coefficient of the regression is the highest is selected. In a case where multiple template specimens satisfying the predetermined conditions are selected, one template specimen may be selected on the basis of additional criteria from them.

Next, the state of FVIII (that is, activity level or activity abnormality of FVIII) in the selected template specimen is determined as the state of FVIII in the test specimen. In a case where multiple template specimens are selected, the state of FVIII in the test specimen may be determined to be corresponded to any of the states of the multiple template specimens, or the average state of the multiple template specimens may be determined as the state of FVIII in the test specimen.

For example, if the selected template specimen is a normal FVIII specimen, the state of FVIII in the test specimen can be determined to be not abnormal, and if the selected template specimen is an abnormal FVIII specimen, the test specimen can be determined to have abnormality of the FVIII activity. Further, for example, if the selected template specimens are specimens derived from patients with severe, moderate, and mild hemophilia A, the test specimens can be determined to be severe, moderate, and mild hemophilia A, respectively. In addition, in a case where the template specimens include specimens derived from patients with severe hemophilia A of VS-HA and MS-HA, if the template specimen derived from a patient with VS-HA or MS-HA is selected, the test specimen can be determined to be VS-HA or MS-HA. Alternatively, in a case where the FVIII activity level in the test specimen is determined, the FVIII activity level of the selected template specimen can be determined as the FVIII activity level in the test specimen.

In addition, if the template specimens include specimens derived from patients with severe, moderate, and mild hemophilia A and have "no template specimen selection" in the above evaluation for correlation, it can be determined that the test specimen does "not have the activity abnormality of FVIII", or that "the prolongation factor of the blood coagulation time is not due to the activity abnormality of FVIII" of the test specimen.

In another preferred embodiment, template specimens with each of which the tilt of the regression line is in a predetermined range (for example, 0.70 or more and 1.30 or less, preferably 0.75 or more and 1.25 or less, more preferably 0.80 or more and 1.20 or less, furthermore preferably 0.85 or more and 1.15 or less, and still more preferably 0.87 or more and 1.13 or less) are all selected. Preferably, template specimens with each of which the tilt of the regression line is in the predetermined range and further the correlation coefficient of the regression line is a predetermined value or more (for example, larger than 0.75, preferably larger than 0.80, more preferably larger than 0.85, and furthermore preferably larger than 0.90) are all selected. The state of FVIII (that is, activity level or activity abnormality of FVIII), which is most frequently found in the selected template specimens, is determined as the state of FVIII in the test specimen.

For example, if the number of normal FVIII specimens is the largest among the selected template specimens, the state of FVIII in the test specimen can be determined to be not abnormal. In addition, if the number of abnormal FVIII specimens is the largest among the selected template specimens, the test specimen can be determined to have abnormality of the FVIII activity. Further, for example, when the number of specimens derived from patients with severe, moderate, and mild hemophilia A is the largest among the selected template specimens, the test specimens can be determined to be severe, moderate, and mild hemophilia A, respectively. Further, for example, when the number of specimens derived from patients with severe hemophilia A of VS-HA and MS-HA is the largest among the selected template specimens, the test specimens can be determined to be VS-HA and MS-HA, respectively. Further, for example, when the number of blood coagulation time prolongation specimens with non-abnormal FVIII is the largest among the selected template specimens, the test specimens can be determined to be abnormal specimens other than the specimens derived from patients with (severe, moderate, and mild) hemophilia A. Alternatively, in a case where the FVIII activity level in the test specimen is determined, the FVIII activity level that is most frequently found in the selected template specimens can be determined as the FVIII activity level in the test specimen.

In another preferred embodiment, template specimens with each of which the tilt of the regression line is in a predetermined range (for example, 0.70 or more and 1.30 or less, preferably 0.75 or more and 1.25 or less, more preferably 0.80 or more and 1.20 or less, furthermore preferably 0.85 or more and 1.15 or less, and still more preferably 0.87 or more and 1.13 or less) are all selected. Preferably, template specimens with each of which the tilt of the regression line is in the predetermined range and further the correlation coefficient of the regression line is a predetermined value or more (for example, larger than 0.75, preferably larger than 0.80, more preferably larger than 0.85, and furthermore preferably larger than 0.90) are all selected.

The selected template specimens are classified into specimens derived from patients with (severe, moderate, and mild) hemophilia A having a low FVIII activity and other specimens, in accordance with the FVIII activity level. In a case where the number of the former is larger than the number of the latter, the severity (either one of severe, moderate, or mild) that is most frequently found among the former specimens is determined as the state of the test specimen. In a case where the same number of specimens with different severities are present, a more severe severity may be determined as the state of the test specimen, or the template specimen may be selected again by changing the predetermined conditions. On the other hand, in a case where the number of the latter is larger than the number of the former, the test specimen can be determined to be a specimen other than those of patients with (severe, moderate, and mild) hemophilia A.

As described above, the FVIII activity level or the presence or absence of the activity abnormality, in the test specimen can be determined by the method according to the present invention. In another embodiment, the presence or absence of the activity abnormality of FVIII in the test specimen is determined, and the determination provides the information about the determination of whether or not the test specimen is a specimen of a patient with hemophilia A.

In another embodiment, the FVIII activity level in the test specimen is determined, and the determination provides the information about the determination of the severity of hemophilia A in a patient who has provided the test specimen. Therefore, one embodiment of the method for analyzing a blood specimen according to the present invention can be a method for, for example, determining hemophilia A, and determining the severity of hemophilia A such as severe (VS-HA or MS-HA if necessary), moderate, or mild.

In one embodiment, in addition to the above determination on FVIII, the determination on other blood coagulation time prolongation factor components may be performed for the test specimen. Preferably, one of other blood coagulation time prolongation factor components is FIX. For example, for the test specimen that has been determined that "the prolongation factor of the blood coagulation time is not due to the activity abnormality of FVIII" or determined to be "other than those of patients with (severe, moderate, and mild) hemophilia A" in the above determination on FVIII, the activity level or the presence or absence of the activity abnormality, of FIX may be determined. The determination procedure of the activity level or the presence or absence of the activity abnormality, of FIX can be performed by a procedure similar to the above-described determination procedure for FVIII. The template specimens used for the determination of the FIX may be the same as or different from those used in the evaluation for FVIII. Further, the test parameter group and template parameter group used for the determination on FIX may be the same as or different from those used in the determination on FVIII. In one example of the present embodiments, the presence or absence of the activity abnormality of FIX in the test specimen is determined, and the determination provides the information about the determination of whether or not the test specimen is a specimen of a patient with hemophilia B. In another example of the present embodiments, the FIX activity level in the test specimen is determined, and the determination provides the information about the determination of the severity of hemophilia B in a patient who has provided the test specimen. The present embodiment enables the determination of hemophilia B, and the determination of the severity (for example, severe, moderate, or mild) of hemophilia B. In addition, by combining the evaluation for FVIII with the evaluation for FIX, which has been described above, the coagulation characteristics in the test specimen can be analyzed more comprehensively.

2. Program and Apparatus for the Method According to the Present Invention

The above-described method for analyzing a blood specimen according to the present invention can be performed automatically by using a computer program. Accordingly, one embodiment of the present invention is a program for performing the above-described method for analyzing a blood specimen according to the present invention. Further, a series of steps of the above-described method according to the present invention, including preparation of a sample from a test specimen and measurement of coagulation time can be performed automatically by an automatic analyzer. Therefore, one embodiment of the present invention is an apparatus for performing the above-described method for analyzing a blood specimen according to the present invention.

Figure 15:
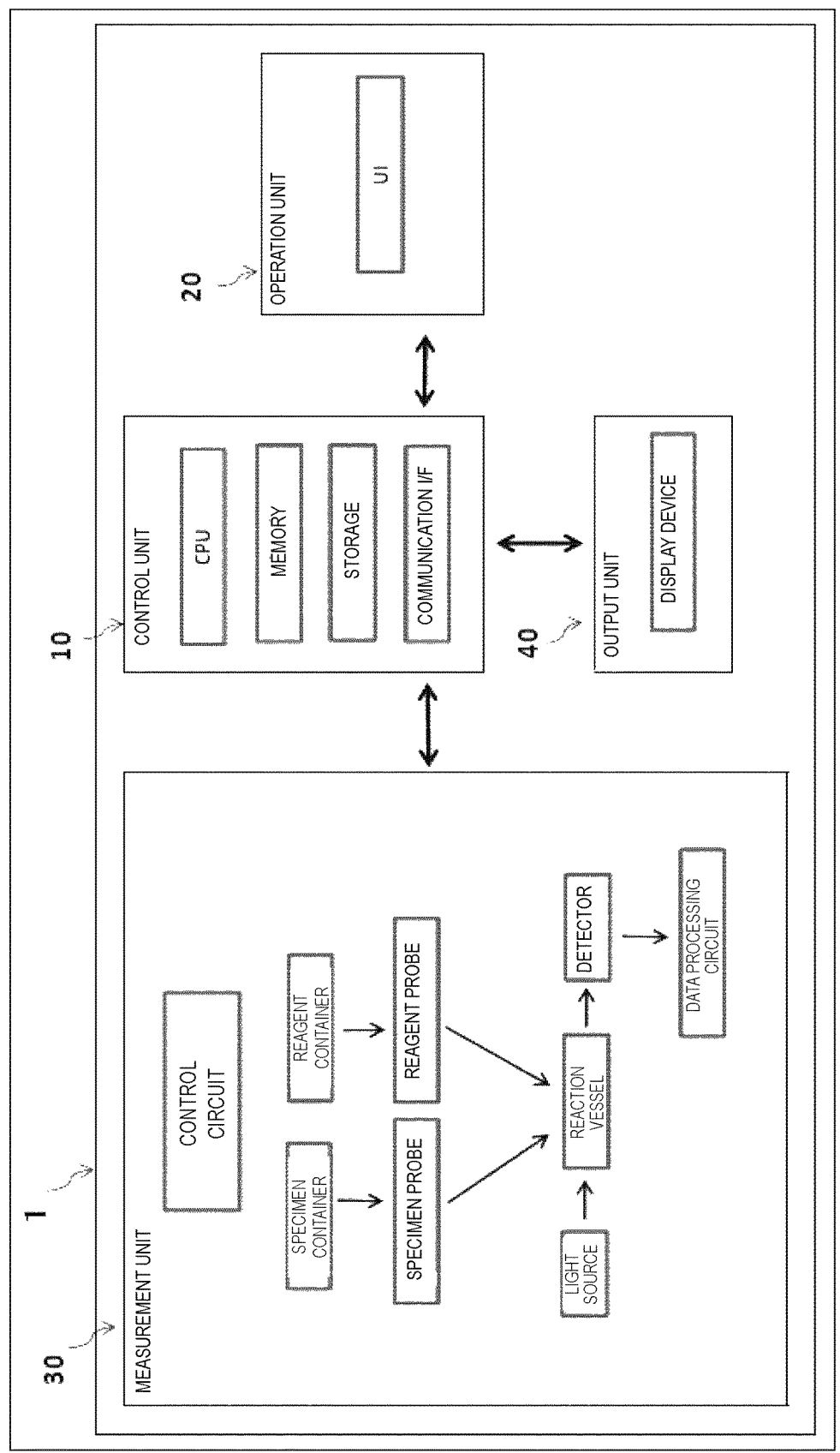
FIG. 15 shows a conceptual diagram for illustrating a configuration of an automatic analyzer for conducting the method for analyzing a blood specimen according to the present invention.

One embodiment of the apparatus according to the present invention will be described below. One embodiment of the apparatus according to the present invention is an automatic analyzer 1 as shown in FIG. 15. The automatic analyzer 1 includes a control unit 10, an operation unit 20, a measurement unit 30, and an output unit 40.

The control unit 10 controls the overall operations of the automatic analyzer 1. The control unit 10 can be configured by, for example, a personal computer (PC). The control unit 10 includes, for example, a central processing unit (CPU), a memory, a storage, and a communication interface (I/F), and performs, for example, processing of commands from the operation unit 20, control of operation of the measurement unit 30, storage and data analysis of measurement data received from the measurement unit 30, storage of the analysis results, and control of output of the measurement data and the analysis results by the output unit 40. Further, the control unit 10 may be connected to other devices such as an external medium, and a host computer. In this regard, in the control unit 10, the PC that controls the operation of the measurement unit 30 and the PC that analyzes the measurement data may be the same or different.

The operation unit 20 acquires input from an operator, and transmits the obtained input information to the control unit 10. For example, the operation unit 20 includes a user interface (UI) such as a keyboard, and a touch panel. The output unit 40 outputs the measurement data of the measurement unit 30, and the analysis results of the data under the control of the control unit 10. For example, the output unit 40 includes a display device such as a display.

The measurement unit 30 performs a series of operations for the blood coagulation test, and acquires measurement data of coagulation reaction of a sample containing a blood specimen. The measurement unit 30 includes various kinds of equipment and analysis modules, which are required for a blood coagulation test, for example, a specimen container for storing a blood specimen, a reagent container for storing a test reagent, a reaction vessel for reaction of a specimen with a reagent, a probe for dispensing a blood specimen and a reagent into the reaction vessel, a light source, a detector for detecting scattered light or transmitted light from a sample in the reaction vessel, a data processing circuit for sending data from the detector to the control unit 10, and a control circuit for controlling operation of the measurement unit 30 in response to a command from the control unit 10.

The control unit 10 performs the analysis of coagulation characteristics of a specimen on the basis of the data measured by the measurement unit 30. The present analysis can include, for example, acquisition of the above-described coagulation reaction curve, and a waveform related to the coagulation rate or the coagulation acceleration, extraction of a parameter group for a test specimen, extraction of a template parameter group for a template specimen, regression analysis of the parameter groups, and determination of the activity level or activity abnormality of a blood coagulation time prolongation factor component to be targeted in the test specimen based on the results of the regression analysis. The present analysis can be performed by a program for performing the method according to the present invention. Accordingly, the control unit 10 can include a program for performing the method according to the present invention.

In the analysis in the above-described control unit 10, the coagulation reaction curve, and the waveform related to the coagulation rate or the coagulation acceleration, which are used in the analysis, may be prepared in the control unit 10 on the basis of the measurement data from the measurement unit 30, or may be prepared by another device, for example, the measurement unit 30, and sent to the control unit 10. Alternatively, the coagulation reaction curve may be prepared in the measurement unit 30, and sent to the control unit 10, and the waveform related to the coagulation rate or the coagulation acceleration may be prepared in the control unit 10. The data of the template parameter group for a template specimen may be prepared by measuring the template specimen in advance in the measurement unit 30, and analyzing the obtained measurement data in the control unit 10, or may be taken in from the outside. The data of the template parameter group can be stored in a memory of the control unit 10 or an external device. The technique of the regression analysis, and the determination criteria for analyzing the coagulation characteristics of the test specimen based on the results of the regression analysis can be controlled by the program according to the present invention.

The analysis results in the control unit 10 are sent to the output unit 40, and output. The output can take any form of, for example, display on a screen, transmission to a host computer, or printing. The output information from the output unit includes the determination results of a blood coagulation time prolongation factor component to be targeted in a test specimen (determination results of, for example, FVIII activity level, hemophilia A, or the severity of hemophilia A), and, if desired, may include additional information such as results (for example, regression line equation, and correlation) of the regression analysis of a test specimen and a template specimen, a coagulation reaction curve of the test specimen or the template specimen, or a waveform related to the coagulation rate or the coagulation acceleration. The kind of the output information from the output unit can be controlled by the program according to the present invention.

In one embodiment, except that a program for performing the method according to the present invention is included, an automatic analyzer 1 can have a configuration of a common automatic analyzer for blood coagulation test as conventionally used for measuring a blood coagulation time such as APTT, or PT.

EXAMPLES

Hereinafter, the present invention will be described in more detail by way of Examples, however, the present invention is not limited to the following Examples.

Unless otherwise specified, the parameters used in the following Examples represent parameters derived from corrected zero-order to secondary curves. In addition, the parameters derived from uncorrected zero-order to secondary curves are represented by adding R to the beginning of the name of each parameter. For example, when the weighted average height of a corrected primary curve is vH, the weighted average height of the uncorrected primary curve is represented by RvH, and when the weighted average height of a corrected secondary curve is pH, the weighted average height of the uncorrected secondary curve is represented by RpH. A list of parameters is shown in the following Table A.

TABLE A

| | | Secondary curve (plus peak) | Secondary curve (minus peak) |
|---|---|---|---|
| | Primary curve | | |
| Waveform parameters of primary and secondary curves | | | |
| Maximum primary differential value | | Vmax (vH100%) | — | — |
| Maximum primary differential value time | | VmaxT (vT100%) | — | — |
| Maximum/minimum secondary differential value | — | Amax (pH100%) | Amin (mH100%) |
| Maximum/minimum secondary differential value time | — | AmaxT (pT100%) | AminT (mT100%) |
| Peak width (time) | Bx | vBx | pBx | mBx |
| Weighted average height | Hx | vHx | pHx | mHx |
| Weighted average time | Tx | vTx | pTx | mTx |
| Weighted average peak width (time) | Wx | vWx | pWx | mWx |
| Average height | Hax | vHax | — | — |
| Average time | Tax | vTax | — | — |
| Main peak width (time) | Nx | vNx | pNx | mNx |
| Area below peak | AUCx | vAUCx | pAUCx | mAUCx |
| Area start point time | Tsx | vTsx | pTsx | mTsx |
| Area end point time | Tex | vTex | pTex | mTex |
| Area median time | Tmx | vTmx | pTmx | mTmx |
| Area time width (time) | Trx | vTrx | — | — |
| Main peak start point time | Nsx | vNsx | pNsx | mNsx |
| Main peak end point time | Nex | vNex | pNex | mNex |
| B flattening | (Hx/Bx)*k | vABx | pABx | mABx |
| W flattening | (Hx/Wx)*k | vAWx | pAWx | mAWx |
| B flattening | (Hax/Bx)*k | vABax | | |
| W flattening | (Hax/Wx)*k | vAWax | | |
| B time rate | (Tx/Bx)*k | vTBx | pTBx | mTBx |
| W time rate | (Tx/Wx)*k | vTWx | pTWx | mTWx | x: Calculation target area level,
k: Constant
Parameters derived from a coagulation reaction curve without correction treatment has "R" in the beginning of the name.

Example 1: Calculation of Test Parameters (1) Method

As a reagent for measurement, Coagpia APTT-N (manufactured by Sekisui Medical Co., Ltd.) being a reagent for APTT measurement was used, and as a calcium chloride solution, a calcium chloride solution, Coagpia APTT-N (manufactured by Sekisui Medical Co., Ltd.) was used. The coagulation reaction measurement of a sample containing a specimen was performed by using a blood coagulation automatic analyzer, CP3000 (manufactured by Sekisui Medical Co., Ltd.). In a cuvette, 50 µL of a reagent for measurement at around 37° C. was added into 50 µL of the specimen heated at 37° C. for 45 seconds, and into the mixture after the lapse of 171 seconds, 50 µL of a 25 mM calcium chloride solution was added to initiate the coagulation reaction. The reaction was performed at 37° C. In the measurement of the coagulation reaction, the cuvette was irradiated with light having a wavelength of 660 nm using a light-emitting diode (LED) as a light source, and the amount of scattered light of 90-degree side scattered light was measured at 0.1-second intervals. The measurement time was set to 360 seconds. A coagulation reaction curve was obtained from the obtained measurement data over time.

(2) Subject Blood Specimen 34 specimens (blood plasma) were analyzed. the 34 specimens include 24 FVIII-deficient specimens (13 specimens of severe severity (FVIII<1%), 8 specimens of moderate severity (FVIII=1 to 5%), and 3 specimens of mild severity (FVIII=5 to 40%)), and 10 specimens (other) other than the FVIII-deficient specimens. In accordance with the procedure of (1), a coagulation reaction curve for each specimen was obtained.

(3) Template Specimen

Constitution of the template specimens used in the analysis is shown in Table 1. 43 specimens having different FVIII activities, and 88 specimens each having a normal FVIII activity but a prolonged blood coagulation time due to other factors were prepared. The FVIII activity of each of the former 43 specimens belongs to any one of severe hemophilia A (FVIII<1%), moderate hemophilia A (FVIII=1 to 5%), mild hemophilia A (FVIII=5 to 40%), and Other (FVIII>40%). The latter 88 specimens belong to "Other" in the classification of Table 1 because the FVIII activity is normal. These 131 specimens in total were used in analysis as template specimens, and a coagulation reaction curve for each specimen was obtained in accordance with the procedure of (1).

TABLE

| | Number of specimens | FVIII <1% | FVIII 1-5% | FVIII 5-40% | Other |
|---|---|---|---|---|---|
| Constitution of template specimen | | | | | |
| Specimen with different FVIII activity | 43 | 11 | 11 | 15 | 6 |
| Specimen with other factors | 88 | — | — | — | 88 |
| Total | 131 | 11 | 11 | 15 | 94 |

Specimen with other factors: deficiency of a coagulation factor other than FVIII, heparinized plasma, and LA-positive plasma (4) Data Analysis
(4-1) Calculation of Primary Curve A corrected primary curve was calculated from the coagulation reaction curve derived from a test specimen, which was obtained in (2). First, the coagulation reaction curve was pretreated. That is, a smoothing treatment including noise removal was performed for the coagulation reaction curve, and the amount of scattered light at the starting point of the measurement was adjusted to 0. Subsequently, the maximum height of the coagulation reaction curve was corrected so as to be 100, and the obtained corrected coagulation reaction curve (corrected zero-order curve) was primarily differentiated to calculate a corrected primary curve.

(4-2) Preparation of Test Parameter Group
(Parameter group A)

From the obtained corrected primary curve, 10 areas of calculation target areas were extracted. The calculation target area levels S were set to 5%, 10%, 20%, 30%, 40%, 50%, 60%, 70%, 80%, and 90%, respectively with respect to the maximum height value Vmax (100%) of the corrected primary curve. For the calculation target area in each S, the peak width vB, and by using the above-described formulas (2), (3), and (4), the weighted average time vT and the weighted average height vH were calculated. From the determined vT and vH, the flattening vAB and the time rate vTB were calculated by the following formulas.

$$vAB = (vH/vB)K_1 (K_1=100)$$

$$vTB = (vT/vB)K_2 (K_2=1)$$

With the above procedure, for 10 areas of calculation target areas (S=5%, 10%, 20%, 30%, 40%, 50%, 60%, 70%, 80%, and 90%), parameters: vB [vB5%, vB10%, vB20%, vB30%, vB40%, vB50%, vB60%, vB70%, vB80%, and vB90%], vT [vT5%, vT10%, vT20%, vT30%, vT40%, vT50%, vT60%, vT70%, vT80%, and vT90%], vH [vH5%, vH10%, vH20%, vH30%, vH40%, vH50%, vH60%, v1470%, vH80%, and vH90%], vAB [vAB5%, vAB10%, vAB20%, vAB30%, vAB40%, vAB50%, vAB60%, vAB70%, vAB80%, and vAB90%], and vTB [vTB5%, vTB10%, vTB20%, vTB30%, vTB40%, vTB50%, vTB60%, vTB70%, vTB80%, and vTB90%] were calculated.

By the combination of the calculated parameters for a test specimen, test parameter groups were prepared as follows:

(Parameter group A-1) a parameter group consisting of 50 parameters of vB [vB5%, vB10%, . . . , and vB90%], vT [vT5%, vT10%, . . . , and vT90%], vH [vH5%, vH10%, . . . , and vH90%], vAB [vAB5%, vAB10%, . . . , and vAB90%], and vTB [vTB5%, vTB10%, . . . , and vTB90%];

(Parameter group A-2) a parameter group consisting of 30 parameters of vB [vB5%, vB10%, . . . , and vB90%], vAB [vAB5%, vAB10%, . . . , and vAB90%], and vTB [vTB5%, vTB10%, . . . , and vTB90%]; and (Parameter group A-3) a parameter group consisting of 20 parameters of vB [vB5%, vB10%, . . . , and vB90%], and vAB [vAB5%, vAB10%, . . . , and vAB90%].

For comparison, the maximum value (Vmax) of a curve obtained by differentiating the corrected zero-order curve once and the time (VmaxT) to reach the maximum value, and the maximum value (Amax) of a curve obtained by differentiating the corrected zero-order curve twice and the time (AmaxT) to reach the maximum value were calculated. These are parameters similar to the parameters used in a waveform analysis on a conventional coagulation reaction curve (see Patent Literatures 1 and 2). In addition to these conventional parameters, test parameter groups were prepared as follows:

(Parameter group A-4) a parameter group consisting of 54 parameters of Vmax, Amax, VmaxT, and AmaxT in addition to the parameters of the parameter A-1; and (Comparison parameter group 1) a parameter group consisting of 4 parameters of Vmax, Amax, VmaxT, and AmaxT.

(Parameter Group B)

Further, by using vB, vT, vH, vAB, and vTB for 5 areas of calculation target areas (S=5%, 20%, 40%, 60%, and 80%), test parameter groups were prepared as follows:

(Parameter group B-1) a parameter group consisting of 25 parameters of vB [vB5%, vB20%, vB40%, vB60%, and vB80%], vT [vT5%, vT20%, vT40%, vT60%, and vT80%], vH [vH5%, vH20%, vH40%, vH60%, and vH80%], vAB [vAB5%, vAB20%, vAB40%, vAB60%, and vAB80%], and vTB [vTB5%, vTB20%, vTB40%, vTB60%, and vTB80%];

(Parameter group B-2) a parameter group consisting of 15 parameters of vB [vB5%, vB20%, vB40%, vB60%, and vB80%], [vAB5%, vAB20%, vAB40%, vAB60%, and vAB80%], and vTB [vTB5%, vTB20%, vTB40%, vTB60%, and vTB80%];

(Parameter group B-3) a parameter group consisting of 10 parameters of vB [vB5%, vB20%, vB40%, vB60%, and vB80%], and vAB [vAB5%, vAB20%, vAB40%, vAB60%, and vAB80%]; and (Parameter group B-4) a parameter group consisting of 29 parameters of Vmax, Amax, VmaxT, and AmaxT in addition to the parameters of the parameter B-1.

(4-3) Analysis of Template Specimen

In accordance with the procedures of (4-1) to (4-2), a corrected primary curve was calculated from the coagulation reaction curve derived from each template specimen obtained in (3), and then the above-described parameter groups A-1 to A-4 and B-1 to B-4, the template parameter groups A-1 to A-4 and B-1 to B-4 each having the constitution of the comparison parameter group 1, and a comparison template parameter group 1 were prepared.

The constitution details of the prepared parameter groups are shown in Table 2.

TABLE 2

Constitution of each parameter group used in analysis

| | | Parameter group A ○ | | Parameter group B • | |
|---|---|---|---|---|---|
| | | A-1/B-1 | A-2/B-2 | A-3/B-3 | A-4/B-4 | Comparison |
| | | (vH, vT, vB, vAB, vTB) | (vB, vAB, vTB) | (vB, vAB) | (all) | (conventional) |
| Conventional parameter | VmaxT | | | | ○ • | ○ |
| | Vmax | | | | ○ • | ○ |
| | AmaxT | | | | ○ • | ○ |
| | Amax | | | | ○ • | ○ |

TABLE 2-continued

Constitution of each parameter group used in analysis

| | | Parameter group A ○ | | | | Parameter group B • | |
|---|---|---|---|---|---|---|---|
| | | A-1/B-1 (vH, vT, vB, vAB, vTB) | A-2/B-2 (vB, vAB, vTB) | A-3/B-3 (vB, vAB) | A-4/B-4 (all) | | Comparison (conventional) |
| Weighted average time vT | 5% | ○ • | | | ○ • | | |
| | 10% | ○ | | | ○ | | |
| | 20% | ○ • | | | ○ • | | |
| | 30% | ○ | | | ○ | | |
| | 40% | ○ • | | | ○ • | | |
| | 50% | ○ | | | ○ | | |
| | 60% | ○ • | | | ○ • | | |
| | 70% | ○ | | | ○ | | |
| | 80% | ○ • | | | ○ • | | |
| | 90% | ○ | | | ○ | | |
| Weighted average height vH | 5% | ○ • | | | ○ • | | |
| | 10% | ○ | | | ○ | | |
| | 20% | ○ • | | | ○ • | | |
| | 30% | ○ | | | ○ | | |
| | 40% | ○ • | | | ○ • | | |
| | 50% | ○ | | | ○ | | |
| | 60% | ○ • | | | ○ • | | |
| | 70% | ○ | | | ○ | | |
| | 80% | ○ • | | | ○ • | | |
| | 90% | ○ | | | ○ | | |
| Peak width vB | 5% | ○ • | ○ • | ○ • | ○ • | | |
| | 10% | ○ | ○ | ○ | ○ | | |
| | 20% | ○ • | ○ • | ○ • | ○ • | | |
| | 30% | ○ | ○ | ○ | ○ | | |
| | 40% | ○ • | ○ • | ○ • | ○ • | | |
| | 50% | ○ | ○ | ○ | ○ | | |
| | 60% | ○ • | ○ • | ○ • | ○ • | | |
| | 70% | ○ | ○ | ○ | ○ | | |
| | 80% | ○ • | ○ • | ○ • | ○ • | | |
| | 90% | ○ | ○ | ○ | ○ | | |
| Flattening vAB | 5% | ○ • | ○ • | ○ • | ○ • | | |
| | 10% | ○ | ○ | ○ | ○ | | |
| | 20% | ○ • | ○ • | ○ • | ○ • | | |
| | 30% | ○ | ○ | ○ | ○ | | |
| | 40% | ○ • | ○ • | ○ • | ○ • | | |
| | 50% | ○ | ○ | ○ | ○ | | |
| | 60% | ○ • | ○ • | ○ • | ○ • | | |
| | 70% | ○ | ○ | ○ | ○ | | |
| | 80% | ○ • | ○ • | ○ • | ○ • | | |
| | 90% | ○ | ○ | ○ | ○ | | |
| Time rate vTB | 5% | ○ • | ○ • | | ○ • | | |
| | 10% | ○ | ○ | | ○ | | |
| | 20% | ○ • | ○ • | | ○ • | | |
| | 30% | ○ | ○ | | ○ | | |
| | 40% | ○ • | ○ • | | ○ • | | |
| | 50% | ○ | ○ | | ○ | | |
| | 60% | ○ • | ○ • | | ○ • | | |
| | 70% | ○ | ○ | | ○ | | |
| | 80% | ○ • | ○ • | | ○ • | | |
| | 90% | ○ | ○ | | ○ | | |

Figure 16:
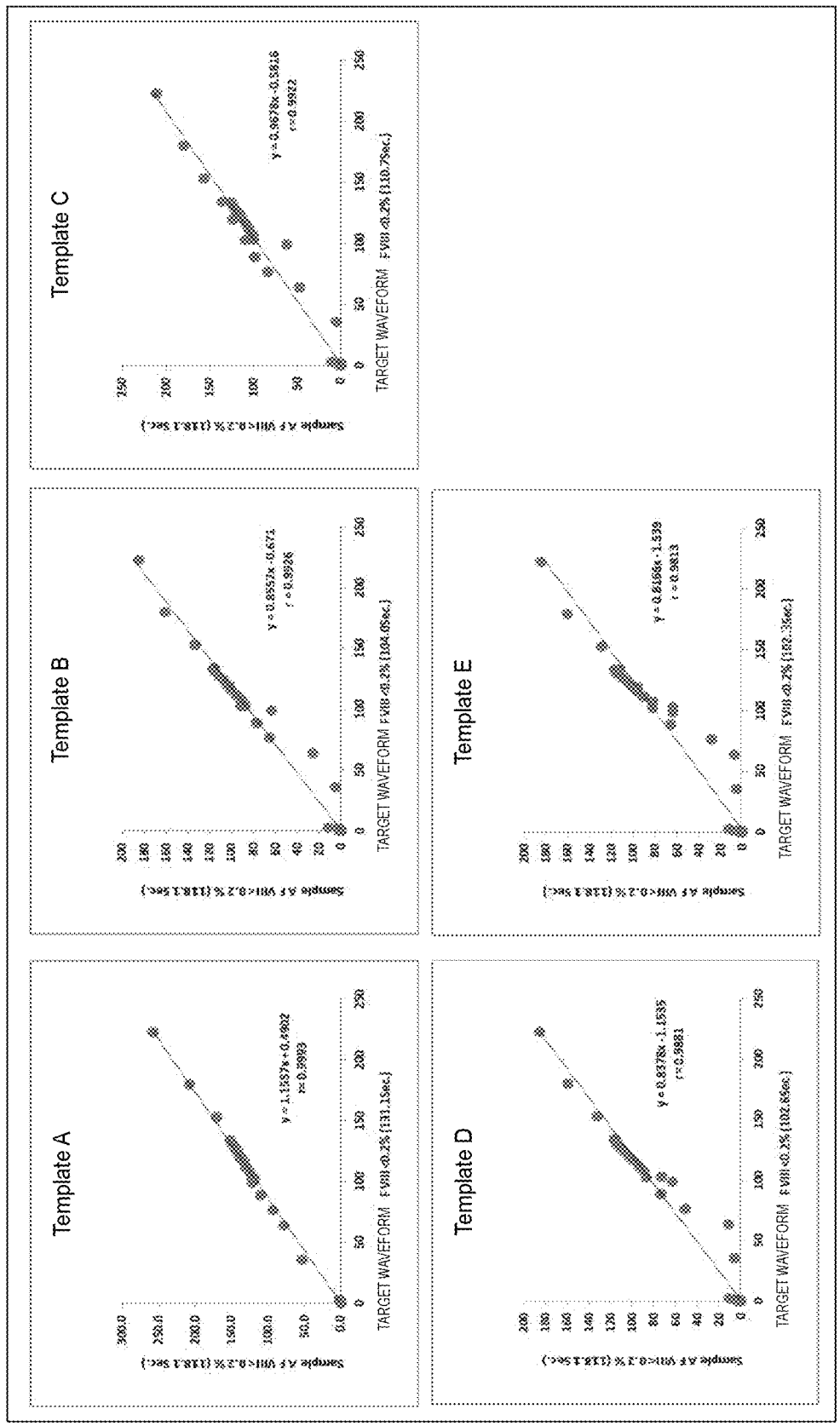
FIG. 16 shows regression lines for a parameter group A-1. The test specimen (Sample AF) is derived from a patient with severe hemophilia A having a FVIII activity of less than 0.2°. In each diagram, the FVIII activity and APTT of template and test specimens are shown on the horizontal axis and the vertical axis, respectively.

Example 2: Determination of FVIII Activity or Abnormality of Test Specimen Using Parameter Group (1) Determination of FVIII Activity A regression analysis was performed between the test parameter group obtained from a test specimen, and the corresponding template parameter group obtained from each template specimen. As the parameter group, a parameter group A-I acquired in example 1 was used. FIG. 16 shows the results of the top 5 cases in descending order of the correlation coefficient among the results of regression analysis with a test specimen derived from a patient with severe hemophilia a (VS-HA) having a FVIII activity of less than 0.2% (sample AF, APTT: 118.1 seconds, and FVIII<0.2%).

Further, the labels on the horizontal axis and the vertical axis of each diagram in FIG. 16 indicate the FVIII activity and APTT of template and test specimens, respectively. Since the correlation coefficient of these 5 cases was 0.98 or more, the presence of a template specimen having a high correlation with respect to the parameter group with the test specimen sample AF was confirmed. In addition, it was confirmed that the 5 selected template specimens (templates A to E) are all specimens derived from patients with VS-HA having a FVIII activity of less than 0.2%.

FIG. 17A shows a regression line with the specimen (Template A) having the highest correlation coefficient in FIG. 16. FIG. 17B shows corrected primary curves of the test specimen (Sample AF) and Template A. The corrected primary curves of the test specimen (Sample AF) and Template A have extremely similar shapes, and it was indicated that the blood coagulation characteristics of both specimens were similar. From these results, it was revealed that the present analysis was able to be used for the determination of the FVIII activity in a blood specimen. Further, it was revealed that the present analysis was effective also in the detection of a specimen of a patient with VS-HA.

(2) Determination of Severity of Hemophilia A

For each of the parameter groups A-1 to A-4 and B-1 to B-4, and the comparison parameter group 1, acquired in Example 1, the regression analysis was performed between 34 test specimens and each template specimen. Linear regression equations for a parameter group were determined between the test specimen and all the template specimens, and template specimens having a tilt of the regression line in the range of from 0.87 to 1.13 were selected from them. Next, a template specimen having the highest correlation coefficient was selected as the template specimen having the highest correlation from the selected template specimens. The FVIII activity of the selected template specimen was determined as the FVIII activity of the test specimen. On the basis of the determination results, the FVIII activity level of a test specimen was classified into 4 stages (FVIII activities: <1%, 1 to 5%, 5 to 40%, and Other). From the classified FVIII activity level of a test specimen and the actual FVIII activity level of the test specimen determined by a coagulation one-step method, the FVIII activity level concordance rate and the FVIII-deficient concordance rate in the present determination were calculated by the following formulas. The FVIII activity level concordance rate indicates a ratio at which the FVIII activity level of a test specimen by determination was matched with the actual FVIII activity level of the test specimen, and the FVIII-deficient concordance rate indicates a ratio at which the presence or absence of FVIII deficiency of a test specimen by determination was matched with the actual presence or absence of FVIII deficiency of the test specimen.

FVIII activity level concordance rate (%)=($A11+A22+A33+A44$)/$D$×100

FVIII-deficient concordance rate($go$)=($A11+A12+A13+A21+A22+A23+A31+A32+A33+A44$)/$D$×100  [Chemical formula 1]

|  |  | FVIII activity level (determined) | | | | |
|---|---|---|---|---|---|---|
|  |  | <1% | 1-5% | 5-40% | Other | Total |
| FVIII activity level (actually measured) | <1% | A11 | A12 | A13 | A14 | B1 |
|  | 1-5% | A21 | A22 | A23 | A24 | B2 |
|  | 5-40% | A31 | A32 | A33 | A34 | B3 |
|  | Other | A41 | A42 | A43 | A44 | B4 |
|  | Total | C1 | C2 | C3 | C4 | D |

Tables 3 to 5 are comparison tables between the determined FVIII activity of a test specimen and the actual FVIII activity of the test specimen. Comparison tables in a case where parameter groups A-1 to A-4 were used are shown in Table 3, comparison tables in a case where parameter groups B-1 to B-4 were used are shown in Table 4, and a comparison table in a case where a comparison parameter group 1 was used is shown in Table 5.

TABLE 3

Analysis results using parameter group A-1

|  |  | FVIII activity level (determined) | | | | FVIII activity level concordance rate (%) | | | |
|---|---|---|---|---|---|---|---|---|---|
|  |  | <1% | 1-5% | 5-40% | Other | Concordance | Discordance | Total | Concordance rate |
| FVIII activity level (actually measured) | <1% | 12 | 1 |  |  | 12 | 1 | 13 | 92.3 |
|  | 1-5% |  | 4 | 3 | 1 | 4 | 4 | 8 | 50.0 |
|  | 5-40% |  | 1 | 2 |  | 2 | 1 | 3 | 66.7 |
|  | Other |  |  |  | 10 | 10 | 0 | 10 | 100.0 |
|  | Total | 12 | 6 | 5 | 11 | 28 | 6 | 34 | 82.4 |

FVIII-deficient concordance rate = 97.1% (33 out of 34 specimens)

Analysis results using parameter group A-2

|  |  | FVIII activity level (determined) | | | | FVIII activity level concordance rate (%) | | | |
|---|---|---|---|---|---|---|---|---|---|
|  |  | <1% | 1-5% | 5-40% | Other | Concordance | Discordance | Total | Concordance rate |
| FVIII activity level (actually measured) | <1% | 12 |  |  | 1 | 12 | 1 | 13 | 92.3 |
|  | 1-5% |  | 6 | 1 | 1 | 6 | 2 | 8 | 75.0 |
|  | 5-40% |  |  | 2 | 1 | 2 | 1 | 3 | 66.7 |
|  | Other |  |  | 1 | 9 | 9 | 1 | 10 | 90.0 |
|  | Total | 12 | 6 | 4 | 12 | 29 | 5 | 34 | 85.3 |

FVIII-deficient concordance rate = 88.2% (30 out of 34 specimens)

TABLE 3-continued

Analysis results using parameter group A-3

|  |  | FVIII activity level (determined) | | | | FVIII activity level concordance rate (%) | | | |
|---|---|---|---|---|---|---|---|---|---|
|  |  | <1% | 1-5% | 5-40% | Other | Concordance | Discordance | Total | Concordance rate |
| FVIII activity level (actually measured) | <1% | 12 |  |  | 1 | 12 | 1 | 13 | 92.3 |
|  | 1-5% |  | 6 | 1 | 1 | 6 | 2 | 8 | 75.0 |
|  | 5-40% |  |  | 2 | 1 | 2 | 1 | 3 | 66.7 |
|  | Other |  |  | 2 | 8 | 8 | 2 | 10 | 80.0 |
|  | Total | 12 | 6 | 5 | 11 | 28 | 6 | 34 | 82.4 |

FVIII-deficient concordance rate = 85.3% (29 out of 34 specimens)

Analysis results using parameter group A-4

|  |  | FVIII activity level (determined) | | | | FVIII activity level concordance rate (%) | | | |
|---|---|---|---|---|---|---|---|---|---|
|  |  | <1% | 1-5% | 5-40% | Other | Concordance | Discordance | Total | Concordance rate |
| FVIII activity level (actually measured) | <1% | 12 | 1 |  |  | 12 | 1 | 13 | 92.3 |
|  | 1-5% |  | 4 | 4 |  | 4 | 4 | 8 | 50.0 |
|  | 5-40% |  | 1 | 2 |  | 2 | 1 | 3 | 66.7 |
|  | Other |  |  |  | 10 | 10 | 0 | 10 | 100.0 |
|  | Total | 12 | 6 | 6 | 10 | 28 | 6 | 34 | 82.4 |

FVIII-deficient concordance rate = 100% (34 out of 34 specimens)

TABLE 4

Analysis results using parameter group B-1

|  |  | FVIII activity level (determined) | | | | FVIII activity level concordance rate (%) | | | |
|---|---|---|---|---|---|---|---|---|---|
|  |  | <1% | 1-5% | 5-40% | Other | Concordance | Discordance | Total | Concordance rate |
| FVIII activity level (actually measured) | <1% | 12 | 1 |  |  | 12 | 1 | 13 | 92.3 |
|  | 1-5% |  | 5 | 1 | 2 | 5 | 3 | 8 | 62.5 |
|  | 5-40% |  | 1 | 2 |  | 2 | 1 | 3 | 66.7 |
|  | Other |  |  | 1 | 9 | 9 | 1 | 10 | 90.0 |
|  | Total | 12 | 7 | 4 | 11 | 28 | 6 | 34 | 82.4 |

FVIII-deficient concordance rate = 91.2% (31 out of 34 specimens)

Analysis results using parameter group B-2

|  |  | FVIII activity level (determined) | | | | FVIII activity level concordance rate (%) | | | |
|---|---|---|---|---|---|---|---|---|---|
|  |  | <1% | 1-5% | 5-40% | Other | Concordance | Discordance | Total | Concordance rate |
| FVIII activity level (actually measured) | <1% | 12 |  |  | 1 | 12 | 1 | 13 | 92.3 |
|  | 1-5% |  | 4 | 2 | 2 | 4 | 4 | 8 | 50.0 |
|  | 5-40% |  | 1 | 1 | 1 | 1 | 2 | 3 | 33.3 |
|  | Other |  |  | 3 | 7 | 7 | 3 | 10 | 70.0 |
|  | Total | 12 | 5 | 6 | 11 | 24 | 10 | 34 | 70.6 |

FVIII-deficient concordance rate = 79.4% (27 out of 34 specimens)

TABLE 4-continued

Analysis results using parameter group B-3

| | | FVIII activity level (determined) | | | | FVIII activity level concordance rate (%) | | | Concordance rate |
|---|---|---|---|---|---|---|---|---|---|
| | | <1% | 1-5% | 5-40% | Other | Concordance | Discordance | Total | |
| FVIII activity level (actually measured) | <1% | 11 | | | 2 | 11 | 2 | 13 | 84.6 |
| | 1-5% | | 6 | 2 | | 6 | 2 | 8 | 75.0 |
| | 5-40% | | | 2 | 1 | 2 | 1 | 3 | 66.7 |
| | Other | | | 5 | 5 | 5 | 5 | 10 | 50.0 |
| | Total | 11 | 6 | 9 | 8 | 24 | 10 | 34 | 70.6 |

FVIII-deficient concordance rate = 76.5% (26 out of 34 specimens)

Analysis results using parameter group B-4

| | | FVIII activity level (determined) | | | | FVIII activity level concordance rate (%) | | | Concordance rate |
|---|---|---|---|---|---|---|---|---|---|
| | | <1% | 1-5% | 5-40% | Other | Concordance | Discordance | Total | |
| FVIII activity level (actually measured) | <1% | 12 | 1 | | | 12 | 1 | 13 | 92.3 |
| | 1-5% | | 6 | 1 | 1 | 6 | 2 | 8 | 75.0 |
| | 5-40% | | 1 | 2 | | 2 | 1 | 3 | 66.7 |
| | Other | | | | 10 | 10 | 0 | 10 | 100.0 |
| | Total | 12 | 8 | 3 | 11 | 30 | 4 | 34 | 88.2 |

FVIII-deficient concordance rate = 97.1% (33 out of 34 specimens)

TABLE 5

Analysis results using comparison parameter group 1

| | | FVIII activity level (determined) | | | | FVIII activity level concordance rate (%) | | | Concordance rate |
|---|---|---|---|---|---|---|---|---|---|
| | | <1% | 1-5% | 5-40% | Other | Concordance | Discordance | Total | |
| FVIII activity level (actually measured) | <1% | 9 | | | 4 | 9 | 4 | 13 | 69.2 |
| | 1-5% | | 1 | 2 | 5 | 1 | 7 | 8 | 12.5 |
| | 5-40% | | | 1 | 2 | 1 | 2 | 3 | 33.3 |
| | Other | | 1 | 1 | 8 | 8 | 2 | 10 | 80.0 |
| | Total | 9 | 2 | 4 | 19 | 19 | 15 | 34 | 55.9 |

FVIII-deficient concordance rate = 61.8% (21 out of 34 specimens)

The kinds of the parameter groups used in the analysis, the FVIII-deficient concordance rates, and the FVIII activity level concordance rates are summarized in Table 6. In the method using the parameter group A or B, the FVIII activity level of a test specimen was able to be determined with a high concordance rate.

TABLE 6

| Parameter group | | Parameter content | Number of parameters | FVIII-deficient concordance rate | FVIII activity level concordance rate |
|---|---|---|---|---|---|
| Comparison parameter group 1 (conventional method) | | Vmax, VmaxT Amax, AmaxT | 4 | 61.8 | 55.9 |
| Parameter group A (S = 5%, 10%, 20%, 30%, 40%, 50%, 60%, 70%., 80%, and 90%) | A-1 | vH, vT, vB, vAB, vTB | 50 | 97.1 | 82.4 |
| | A-2 | vB, vAB, vTB | 30 | 88.2 | 85.3 |
| | A-3 | vB, vAB | 20 | 85.3 | 82.4 |
| | A-4 | vH, vT, vB, vAB, vTB + Vmax, VmaxT Amax, AmaxT | 54 | 100 | 82.4 |

TABLE 6-continued

| Parameter group | | Parameter content | Number of parameters | FVIII-deficient concordance rate | FVIII activity level concordance rate |
|---|---|---|---|---|---|
| Parameter group B (S = 5%, 20%, 40%, 60%, and 80%) | B-1 | vH, vT, vB, vAB, vTB | 25 | 91.2 | 82.4 |
| | B-2 | vB, vAB, vTB | 15 | 79.4 | 70.6 |
| | B-3 | vB, vAB | 10 | 76.5 | 70.6 |
| | B-4 | vH, vT, vB, vAB, vTB + Vmax, VmaxT Amax, AmaxT | 29 | 97.1 | 88.2 |

Example 3: Difference in Determination Results Due to Difference in Evaluation Criteria for Correlation In order to confirm the difference in the determination results due to the difference of the evaluation criteria for correlation, a comparison study was conducted under the following two conditions in which only the evaluation criteria for correlation are different. As the parameter group, a parameter group A-4 was used.

Evaluation criteria 1 for correlation: Linear regression equations for the parameter groups between all the template specimens and the test specimens were determined, template specimens having a tilt of the regression line in the range of from 0.87 to 1.13 were selected, and a template specimen with which the correlation coefficient was the highest was selected from the selected template specimens (the same evaluation criteria as in Example 2).

Evaluation criteria 2 for correlation: Linear regression equations for the parameter groups between all the template specimens and the test specimens were determined, a template specimen with which the correlation coefficient was the highest was selected.

The determination results are shown in Table 7 (Table 7-1 is the same as Table 3A-4). The kinds of the parameters used in the analysis, the FVIII-deficient concordance rates, and the FVIII activity level concordance rates are summarized in Table 8.

TABLE 7

Analysis results using evaluation criteria 1 for correlation

| | | FVIII activity level (determined) | | | | FVIII activity level concordance rate (%) | | | |
|---|---|---|---|---|---|---|---|---|---|
| | | <1% | 1-5% | 5-40% | Other | Concordance | Discordance | Total | Concordance rate |
| FVIII activity level (actually measured) | <1% | 12 | 1 | | | 12 | 1 | 13 | 92.3 |
| | 1-5% | | 4 | 4 | | 4 | 4 | 8 | 50.0 |
| | 5-40% | | 1 | 2 | | 2 | 1 | 3 | 66.7 |
| | Other | | | | 10 | 10 | 0 | 10 | 100.0 |
| | Total | 12 | 6 | 6 | 10 | 28 | 6 | 34 | 82.4 |

FVIII-deficient concordance rate = 100% (34 out of 34 specimens)

Analysis results using evaluation criteria 2 for correlation

| | | FVIII activity level (determined) | | | | FVIII activity level concordance rate (%) | | | |
|---|---|---|---|---|---|---|---|---|---|
| | | <1% | 1-5% | 5-40% | Other | Concordance | Discordance | Total | Concordance rate |
| FVIII activity level (actually measured) | <1% | 11 | 2 | | | 11 | 2 | 13 | 84.6 |
| | 1-5% | | 4 | 4 | | 4 | 4 | 8 | 50.0 |
| | 5-40% | | | 3 | | 3 | 0 | 3 | 100.0 |
| | Other | 1 | | | 9 | 9 | 1 | 10 | 90.0 |
| | Total | 12 | 6 | 7 | 9 | 27 | 7 | 34 | 79.4 |

FVIII-deficient concordance rate = 97.1% (33 out of 34 specimens)

TABLE 8

| Parameter group | Parameter content | Number of parameters | FVIII-deficient concordance rate | FVIII activity level concordance rate |
|---|---|---|---|---|
| Evaluation criteria 1 for correlation Tilt + correlation coefficient | vH, vT, vB, vAB, vTB, + Vmax, VmaxT, Amax, AmaxT | 54 | 100 | 82.4 |
| Evaluation criteria 2 for correlation Correlation coefficient | vH, vT, vB, vAB, vTB, + Vmax, VmaxT, Amax, AmaxT | 54 | 97.1 | 79.4 |

Example 4: Determination of FIX Activity Level

Determination of the FIX activity was performed on 8 specimens that are determined to be Other (FVIII>406) but are FIX deficient among the test specimens. The template specimens shown in Table 9 were used. As the parameter group, a parameter group A-1 acquired in Example 1 was used, and the evaluation criteria 1 for correlation in Example 3 was used in the evaluation for correlation. By a procedure similar to that of (2) in Example 2, the FIX activity level concordance rate and the FIX-deficient concordance rate were calculated. The evaluation results are shown in Table 10. The FIX activity level of a test specimen was able to be determined with a high concordance rate.

TABLE 9

Constitution of template specimen

| Template specimen | Number of specimens | Coagulation factor activity | | | |
|---|---|---|---|---|---|
| | | <1% | 1-5% | 5-40% | Other |
| Specimen with different FIX activity | 16 | 5 | 4 | 6 | 1 |
| Specimen with other factors | 61 | 0 | 0 | 0 | 61 |
| Total | 77 | 5 | 4 | 6 | 62 |

Specimen with other factors: plasma deficient of a coagulation factor other than FIX, heparinized plasma, and LA-positive plasma Example 5: Determination of FVIII Activity or Abnormality (1) Subject Blood Specimen and Template Specimen As the subject blood specimen, 46 plasma specimens of patients having a decreased FVIII activity or FIX activity were used. The 46 specimen consisted of 30 FVIII-deficient specimens (10 specimens of severe severity (FVIII<1%), 10 specimens of moderate severity (FVIII=1 to 5%), and 10 specimens of mild severity (FVIII=5 to 40%)), 1 specimen (Other) of FVIII>40%, and 15 FIX-deficient specimens (Other).

As the template specimens, a mixed plasma obtained by mixing a commercially available coagulation factor-deficient plasma with a lupus anticoagulant (LA) or normal plasma in various proportions, and a FVIII-added plasma obtained by adding a FVIII preparation into a commercially available FVIII-deficient plasma were used. As the coagulation factor-deficient plasma and the LA plasma, Factor VIII Deficient Plasma, Factor IX Deficient Plasma, Factor V Deficient Plasma, Factor X Deficient Plasma, Factor XI Deficient Plasma, Factor XII Deficient Plasma, Prekallikrein Deficient Plasma, or Positive Lupus Anticoagulant Plasma (all of which are manufactured by George King Bio-Medical, Inc.) were used. As the FVIII preparation, a gene recombinant blood coagulation factor VIII preparation, ADVATE (manufactured by Shire Japan KK) was used. As the normal plasma, a normal pool plasma in which the concentration of each factor can be regarded as 100% was used. By mixing a normal plasma with a coagulation factor-deficient plasma in various proportions, mixed plasmas having a factor concentration of 0.25%, 0.5, 0.75%, 1%, 2.5%, 5%, 10%, 25%, and 50%, respectively were prepared. Further, by adding a FVIII preparation into a FVIII-deficient plasma, FVIII-added plasmas having a FVIII concentration of 0.625%, 1.25%, 2.5%, 5%, 10%, 20%, 40%, 80%, and 160%, respectively were prepared. In addition, by adding a FVIII preparation into another FVIII-deficient plasma, FVIII-added plasmas having a FVIII concentration of 0.3%, 0.6%, 1%, 2%, 4%, 8%, 16%, 32%, 64%, and 128%, respectively were prepared. With the above procedure, 143 template specimens in total of 59 FVIII-activity abnormal specimens, 80 factor-deficient specimens each having a

TABLE 10

Analysis results using parameter group A-1

| | | FIX activity level (determined) | | | | FIX activity level concordance rate (%) | | | |
|---|---|---|---|---|---|---|---|---|---|
| | | <1% | 1-5% | 5-40% | Other | Concordance | Discordance | Total | Concordance rate |
| FIX activity level (actually measured) | <1% | 2 | | | | 2 | 0 | 2 | 100.0 |
| | 1-5% | | 2 | 1 | 1 | 2 | 2 | 4 | 50.0 |
| | 5-40% | | | 2 | | 2 | 0 | 2 | 100.0 |
| | Other | | | | | 0 | 0 | 0 | — |
| | Total | 2 | 2 | 3 | 1 | 6 | 2 | 8 | 75.0 |

FIX-deficient concordance rate = 87.5% (7 out of 8 specimens)

normal FVIII activity but reduced other coagulation factors, and 4 LA-positive specimens were prepared. In the 59 FVIII-activity abnormal specimens, the FVIII activity level belonged to any one of severe hemophilia A (FVIII<1%), moderate hemophilia A (FVIII=1 to 5%), mild hemophilia A (FVIII=5 to 40%), and Other (FVIII>40%). The remaining 84 specimens belonged to "Other" because the FVIII activity was not abnormal.

In the present Example, all of the test specimens were specimens either from a FVIII-deficient patient (hemophilia A) or from a FIX-deficient patient (hemophilia B), and the template specimens were prepared on the basis of a commercially available factor-deficient plasma or a LA-positive plasma without using any specimen from a patient with hemophilia A or hemophilia B. With such a specimen constitution, in the present Example, the conditions were set so that it was difficult to correctly determine the state of the coagulation factor of the test specimen, as compared with Example 2. Constitutions of the test specimens and template specimens used in the present Example are shown in Table 11.

TABLE 11

|  | Number of specimens | FVIII <1% | FVIII 1-5% | FVIII 5-40% | Other |
|---|---|---|---|---|---|
| Constitution of test specimen | | | | | |
| FVIII-deficient specimen | 31 | 10 | 10 | 10 | 1 |
| FIX-deficient specimen | 15 | — | — | — | 15 |
| Total | 46 | 10 | 10 | 10 | 16 |
| Constitution of template specimen | | | | | |
| Specimen with different FVIII activity | 59 | 18 | 12 | 18 | 11 |
| Specimen with different FIX activity | 30 | — | — | — | 30 |
| Specimen with different FV activity | 10 | — | — | — | 10 |
| Specimen with different FX activity | 10 | — | — | — | 10 |
| Specimen with different FXI activity | 10 | — | — | — | 10 |
| Specimen with different FXII activity | 10 | — | — | — | 10 |
| Prekallikrein (PK) specimen | 10 | — | — | — | 10 |
| Lupus Anticoagulant (LA) specimen | 4 | — | — | — | 4 |
| Total | 143 | 18 | 12 | 18 | 95 |

Figure 18:
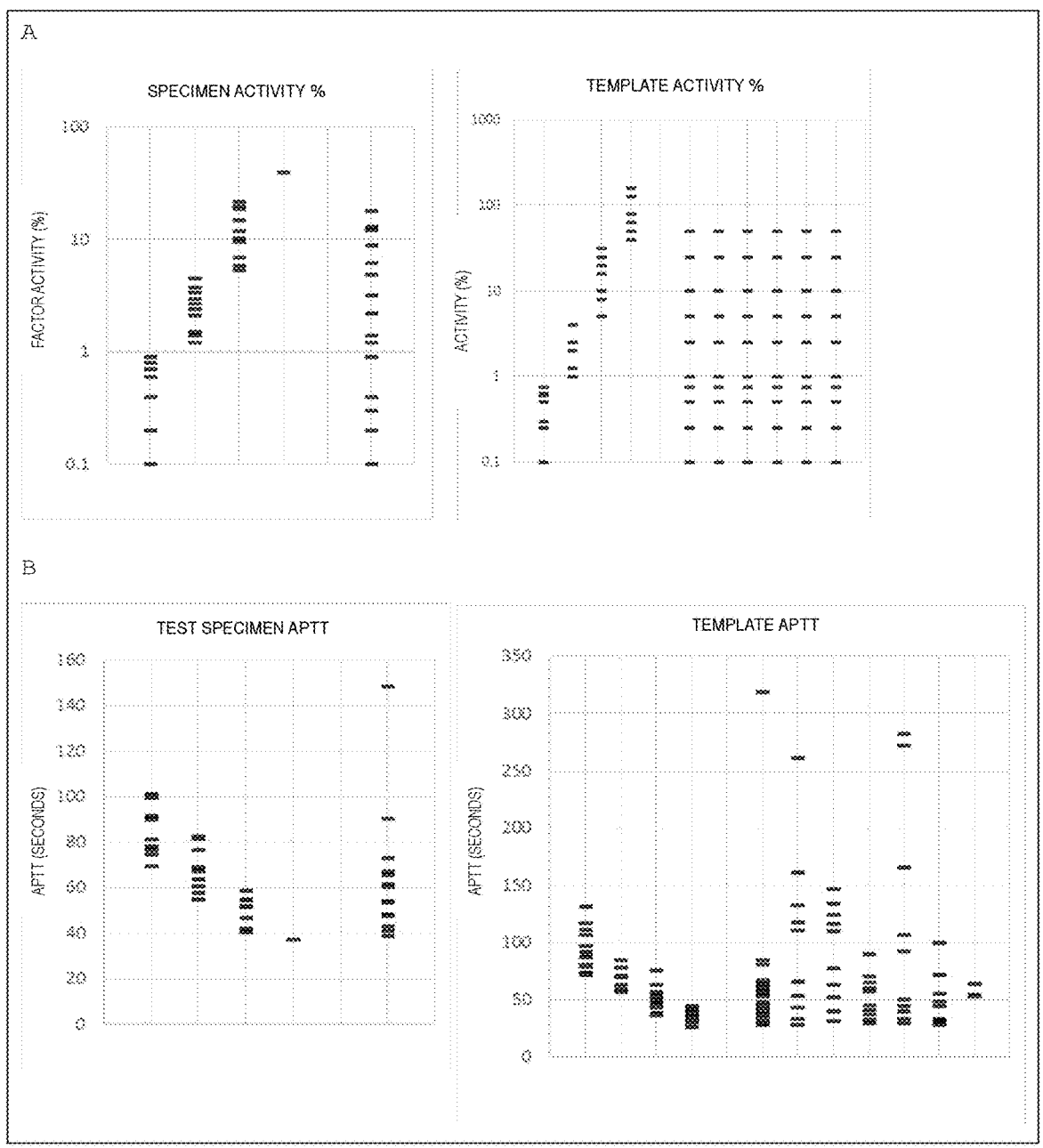
FIG. 18 shows distributions of the FVIII activity and APTT for the test specimens and template specimens used in Example 5. A: FVIII activity, and B: APTT. Left: test specimens, and Right: template specimens.

In accordance with the procedure of (1) in Example 1, a coagulation reaction curve for each of the test specimens and template specimens was obtained. The distributions of the FVIII activity and APTT for the test specimens and template specimens are shown in FIG. 18.

(2) Preparation of Parameter Group

For each specimen, an uncorrected primary curve, an uncorrected secondary curve, a corrected primary curve, and a corrected secondary curve were calculated from a coagulation reaction curve. For each curve, 10 areas of calculation target areas based on 10 levels of calculation target area levels S (5%, 10%, 20%, 30%, 40%, 50%, 60%, 70%, 80%, and 90% of the maximum height of the curve) were extracted, and the parameters characterizing each calculation target area were acquired. Further, the maximum values of a curve being conventional parameters and the times to reach the maximum values (Vmax, RVmax, VmaxT, Amax, RVmax, and AmaxT) were acquired. The acquired parameters are shown in Table 12.

TABLE 12

| | Primary curve | | Secondary curve | | | |
|---|---|---|---|---|---|---|
| | Corrected | Uncorrected | Corrected (+peak) | Corrected (−peak) | Uncorrected (+peak) | Uncorrected (−peak) |
| Conventional parameter | | | | | | |
| | Vmax | RVmax | Amax | — | RAmax | — |
| | VmaxT | VmaxT | AmaxT | — | RAmaxT | — |
| Parameters characterizing calculation target area x: Calculation target area level (5%, 10%, 20%, 30%, 40%, 50%, 60%, 70%, 80%, and 90%) | | | | | | |
| vHx | RvHx | pHx | mHx | RpHx | RmHx |
| vHax | RvHax | — | — | — | — |
| vTx | — | pTx | mTx | — | — |
| vTax | — | — | — | — | — |
| vBx | — | pBx | mBx | — | — |

TABLE 12-continued

| | Primary curve | | Secondary curve | | | |
|---|---|---|---|---|---|---|
| | Corrected | Uncorrected | Corrected (+peak) | Corrected (−peak) | Uncorrected (+peak) | Uncorrected (−peak) |
| vNx | — | pNx | mNx | — | — |
| vWx | — | pWx | mWx | — | — |
| vTrx | — | — | — | — | — |
| vNsx | — | pNsx | mNsx | — | — |
| vNex | — | pNex | mNex | — | — |
| vTsx | — | — | — | — | — |
| vTex | — | — | — | — | — |
| vTmx | — | — | — | — | — |
| vAUCx | RvAUCx | pAUCx | mAUCx | RpAUCx | RmAUCx |
| vABx | RvABx | pABx | mABx | — | — |
| vABax | RvABax | — | — | — | — |
| vAWx | RvAWx | pAWx | mAWx | — | — |
| vAWax | RvAWax | — | — | — | — |
| vTBx | — | pTBx | mTBx | — | — |
| vTWx | — | pTWx | mTWx | — | — |

(3) Determination of FVIII Activity or Abnormality of Test Specimen Using Parameter Group
(3-1) Determination Using Single Parameter A parameter group was prepared from the parameters shown in Table 12. In a case where the parameters characterizing the calculation target area were used, a set of parameters of the same kind extracted from 10 areas of calculation target areas based on 10 levels of calculation target area levels (x=5%, 10%, 20%, 30%, 40%, 50%, 60%, 70%, 80%, and 90%) was used as the parameter group. For example, in a case where a parameter "vHx" was used, a set of [vH5%, vH10%, vH20%, vH30%, vH40%, vH50%, vH60%, vH70%, vH80%, and vH90%] was used as the parameter group. In a case where conventional parameters were used, the same parameter group as in the comparative example of Example 2 was used.

The FVIII activity or abnormality of a test specimen was determined by a regression analysis using the parameter group. A primary regression analysis was performed between the test parameter group obtained from a test specimen, and the corresponding template parameter group obtained from each template specimen. Template specimens with each of which the tilt of the primary regression equation obtained by the regression analysis was within 1±0.15 and the correlation coefficient of the primary regression equation was larger than 0.90 were extracted. A template specimen having the largest correlation coefficient among the extracted template specimens was selected. In a case where multiple specimens that have the same correlation coefficient were present, a template specimen having a tilt of the regression equation closer to 1 was selected. The state of FVIII activity (severe hemophilia A (FVIII<1%), moderate hemophilia A (FVIII=1 to 5%), mild hemophilia A (FVIII=5 to 40%), or others (Other)) in the selected template specimen was determined as the state of the FVIII activity of the test specimen. On the basis of the determination results for all the test specimens, the FVIII-deficient concordance rate and the FVIII activity level concordance rate were calculated by a procedure similar to that in Example 2.

The parameter groups used, and the obtained FVIII-deficient concordance rates and FVIII activity level concordance rates are shown in Tables 13 and 14. The parameter with the highest (63.0%) FVIII-deficient concordance rate was the parameter pHx of the secondary curve. The parameter with the highest (76.1%) FVIII activity level concordance rate was the parameter mTx of the secondary curve. The heights of the FVIII-deficient concordance rate and the FVIII activity level concordance rate were not correlated with each other. The FVIII-deficient concordance rate was 52.2% in a case where conventional parameters (combination of VmaxT, AmaxT, Vmax, and Amax) were used.

TABLE 13

| Parameter group | FVIII-deficient concordance rate (%) | FVIII activity level concordance rate (%) | Parameter group | FVIII-deficient concordance rate (%) | FVIII activity level concordance rate (%) | Parameter group | FVIII-deficient concordance rate (%) | FVIII activity level concordance rate (%) |
|---|---|---|---|---|---|---|---|---|
| Vmax | 52.2 | 63.0 | | | | | | |
| VmaxT | | | | | | | | |
| Amax | | | | | | | | |
| AmaxT | | | | | | | | |
| vHx | 60.9 | 67.4 | pHx | 63.0 | 67.4 | mHx | 43.5 | 52.2 |
| vHax | 58.7 | 71.7 | — | — | — | — | — | — |
| vTx | 52.2 | 60.9 | pTx | 41.3 | 56.5 | mTx | 52.2 | 76.1 |
| vTax | 58.7 | 67.4 | — | — | — | — | — | — |
| vBx | 54.3 | 58.7 | pBx | 47.8 | 58.7 | mBx | 47.8 | 63.0 |
| vNx | 47.8 | 63.0 | pNx | 32.6 | 45.7 | mNx | 45.7 | 54.3 |
| vWx | 56.5 | 63.0 | pWx | 52.2 | 69.6 | mBx | 50.0 | 67.4 |
| vTrx | 47.8 | 50.0 | — | — | — | — | — | — |
| vNsx | 52.2 | 60.9 | pNsx | 45.7 | 69.6 | mNsx | 37.0 | 37.0 |
| vNex | 54.3 | 56.5 | pNex | 47.8 | 52.2 | mNex | 41.3 | 47.8 |
| vTsx | 50.0 | 56.5 | — | — | — | — | — | — |
| vTex | 50.0 | 52.2 | — | — | — | — | — | — |
| vTmx | 54.3 | 56.5 | — | — | — | — | — | — |
| vAUCx | 34.8 | 39.1 | pAUCx | 58.7 | 69.6 | mAUCx | 52.2 | 65.2 |
| vABx | 58.7 | 67.4 | pABx | 60.9 | 69.6 | mABx | 54.3 | 67.4 |
| vABax | 56.5 | 63.0 | — | — | — | — | — | — |
| vAWx | 50.0 | 54.3 | pAWx | 52.2 | 63.0 | mAWx | 50.0 | 50.0 |
| vAWax | 47.8 | 52.2 | — | — | — | — | — | — |
| vTBx | 56.5 | 71.7 | pTBx | 50.0 | 71.7 | mTBx | 52.2 | 63.0 |
| vTWx | 56.5 | 69.6 | pTWx | 50.0 | 69.6 | mTWx | 39.1 | 56.5 |

TABLE 14

| Parameter group | FVIII-deficient concordance rate (%) | FVIII activity level concordance rate (%) | Parameter group | FVIII-deficient concordance rate (%) | FVIII activity level concordance rate (%) | Parameter group | FVIII-deficient concordance rate (%) | FVIII activity level concordance rate (%) |
|---|---|---|---|---|---|---|---|---|
| RVmax | 39.1 | 54.3 | | | | | | |
| VmaxT | | | | | | | | |
| RAmax | | | | | | | | |
| AmaxT | | | | | | | | |

TABLE 14-continued

| Parameter group | FVIII-deficient concordance rate (%) | FVIII activity level concordance rate (%) | Parameter group | FVIII-deficient concordance rate (%) | FVIII activity level concordance rate (%) | Parameter group | FVIII-deficient concordance rate (%) | FVIII activity level concordance rate (%) |
|---|---|---|---|---|---|---|---|---|
| RvHx | 58.7 | 65.2 | RpHx | 50.0 | 56.5 | RmHx | 54.3 | 63.0 |
| RvHax | 58.7 | 63.0 | — | — | — | — | — | — |
| RvAUCx | 39.1 | 54.3 | RpAUCx | 34.8 | 41.3 | RmAUCx | 52.2 | 63.0 |
| RvABx | 39.1 | 50.0 | — | — | — | — | — | — |
| RvABax | 41.3 | 52.2 | — | — | — | — | — | — |
| RvAWx | 39.1 | 50.0 | — | — | — | — | — | — |
| RvAWax | 39.1 | 50.0 | — | — | — | — | — | — |

(3-1) Determination Using Combination Parameter

A combination parameter group was prepared by combining multiple kinds of parameters that characterize the calculation target area shown in Table 12. Two or more sets of parameters of the same kind extracted from 10 areas of calculation target areas based on 10 levels of calculation target area levels (x=5%, 10%, 20%, 30%, 40%, 50%, 60%, 70%, 80%, and 90%) were combined and used as a parameter group. For example, in a case where a combination of parameters "VT" and "vB" was used, a combination of a set of [vT5%, vT10%, vT20%, vT30%, vT40%, vT50%, vT60%, vT70%, vT80%, and vT90%] and a set of [vB5%, vB10%, vB20%, vB30%, vB40%, vB50%, vB60%, vB70%, vB80%, and vB90%] was used as a parameter group.

The combination parameter groups with high FVIII-deficient concordance rates, and the obtained FVIII-deficient concordance rates and FVIII activity level concordance rates are shown in Tables 15 and 16. The results in a case of a combination of 2 kinds of parameters are shown in Table 15, and the results in a case of a combination of 3 kinds of parameters are shown in Table 16. The results of a parameter group (pNs_pNe_vTB) with the highest FVIII activity level concordance rate are also shown in Table 16.

TABLE 15

| Parameter group | FVIII-deficient concordance rate (%) | FVIII activity level concordance rate (%) |
|---|---|---|
| pAB_pNe | 71.7 | 78.3 |
| pTW_vT | 69.6 | 84.8 |
| pTB_vABa | 69.6 | 80.4 |
| pAB_vNs | 69.6 | 80.4 |
| RvHa_vN | 69.6 | 76.1 |
| pNe_vTa | 69.6 | 76.1 |
| vT_vTr | 69.6 | 73.9 |
| pAW_pTB | 67.4 | 82.6 |
| pTB_vTa | 67.4 | 78.3 |
| pTW_vNs | 67.4 | 78.3 |
| pAB_pTW | 67.4 | 78.3 |
| pAB_pTB | 67.4 | 78.3 |
| pTW_vTr | 67.4 | 76.1 |
| pH_vHa | 67.4 | 76.1 |
| pAB_pNs | 67.4 | 76.1 |
| vTr_vTW | 67.4 | 73.9 |
| vT_vB | 67.4 | 73.9 |
| vTs_vB | 67.4 | 73.9 |
| vB_vNs | 67.4 | 73.9 |
| pNs_vTa | 67.4 | 73.9 |

TABLE 16

| Parameter group | FVIII-deficient concordance rate (%) | FVIII activity level concordance rate (%) |
|---|---|---|
| pTW_vTs_vW | 78.3 | 84.8 |
| pTB_vTs_vN | 78.3 | 82.6 |
| pTB_vT_vTr | 76.1 | 84.8 |
| pTB_vTa_vTr | 76.1 | 84.8 |
| pTB_vTm_vTr | 76.1 | 84.8 |
| pTB_vW_vNs | 76.1 | 84.8 |
| pTW_vT_vW | 76.1 | 84.8 |
| pTW_vW_vNs | 76.1 | 84.8 |
| pTB_vTs_vTr | 76.1 | 82.6 |
| pTW_vTa_vW | 76.1 | 82.6 |
| pTW_vTs_vTr | 76.1 | 82.6 |
| pTW_vTs_vN | 76.1 | 82.6 |
| mH_pTB_vNs | 73.9 | 84.8 |
| mN_pTW_RvHa | 73.9 | 84.8 |
| pAB_pTW_RmH | 73.9 | 84.8 |
| pAB_RmH_vNs | 73.9 | 84.8 |
| pTW_RvH_vW | 73.9 | 84.8 |
| mW_mTB_pTW | 73.9 | 82.6 |
| mAUC_pTW_vNs | 73.9 | 82.6 |
| pT_pTW_vTe | 73.9 | 82.6 |
| pNs_pNe_vTB | 69.6 | 91.3 |

The determination results of the FVIII activity level for the parameter groups that resulted in the high FVIII-deficient concordance rates or FVIII activity level concordance rates in the above (3-1) and (3-2) are shown in Table 17. As the number of kinds of parameters to be used increased, both of the FVIII-deficient concordance rate and the FVIII activity level concordance rate tended to increase. Further, from these results, it was indicated that the parameters related to a secondary curve are useful for the determination.

TABLE 17

| | | FVIII activity level (determined) | | | | |
|---|---|---|---|---|---|---|
| pH | | <1% | 1-5% | 5-40% | Other | Total |
| FVIII activity level (actually measured) | <1% | 6 | 1 | 0 | 3 | 10 |
| | 1-5% | 0 | 6 | 0 | 4 | 10 |
| | 5-40% | 0 | 1 | 4 | 5 | 10 |
| | Other | 1 | 0 | 2 | 13 | 16 |
| Total | | 7 | 8 | 6 | 25 | 46 |

TABLE 17-continued

FVIII-deficient concordance rate = 63.0%
FVIII activity level concordance rate = 67.4%

| pAB_pNe | | <1% | 1-5% | 5-40% | Other | Total |
|---|---|---|---|---|---|---|
| FVIII activity level | <1% | 7 | 2 | 0 | 1 | 10 |
| (actually measured) | 1-5% | 1 | 5 | 0 | 4 | 10 |
| | 5-40% | 0 | 0 | 5 | 5 | 10 |
| | Other | 0 | 0 | 0 | 16 | 16 |
| | Total | 8 | 7 | 5 | 26 | 46 |

FVIII-deficient concordance rate = 71.7%
FVIII activity level concordance rate = 78.3%

| pTW_vTs_vW | | <1% | 1-5% | 5-40% | Other | Total |
|---|---|---|---|---|---|---|
| FVIII activity level | <1% | 7 | 2 | 0 | 1 | 10 |
| (actually measured) | 1-5% | 0 | 8 | 1 | 1 | 10 |
| | 5-40% | 0 | 0 | 9 | 1 | 10 |
| | Other | 1 | 1 | 2 | 12 | 16 |
| | Total | 8 | 11 | 12 | 15 | 46 |

FVIII-deficient concordance rate = 78.3%
FVIII activity level concordance rate = 84.8%

| mT | | <1% | 1-5% | 5-40% | Other | Total |
|---|---|---|---|---|---|---|
| FVIII activity level | <1% | 4 | 4 | 1 | 1 | 10 |
| (actually measured) | 1-5% | 5 | 3 | 00 | 2 | 10 |
| | 5-40% | 1 | 00 | 3 | 6 | 10 |
| | Other | 1 | 00 | 1 | 14 | 16 |
| | Total | 11 | 7 | 5 | 23 | 46 |

FVIII-deficient concordance rate = 52.2%
FVIII activity level concordance rate = 76.1%

| pTW_vT | | <1 | 1-5% | 5-40% | Other | Total |
|---|---|---|---|---|---|---|
| FVIII activity level | <1% | 8 | 2 | 0 | 0 | 10 |
| (actually measured) | 1-5% | 3 | 4 | 1 | 2 | 10 |
| | 5-40% | 0 | 1 | 8 | 1 | 10 |
| | Other | 1 | 0 | 3 | 12 | 16 |
| | Total | 12 | 7 | 12 | 15 | 46 |

FVIII-deficient concordance rate = 69.6%
FVIII activity level concordance rate = 84.8

| pNs_pNe_vTB | | <1% | 1-5% | 5-40% | Other | Total |
|---|---|---|---|---|---|---|
| FVIII activity level | <1% | 8 | 2 | 0 | 0 | 10 |
| (actually measured) | 1-5% | 5 | 3 | 1 | 1 | 10 |
| | 5-40% | 0 | 2 | 5 | 3 | 10 |
| | Other | 0 | 0 | 0 | 16 | 16 |
| | Total | 13 | 7 | 6 | 20 | 46 |

FVIII-deficient concordance rate = 69.6%
FVIII activity level concordance rate = 91.3%

Example 6: Determination of FVIII Activity or Abnormality by Different Determination Criteria (1) Method By using the specimens used in Example 5, a primary regression analysis was performed between the test parameter group and the template parameter group by a procedure similar to that in Example 5. Next, in accordance with the following different determination criteria, the state of the FVIII activity of the test specimen was determined.

Determination Criteria 1:

In a similar manner as in Example 5, the state of the FVIII activity in a template specimen having the largest correlation coefficient among the template specimens with each of which the tilt of the primary regression equation was within 1±0.15 and the correlation coefficient of the regression equation was larger than 0.90 was determined as the state of the FVIII activity of the test specimen. In a case where there was no template specimen that matched to the tilt and correlation coefficient conditions of the above primary regression equation, the test specimen was determined to be Other.

Determination Criteria 2 (Maximum Selection Method):

Among the template specimens with each of which the tilt of the primary regression equation was within 1±0.15 and the correlation coefficient of the regression equation was larger than 0.90, 5 template specimens having the largest correlation coefficient were extracted. Among these 5 specimens, a state of the FVIII activity, which was observed with the highest frequency, was determined as the state of the FVIII activity of the test specimen. In a case where the same number of specimens with different states are present, a more severe state was determined as the state of the test specimen. In a case where there was no template specimen that matched to the tilt and correlation coefficient conditions of the above primary regression equation, the test specimen was determined to be Other.

Determination Criteria 3 (Two-Stage Selection Method):

Among the template specimens with each of which the tilt of the primary regression equation of the specimen derived from a patient with (severe, moderate, or mild) hemophilia A was within 1±0.15 and the correlation coefficient of the regression equation was larger than 0.90, 5 template specimens having the largest correlation coefficient were extracted. In a case where the number of the template specimens that matched to the tilt and correlation coefficient conditions of the above primary regression equation was less than 5, the less than 5 of the template specimens were taken as ND (see Table 18). The total number of patients with hemophilia A (severe [L1]: FVIII<1%, moderate [L2]: FVIII=1 to 5%, and mild [L3]: FVIII=5 to 40%) in the less than 5 of the template specimens, and the total number of others (Other and ND) were determined. In a case where the total number of the patients with hemophilia A was larger, a state (severe, moderate, or mild) that was observed with the highest frequency was determined as the state of the test specimen. In a case where the same number of specimens with different states are present, a more severe state was determined as the state of the test specimen. In a case where the total number of others was larger, the state of the test specimen was determined as Other.

An example of the determination procedure is shown in Table 18. The FVIII activity of the template specimen of <1> in the correlation coefficient ranking was matched with the determination result based on determination criteria 1. The FVIII activity of the template specimen, which had the largest number, was matched with the determination result based on determination criteria 2. If the total number of L1 to L3 in the template specimen was larger, the result based on determination criteria 3 was any one of L1 to L3, and if the total number of Other and ND was larger, the result based on determination criteria 3 was Other.

TABLE 18

| Case ex | FVIII activity of extracted template specimen <Correlation coefficient ranking> | | | | | Number of template specimens under each category of FVIII activity classification | | | | | Determination results of test specimen based on each determination criteria | | |
|---|---|---|---|---|---|---|---|---|---|---|---|---|---|
| | <1> | <2> | <3> | <4> | <5> | L1 | L2 | L3 | Other | ND | 1 | 2 | 3 |
| 1 | L1 | L1 | L1 | L1 | L1 | 5 | 0 | 0 | 0 | 0 | L1 | L1 | L1 |
| 2 | L1 | L1 | L1 | L1 | L2 | 4 | 1 | 0 | 0 | 0 | L1 | L1 | L1 |
| 3 | L1 | L1 | L1 | L2 | L2 | 3 | 2 | 0 | 0 | 0 | L1 | L1 | L1 |
| 4 | L1 | L1 | L2 | L2 | Other | 2 | 2 | 0 | 1 | 0 | L1 | L1 | L1 |
| 5 | L1 | L2 | L3 | Other | ND | 1 | 1 | 1 | 1 | 1 | L1 | L1 | L1 |
| 6 | L1 | Other | Other | Other | Other | 1 | 0 | 0 | 4 | 0 | L1 | Other | Other |
| 7 | L1 | L1 | Other | Other | Other | 2 | 0 | 0 | 3 | 0 | L1 | Other | Other |
| 8 | L1 | Other | Other | Other | ND | 1 | 0 | 0 | 3 | 1 | L1 | Other | Other |
| 9 | L1 | ND | ND | ND | ND | 1 | 0 | 0 | 0 | 4 | L1 | Other | Other |
| 10 | L1 | Other | ND | ND | ND | 1 | 0 | 0 | 1 | 3 | L1 | Other | Other |
| 11 | L1 | L2 | L2 | Other | Other | 1 | 2 | 0 | 2 | 0 | L1 | L2 | L2 |
| 12 | L1 | Other | Other | ND | ND | 1 | 0 | 0 | 2 | 2 | L1 | Other | Other |
| 13 | L2 | L1 | L3 | Other | ND | 1 | 1 | 1 | 1 | 1 | L2 | L1 | L1 |
| 14 | L1 | L1 | Other | Other | ND | 2 | 0 | 0 | 2 | 1 | L1 | L1 | Other |
| 15 | L1 | L1 | Other | ND | ND | 2 | 0 | 0 | 1 | 2 | L1 | L1 | Other |

L1: FVIII = <1%,
L2: FVIII = 1-5%,
L3: FVIII = 5-40%

(2) Determination 26235 combination parameter groups were prepared by arbitrarily combining three kinds of parameters that characterize 55 kinds of calculation target areas shown in Table 12. By using each of the combination parameter groups, a primary regression analysis, which was used between the test parameter group and the template parameter group, was performed, and then a state of the FVIII activity of the test specimen was determined in accordance with determination criteria 1 to 3. The FVIII-deficient concordance rate or the FVIII activity level concordance rate was calculated by a procedure similar to that in Example 2. Further, the average (average concordance rate) of the FVIII-deficient concordance rates or the FVIII activity level concordance rates was calculated.

Examples of the FVIII-deficient concordance rate, the FVIII activity level concordance rate, and the average concordance rate (which are collectively referred to as concordance rate) determined in accordance with each of the determination criteria are shown in Table 19.

TABLE 19

| Combination parameter group | FVIII-deficient concordance rate Determination criteria | | | FVIII activity level concordance rate Determination criteria | | | Average concordance rate Determination criteria | | |
|---|---|---|---|---|---|---|---|---|---|
| | 1 | 2 | 3 | 1 | 2 | 3 | 1 | 2 | 3 |
| pTW_vTs_vW | 78.3 | 50.0 | 50.0 | 84.8 | 58.7 | 58.7 | 81.5 | 54.3 | 54.3 |
| pTW_vT_vW | 76.1 | 63.0 | 63.0 | 84.8 | 76.1 | 76.1 | 80.4 | 69.6 | 69.6 |
| pTB_vW_vNs | 76.1 | 65.2 | 65.2 | 84.8 | 69.6 | 69.6 | 80.4 | 67.4 | 67.4 |
| pNs_pNe_vTB | 69.6 | 56.5 | 56.5 | 91.3 | 76.1 | 76.1 | 80.4 | 66.3 | 66.3 |
| pTB_vTs_vN | 78.3 | 63.0 | 63.0 | 82.6 | 69.6 | 69.6 | 80.4 | 66.3 | 66.3 |
| pTB_vT_vTr | 76.1 | 63.0 | 63.0 | 84.8 | 67.4 | 67.4 | 80.4 | 65.2 | 65.2 |
| pTB_vTa_vTr | 76.1 | 60.9 | 60.9 | 84.8 | 67.4 | 67.4 | 80.4 | 64.1 | 64.1 |
| pTB_vTm_vTr | 76.1 | 60.9 | 60.9 | 84.8 | 67.4 | 67.4 | 80.4 | 64.1 | 64.1 |
| pTW_vW_vNs | 76.1 | 54.3 | 54.3 | 84.8 | 60.9 | 60.9 | 80.4 | 57.6 | 57.6 |
| pTW_vTa_vW | 76.1 | 76.1 | 76.1 | 82.6 | 84.8 | 84.8 | 79.3 | 80.4 | 80.4 |
| mW_pTB_vTr | 67.4 | 78.3 | 78.3 | 82.6 | 87.0 | 87.0 | 75.0 | 82.6 | 82.6 |
| pW_pTB_vW | 67.4 | 78.3 | 78.3 | 80.4 | 87.0 | 87.0 | 73.9 | 82.6 | 82.6 |
| mB_pTW_vTa | 67.4 | 73.9 | 73.9 | 80.4 | 87.0 | 87.0 | 73.9 | 80.4 | 80.4 |
| mW_pTW_vTe | 67.4 | 73.9 | 73.9 | 76.1 | 87.0 | 87.0 | 71.7 | 80.4 | 80.4 |
| mB_pTW_vTm | 65.2 | 73.9 | 73.9 | 78.3 | 89.1 | 89.1 | 71.7 | 81.5 | 81.5 |
| mB_pTW_vTe | 67.4 | 78.3 | 78.3 | 73.9 | 87.0 | 87.0 | 70.7 | 82.6 | 82.6 |
| mAUC_pTB_vTm | 65.2 | 76.1 | 76.1 | 71.7 | 89.1 | 89.1 | 68.5 | 82.6 | 82.6 |
| mAUC_pTB_vTa | 63.0 | 78.3 | 78.3 | 73.9 | 84.8 | 84.8 | 68.5 | 81.5 | 81.5 |
| pN_pTB_vTm | 63.0 | 73.9 | 73.9 | 69.6 | 87.0 | 87.0 | 66.3 | 80.4 | 80.4 |
| pTB_vTa_vTB | 60.9 | 78.3 | 78.3 | 69.6 | 91.3 | 91.3 | 65.2 | 84.8 | 84.8 |
| pTB_vTm_vTB | 60.9 | 76.1 | 76.1 | 67.4 | 87.0 | 87.0 | 64.1 | 81.5 | 81.5 |
| pN_pTW_vTs | 56.5 | 73.9 | 71.7 | 69.6 | 91.3 | 89.1 | 63.0 | 82.6 | 80.4 |

Table 20 shows the number of combination parameter groups that achieved the level of the concordance rate. The bottom line of Table 20 shows the maximum values of the concordance rate based on each of the determination criteria. The FVIII-deficient concordance rate was 78.3% at most based on any of the criteria. The number of combination parameter groups that satisfy the maximum concordance rate level (exceeding 75% to 80% or less) was 12 based on determination criteria 1, and 17 based on each of determination criteria 2 and 3. The FVIII activity level concordance rate was 91.3% at most based on any of the criteria. The number of parameter groups that satisfy the maximum concordance rate level (exceeding 90% to 95% or less) was one based on each of determination criteria 1 and 3, and two based on determination criteria 2. The maximum value of the average concordance rate was 81.5% based on determination criteria 1, and 84.8% based on each of determination criteria 2 and 3. The number of parameter groups that satisfy the maximum concordance rate level (exceeding 80% to 85% or less) was 9 based on determination criteria 1, and 13 based on each of determination criteria 2 and 3.

TABLE 20

| Rate (%) | FVIII-deficient concordance rate (%) Determination criteria | | | FVIII activity level concordance rate Determination criteria | | | Average concordance rate Determination criteria | | |
|---|---|---|---|---|---|---|---|---|---|
| | 1 | 2 | 3 | 1 | 2 | 3 | 1 | 2 | 3 |
| 50 or less | 11499 | 15298 | 15435 | 2382 | 7532 | 7286 | 5064 | 10233 | 9932 |
| Exceeding 50 to 55 or less | 5741 | 3811 | 3872 | 2475 | 3058 | 2942 | 3989 | 3905 | 4044 |
| Exceeding 55 to 60 or less | 4827 | 3424 | 3320 | 3626 | 3431 | 3449 | 6940 | 4612 | 4754 |
| Exceeding 60 to 65 or less | 2773 | 2207 | 2136 | 4968 | 3478 | 3604 | 5305 | 3606 | 3600 |
| Exceeding 65 to 70 or less | 1294 | 1315 | 1288 | 7668 | 5084 | 5167 | 3786 | 2707 | 2712 |
| Exceeding 70 to 75 or less | 89 | 163 | 167 | 3216 | 2077 | 2137 | 1015 | 992 | 1011 |
| Exceeding 75 to 80 or less | 12 | 17 | 17 | 1411 | 1124 | 1156 | 127 | 167 | 169 |
| Exceeding 80 to 85 or less | 0 | 0 | 0 | 483 | 434 | 477 | 9 | 13 | 13 |
| Exceeding 85 to 90 or less | 0 | 0 | 0 | 5 | 15 | 16 | 0 | 0 | 0 |
| Exceeding 90 to 95 or less | 0 | 0 | 0 | 1 | 2 | 1 | 0 | 0 | 0 |
| Exceeding 95 to 100 or less | 0 | 0 | 0 | 0 | 0 | 0 | 0 | 0 | 0 |
| Maximum concordance rate | 78.3 | 78.3 | 78.3 | 91.3 | 91.3 | 91.3 | 81.5 | 84.8 | 84.8 |

Figure 19:
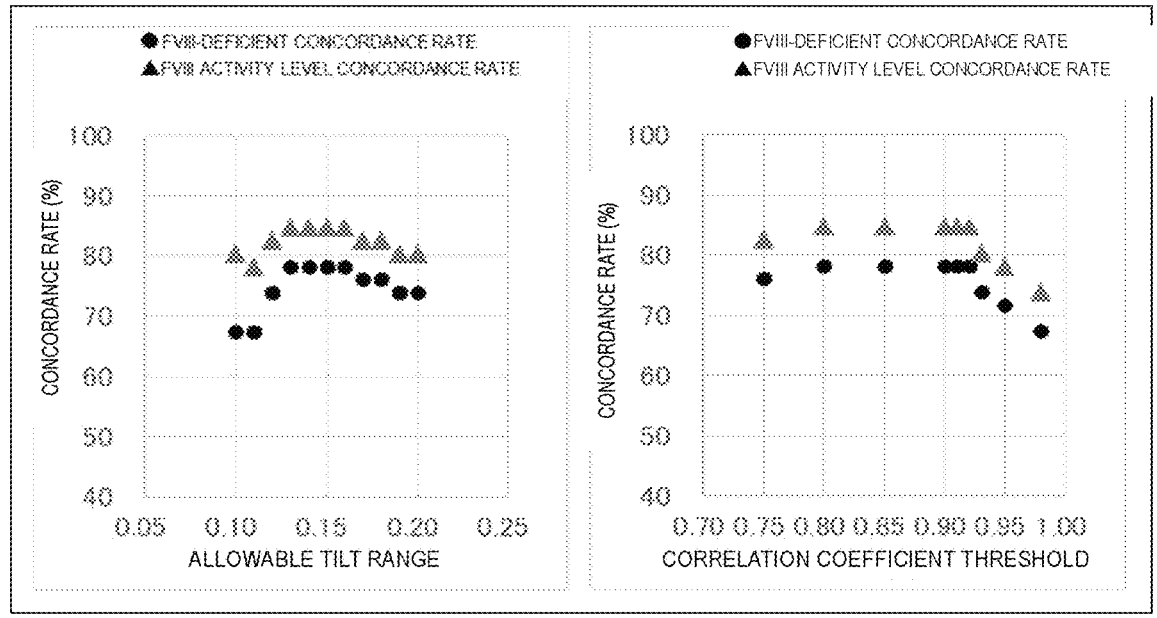
FIG. 19 shows influence of the allowable tilt range and correlation coefficient threshold in regression analysis on the FVIII-deficient concordance rate and FVIII activity-level concordance rate based on determination criteria 1.
Figure 20:
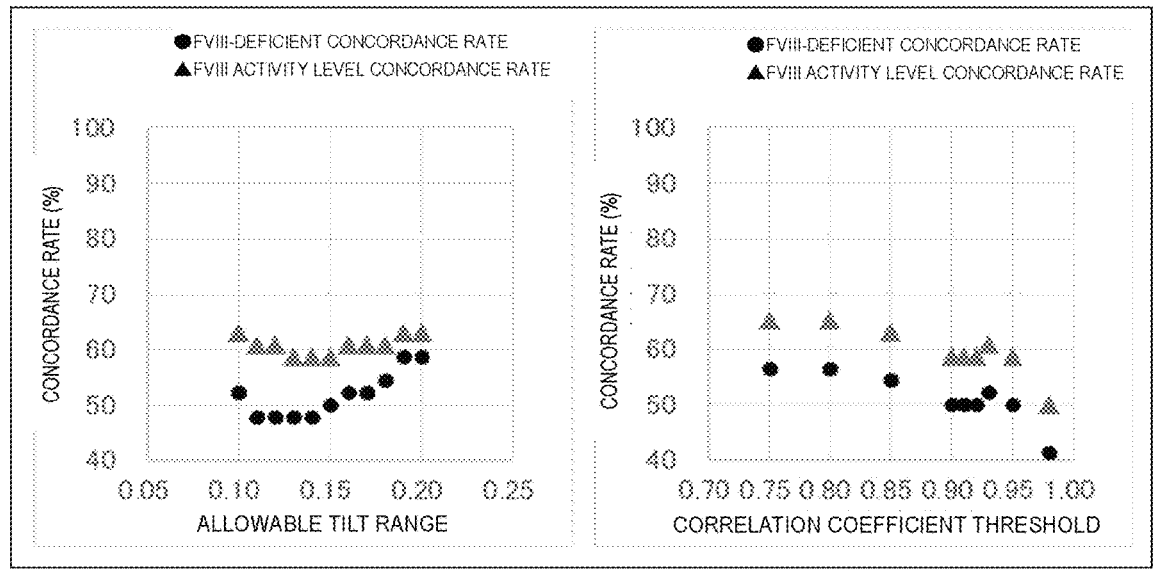
FIG. 20 shows influence of the allowable tilt range and correlation coefficient threshold in regression analysis on the FVIII-deficient concordance rate and FVIII activity-level concordance rate based on determination criteria 2.
Figure 21:
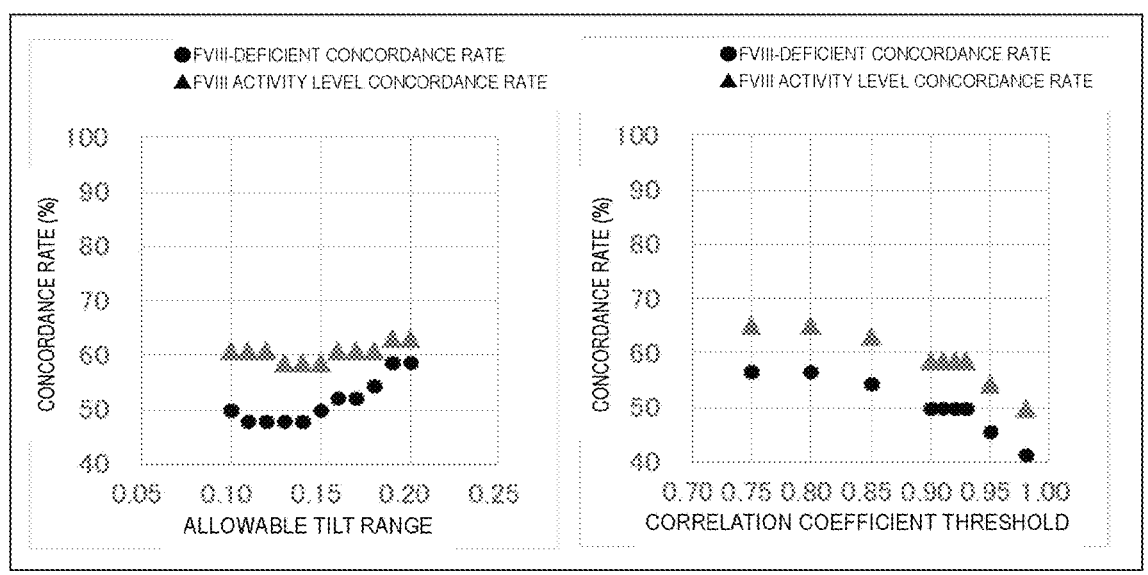
FIG. 21 shows influence of the allowable tilt range and correlation coefficient threshold in regression analysis on the FVIII-deficient concordance rate and FVIII activity-level concordance rate based on determination criteria 3

Example 7: Determination of FVIII Activity or Abnormality by Different Threshold By a procedure similar to that in Example 6, a state of the FVIII activity of the test specimen was determined in accordance with determination criteria 1 to 3, by changing the allowable tilt range and correlation coefficient threshold in the primary regression equation. As the parameter group, a combination parameter group of pTW_vTs_vW, which showed the highest FVIII-deficient concordance rate and FVIII activity level concordance rate in Example 5, was used. The tilt of the primary regression equation was changed from 1±0.05 to 1±0.25 (that is, allowable range of from 0.05 to 0.25) in a stepwise manner. Further, the threshold of the correlation coefficient was changed from >0.75 to >0.98 in a stepwise manner. The FVIII-deficient concordance rate and the FVIII activity level concordance rate were calculated under each condition. The results are shown in FIGS. 19 to 21.

The invention claimed is:
1. A method for analyzing a blood specimen, comprising:
acquiring a waveform related to a coagulation rate or a coagulation acceleration of a sample obtained by mixing a subject blood specimen with a reagent for measuring a coagulation time;
extracting a plurality of parameters characterizing the waveform related to the coagulation rate or the coagulation acceleration, the plurality of parameters including a plurality of coagulation rate parameters characterizing a plurality of calculation target areas of the waveform related to the coagulation rate, a plurality of coagulation acceleration parameters characterizing a plurality of calculation target areas of the waveform related to the coagulation acceleration, or a combination of the plurality of coagulation rate parameters and the plurality of coagulation acceleration parameters;
determining an activity level or activity abnormality of a coagulation factor in the subject blood specimen on the basis of the plurality of parameters; and
applying a treatment to a patient according to the activity level or activity abnormality of the coagulation factor, wherein
the plurality of parameters comprise one or more selected from the group consisting of:
a weighted average time vT, a weighted average height vH, a peak width vB, and a weighted average peak width vW, a B flattening vAB for the weighted average height, a W flattening vAW for the weighted average height, a B time rate vTB for the weighted average time, a W time rate vTW for the weighted average time, an average time vTa, an average height vHa, a B flattening vABa for the average height, a W flattening vAWa for the average height, an area start point time vTs, an area end point time vTe, an area median time vTm, an area time width vTr, a main peak start point time vNs, a main peak end point time vNe, and a main peak width vN for the plurality of calculation target areas of the waveform related to the coagulation rate;
a weighted average time pT, a weighted average height pH, a peak width pB, and a weighted average peak width pW, a B flattening pAB for the weighted average height, a W flattening pAW for the weighted average height, a B time rate pTB for the weighted average time, a W time rate pTW for the weighted average time, a main peak start point time pNs, a main peak end point time pNe, and a main peak width pN for a plurality of calculation target areas of a plus peak of the waveform related to the coagulation acceleration; and a weighted average time mT, a weighted average height mH, a peak width mB, and a weighted average peak width mW, a B flattening mAB for the weighted average height, a W flattening mAW for the weighted average height, a B time rate mTB for the weighted average time, a W time rate mTW for the weighted average time, a main peak start point time mNs, a main peak end point time mNe, and a main peak width mN for a plurality of calculation target areas of a minus peak of the waveform related to the coagulation acceleration.

2. The analysis method according to claim 1 wherein when the waveform related to the coagulation rate is defined as F(t) (t represents time) and each of t1 and t2 is defined as a time when F(t) is a predetermined value x (t1<t2), the calculation target area is an area satisfying F(t)≥x, and the vT and vH are represented by the following formulas, respectively:

$$vT = \frac{M}{\sum_{i=t1}^{t2} F(i)} \quad (3)$$

$$vH = \frac{M}{\sum_{i=t1}^{t2} i} \quad (4)$$

wherein $$M = \Sigma_{i=t1}^{t2}(i \times F(i)) \quad (2)$$

the vTa, vHa, and vTm are represented by the following formulas, respectively, when F(t), t1, and t2 are defined as described above and the number of data points from F(t1) to F(t2) is n:

$$vTa = \frac{\sum_{i=t1}^{t2} i}{n} \quad (5)$$

$$vHa = \frac{\sum_{i=t1}^{t2} F(i)}{n} \quad (6)$$

$$vTm = \frac{t1 + t2}{2} \quad (7)$$

the vB represents a time length to be F(t)≥x from t1 to t2,
the vW represents a time length to be F(t)≥vH from t1 to t2,
the vTs and vTe represent t1 and t2, respectively,
the vTr represents a time length from vTs to vTe,
the vNs represents a maximum time during a time period earlier than a time when F(t) shows a maximum value and satisfies F(t)=x in the calculation target area,
the vNe represents a minimum time during a time period later than a time when F(t) shows a maximum value and satisfies F(t)=x in the calculation target area,
the vN represents a time length from vNs to vNe,
the vAB represents a ratio of the vH to the vB,
the vAW represents a ratio of the vH to the vW,
the vTB represents a ratio of the vT to the vB,
the vTW represents a ratio of the vT to the vW,
the vABa represents a ratio of the vHa to the vB, and
the vAWa represents a ratio of the vHa to the vW.

3. The analysis method according to claim 1, wherein when the waveform related to the coagulation acceleration is defined as F'(t) (t represents time) and a time when F'(t) is a predetermined value x is defined as t1, t2 (t1<t2), the calculation target area is an area satisfying F'(t)≥x, and the pT and pH are represented by the following formulas, respectively:

$$pT = \frac{M}{\sum_{i=t1}^{t2} F'(i)} \quad (3)'$$

$$pH = \frac{M}{\sum_{i=t1}^{t2} i} \quad (4)'$$

wherein $$M = \Sigma_{i=t1}^{t2}(i \times F'(i)) \quad (2)'$$

the pB represents a time length to be F'(t)≥x from t1 to t2,
the pW represents a time length to be F'(t)≥pH from t1 to t2,
the pNs represents a maximum time during a time period earlier than a time when F'(t) shows a maximum value and satisfies F'(t)=x in the calculation target area,
the pNe represents a minimum time during a time period later than a time when F'(t) shows a maximum value and satisfies F'(t)=x in the calculation target area,
the pN represents a time length from pNs to pNe,
the pAB represents a ratio of the pH to the pB,
the pAW represents a ratio of the pH to the pW,
the pTB represents a ratio of the pT to the pB, and
the pTW represents a ratio of the pT to the pW.

4. The analysis method according to claim 1, wherein when the waveform related to the coagulation acceleration is defined as F'(t) (t represents time) and a time when F'(t) is a predetermined value x is defined as t1, t2 (t1<t2), the calculation target area is an area satisfying F'(t)≤x, and the mT and mH are represented by the following formulas, respectively:

$$mT = \frac{M}{\sum_{i=t1}^{t2} F'(i)} \quad (3)''$$

$$mH = \frac{M}{\sum_{i=t1}^{t2} i} \quad (4)''$$

wherein $$M = \Sigma_{i=t1}^{t2}(i \times F'(i)) \quad (2)''$$

the mB represents a time length to be F'(t)≤x from t1 to t2,
the mW represents a time length to be F'(t)≤mH from t1 to t2,
the mNs represents a maximum time during a time period earlier than a time when F'(t) shows a minimum value and satisfies F'(t)=x in the calculation target area,
the mNe represents a minimum time during a time period later than a time when F'(t) shows a minimum value and satisfies F'(t)=x in the calculation target area,
the mN represents a time length from mNs to mNe,
the mAB represents a ratio of the mH to the mB,
the mAW represents a ratio of the mH to the mW,
the mTB represents a ratio of the mT to the mB, and
the mTW represents a ratio of the mT to the mW.

5. The analysis method according to claim 2, wherein the predetermined value x is 0.5 to 99% of the maximum value of F(t), 0.5 to 99% of the maximum value of the plus peak of F'(t), or 0.5 to 99% of the minimum value of the minus peak of F'(t).

6. The analysis method according to claim 1, wherein the plurality of calculation target areas are 5 to 20 different areas.

7. The analysis method according to claim 1, wherein
the determination comprises comparing a group of the plurality of parameters with a corresponding group of parameters for a plurality of template blood specimens, and determining an activity level or activity abnormality of a coagulation factor in the subject blood specimen on the basis of a result of the comparison, wherein
each of the template blood specimens is a blood specimen of which an activity level or presence or absence of activity abnormality of the coagulation factor is known.

8. The analysis method according to claim 7, wherein the comparison comprises determining correlation between the group of the plurality of parameters for the subject blood specimen and the corresponding group of parameters for a plurality of template blood specimens, respectively.

9. The analysis method according to claim 8, wherein the determination comprises selecting a template blood specimen with which the correlation satisfies a predetermined condition, and determining an activity level or activity abnormality of a coagulation factor in the selected template blood specimen as an activity level or activity abnormality of the coagulation factor in the subject blood specimen.

10. The analysis method according to claim 1, wherein the coagulation factor is a blood coagulation factor VIII or a blood coagulation factor IX.

11. The analysis method according to claim 10, wherein the determination comprises determining a subject blood specimen derived from a patient with hemophilia A.

12. The analysis method according to claim 10, wherein the determination comprises determining a subject blood specimen derived from a patient with severe, moderate, or mild hemophilia A.

13. The analysis method according to claim 10, further comprising:
a second determination step of determining an activity level or activity abnormality of a blood coagulation factor IX in a subject blood specimen with which a blood coagulation factor VIII is determined to be not abnormal, wherein
the second determination step comprises comparing a group of parameters for the subject blood specimen with a corresponding group of parameters for a plurality of template blood specimens each of which an activity level or presence or absence of activity abnormality of a blood coagulation factor IX is known, and determining an activity level or activity abnormality of the blood coagulation factor IX in the subject blood specimen on the basis of a result of the comparison.

14. The analysis method according to claim 13, wherein the determination comprises determining a subject blood specimen derived from a patient with hemophilia B.

15. The analysis method according to claim 13, wherein the determination comprises determining a subject blood specimen derived from a patient with severe, moderate, or mild hemophilia B.

* * * * *